(12) United States Patent
Kawahara et al.

(10) Patent No.: US 7,910,585 B2
(45) Date of Patent: Mar. 22, 2011

(54) PYRIMIDINE DERIVATIVES

(75) Inventors: Eiji Kawahara, Ibaraki (JP); Takahiro Miyake, Ibaraki (JP); Johannes Roesel, Riehen (CH)

(73) Assignee: Novartis AG, Basel (CH)

( * ) Notice: Subject to any disclaimer, the term of this patent is extended or adjusted under 35 U.S.C. 154(b) by 883 days.

(21) Appl. No.: 11/660,714

(22) PCT Filed: Aug. 26, 2005

(86) PCT No.: PCT/EP2005/009255
§ 371 (c)(1),
(2), (4) Date: Feb. 20, 2007

(87) PCT Pub. No.: WO2006/021457
PCT Pub. Date: Mar. 2, 2006

(65) Prior Publication Data
US 2008/0293708 A1 Nov. 27, 2008

(30) Foreign Application Priority Data
Aug. 27, 2004 (GB) .................................. 0419160.7

(51) Int. Cl.
C07D 403/12 (2006.01)
C07D 403/14 (2006.01)
A61K 31/506 (2006.01)

(52) U.S. Cl. ........... 514/235.8; 514/252.14; 514/252.18; 514/252.19; 514/252.11; 514/275; 544/122; 544/295; 544/323; 544/324

(58) Field of Classification Search .................. 544/122, 544/295, 323, 324; 514/235.8, 252.14, 252.18, 514/252.19, 252.11, 275
See application file for complete search history.

(56) References Cited

FOREIGN PATENT DOCUMENTS

| WO | WO 00/39101 A1 | 7/2000 |
|---|---|---|
| WO | WO 03/018021 A1 | 3/2003 |
| WO | WO 03/078404 | 9/2003 |
| WO | WO 2004/063794 A2 | 7/2004 |
| WO | WO 2004/080980 | 9/2004 |

OTHER PUBLICATIONS

Traxler, Protein Tyrosine Kinase Inhibitors in Cancer Treatment, Expert Opinion on Therapeutic Patents, 7(6):571-588, 1997.*
Simone, Oncology: Introduction, Cecil Textbook of Medicine, 20$^{th}$ Edition, vol. 1, pp. 1004-1010, 1996.*

\* cited by examiner

*Primary Examiner* — Deepak Rao

(57) ABSTRACT

Novel pyrimidine derivatives of formula I

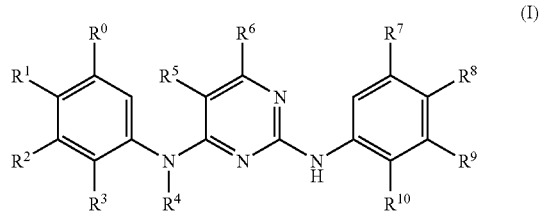

to processes for their production, their use as pharmaceuticals and to pharmaceutical compositions comprising them.

10 Claims, No Drawings

SEQUENCE LISTING

```
<160> NUMBER OF SEQ ID NOS: 2

<210> SEQ ID NO 1
<211> LENGTH: 21
<212> TYPE: DNA
<213> ORGANISM: artificial
<220> FEATURE:
<223> OTHER INFORMATION: 5-prime PCR primer

<400> SEQUENCE: 1
atggcagctg cttaccttga c                                         21

<210> SEQ ID NO 2
<211> LENGTH: 21
<212> TYPE: DNA
<213> ORGANISM: artificial
<220> FEATURE:
<223> OTHER INFORMATION: 3 prime PCR primer

<400> SEQUENCE: 2
tcagtgtggt ctcgtctgcc c                                         21
```

PYRIMIDINE DERIVATIVES

This application is a 371 of PCT/EP05/09255 filed Aug. 26, 2005.

The present invention relates to novel pyrimidine derivatives, to processes for their production, their use as pharmaceuticals and to pharmaceutical compositions comprising them.

More particularly the present invention provides in a first aspect, a compound of formula I

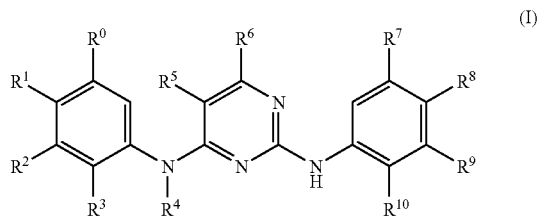

wherein
$R_0$ is hydrogen
$R_1$ is a unsubstituted or substituted 6 member mono cyclic or a 10 member bicyclic-heterocycle comprising 1 or 2 heteroatoms independently selected from N and O;
$R_2$ and $R_3$ together with the C and N to which they are attached form a heterocycle comprising at least 1 hetero atoms independently selected from N which is unsubstituted or substituted once or more by a substituent independently selected from loweralkyl and oxo;
$R_4$ is hydrogen
$R_5$ is halogen
$R_6$ is hydrogen
$R_7$ is hydrogen;
$R_8$ is hydrogen; halogen, $C_1$-$C_7$alkoxy; carbonyl unsubstituted or substituted by $C_1$-$C_7$alkyl; $C_1$-$C_7$alkoxy-$C_1$-$C_7$alkoxy; a 5 or 6 member heterocycle comprising 1, 2 hetero atoms independently selected from N or O and is unsubstituted or substituted by a substituent independently selected from hydroxy, $C_1$-$C_7$alkyl, mono or di-$C_1$-$C_7$alkylamino, a 6 member heterocycle comprising 1 or 2 N ring atoms unsubstituted or substituted by $C_1$-$C_7$alkyl; 5 or 6 member heterocycle-$C_1$-$C_7$alkoxy comprising 1 N ring atom unsubstituted or substituted by $C_1$-$C_7$alkyl;
$R_9$ is hydrogen;
$R_{10}$ is hydrogen, halogen or $C_1$-$C_7$alkoxy;
or a salt thereof.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

$C_1$-$C_8$alkyl denotes a an alkyl radical having from 1 up to 8, especially up to 4 carbon atoms, the radicals in question being either linear or branched with single or multiple branching; preferably, $C_1$-$C_8$alkyl is butyl, such as n-butyl, sec-butyl, isobutyl, tert-butyl, propyl, such as n-propyl or isopropyl, ethyl or methyl; especially methyl, propyl or tert-butyl.

$C_2$-$C_8$alkenyl denotes a an alkenyl radical having from 2 up to 8, especially up to 5 carbon atoms, the radicals in question being either linear or branched with single or multiple branching; preferably, $C_2$-$C_8$alkenyl is pentenyl, such as 3-methyl-2-buten-2-yl, butenyl, such as 1- or 2-butenyl or 2-buten-2-yl, propenyl, such as 1-propenyl or allyl, or vinyl.

$C_2$-$C_8$alkinyl denotes a an alkinyl radical having from 2 up to 8, especially up to 5 carbon atoms, the radicals in question being either linear or branched; preferably, $C_2$-$C_8$alkinyl is propinyl, such as 1-propinyl or propargyl, or acetylenyl.

$C_3$-$C_8$cycloalkyl denotes a cycloalkyl radical having from 3 up to 8 carbon atoms, such as cyclopropyl, cyclobutyl, cyclopentyl, cyclohexyl, cycloheptyl or cyclooctyl, preferably cyclopropyl, cyclopentyl or cyclohexyl.

$C_1$-$C_8$alkoxy is especially methoxy, ethoxy, isopropyloxy, or tert-butoxy.

Hydroxy$C_1$-$C_8$alkyl is especially hydroxymethyl, 2-hydroxyethyl or 2-hydroxy-2-propyl.

Hydroxy$C_1$-$C_8$alkoxy is especially 2-hydroxyethoxy or 3-hydroxypropoxy.

$C_1$-$C_8$alkoxy$C_1$-$C_8$alkoxy is especially 2-methoxyethoxy.

$C_1$-$C_8$alkoxy$C_1$-$C_8$alkyl is especially methoxymethyl, 2-methoxyethyl or 2-ethoxyethyl.

Halogen is preferably fluorine, chlorine, bromine, or iodine, especially fluorine, chlorine, or bromine.

Halo$C_1$-$C_8$alkyl is preferably chloro$C_1$-$C_8$alkyl or fluoro$C_1$-$C_8$alkyl, especially trifluoromethyl or pentafluoroethyl.

Halo$C_1$-$C_8$alkoxy is preferably chloro$C_1$-$C_8$alkoxy or fluoro$C_1$-$C_8$alkoxy, especially trifluoromethoxy.

$C_1$-$C_8$alkoxycarbonyl is especially tert-butoxycarbonyl, iso-propoxycarbonyl, methoxycarbonyl or ethoxycarbonyl.

Unsubstituted or substituted carbamoyl is carbamoyl substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstituted or substituted $C_5$-$C_{10}$aryl, or amino$C_1$-$C_8$alkyl, or carbamoyl wherein the substituents and the nitrogen atom of the carbamoyl group represent a 5 or 6 membered heterocyclyl further comprising 0, 1 or 2 hetero atoms selected from N, O and S; and is preferably carbamoyl, methylcarbamoyl, dimethylcarbamoyl, propylcarbamoyl, hydroxyethyl-methyl-carbamoyl, di(hydroxyethyl)carbamoyl, dimethylaminoethylcarbamoyl, or pyrrolidinocarbonyl, piperidinocarbonyl, N-methylpiperazinocarbonyl or morpholinocarbonyl, especially carbamoyl or dimethylcarbamoyl.

Unsubstituted or substituted sulfamoyl is sulfamoyl substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstituted or substituted $C_5$-$C_{10}$aryl, or amino$C_1$-$C_8$alkyl, or sulfamoyl wherein the substituents and the nitrogen atom of the sulfamoyl group represent a 5 or 6 membered heterocyclyl further comprising 0, 1 or 2 hetero atoms selected from N, O and S; and is preferably sulfamoyl, methylsulfamoyl, propylsulfamoyl, cyclopropylmethyl-sulfamoyl, 2,2,2-trifluoroethylsulfamoyl, dimethylaminoethylsulfamoyl, dimethylsulfamoyl, hydroxyethyl-methyl-sulfamoyl, di(hydroxyethyl)sulfamoyl, or pyrrolidinosulfonyl, piperidinosulfonyl, N-methylpiperazinosulfonyl or morpholinosulfonyl, especially sulfamoyl or methylsulfamoyl.

Unsubstituted or substituted amino is amino substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstituted or substituted $C_5$-$C_{10}$aryl, amino$C_1$-$C_8$alkyl, acyl, e.g. formyl, $C_1$-$C_8$alkylcarbonyl, $C_5$-$C_{10}$arylcarbonyl, $C_1$-$C_8$alkylsulfonyl or $C_5$-$C_{10}$arylsulfonyl, and is preferably amino, methylamino, dimethylamino, propylamino, benzylamino, hydroxyethyl-methyl-amino, di(hydroxyethyl)amino, dimethylaminoethyl-amino, acetylamino, acetyl-methyl-amino, benzoylamino, methylsulfonylamino or phenylsulfonylamino, especially amino or dimethylamino.

Amino$C_1$-$C_8$alkyl is especially aminoethyl, methylaminoethyl, dimethylaminoethyl or dimethylaminopropyl.

Unsubstituted or substituted $C_5$-$C_{10}$aryl is, for example, phenyl, indenyl, indanyl, naphthyl, or 1,2,3,4-tetrahydronaphthalenyl, optionally substituted by $C_1$-$C_8$alkyl, $C_1$-$C_8$alkoxy$C_1$-$C_8$alkyl, halo$C_1$-$C_8$alkyl, hydroxy, $C_1$-$C_8$alkoxy, methylenedioxy, amino, substituted amino, halogen, carboxy, $C_1$-$C_8$alkoxycarbonyl, carbamoyl, sulfamoyl, cyano or nitro; preferably phenyl, tolyl, trifluoromethylphenyl, methoxyphenyl, dimethoxyphenyl, methylenedioxyphenyl, chlorophenyl or bromophenyl, whereby the substituents may be in ortho, meta or para position, preferably meta or para.

$C_5$-$C_{10}$aryloxy is especially phenoxy or methoxyphenoxy, e.g. p-methoxyphenoxy.

$C_5$-$C_{10}$aryl$C_1$-$C_8$alkyl is especially benzyl or 2-phenylethyl.

$C_5$-$C_{10}$aryl$C_1$-$C_8$alkoxy is especially benzyloxy or 2-phenylethoxy.

Unsubstituted or substituted 5 or 6 membered heterocyclyl comprising 1, 2 or 3 hetero atoms selected from N, O and S may be unsaturated, partially unsaturated or saturated, and further condensed to a benzo group or a 5 or 6 membered heterocyclyl group, and may be bound through a hetero or a carbon atom, and is, for example, pyrrolyl, indolyl, pyrrolidinyl, imidazolyl, benzimidazolyl, pyrazolyl, triazolyl, benzotriazolyl, tetrazolyl, pyridyl, quinolinyl, isoquinolinyl, 1,2,3,4-tetrahydroquinolinyl, piperidyl, pyrimidinyl, pyrazinyl, piperazinyl, purinyl, tetrazinyl, oxazolyl, isoxalyl, morpholinyl, thiazolyl, benzothiazolyl, oxadiazolyl, and benzoxadiazolyl. Substituents considered are $C_1$-$C_8$alkyl, hydroxy$C_1$-$C_8$alkyl, $C_1$-$C_8$alkoxy$C_1$-$C_8$alkyl, $C_1$-$C_8$alkoxy$C_1$-$C_8$alkoxy, halo$C_1$-$C_8$alkyl, hydroxy, amino, substituted amino, $C_1$-$C_8$alkoxy, halogen, carboxy, $C_1$-$C_8$alkylcarbonyl, $C_1$-$C_8$alkoxycarbonyl, carbamoyl, $C_1$-$C_8$alkylcarbamoyl, cyano, oxo, or unsubstituted or substituted 5 or 6 membered heterocyclyl as defined in this paragraph. 5 or 6 membered heterocyclyl preferably comprises 1 or 2 hetero atoms selected from N, O and S, and is especially indolyl, pyrrolidinyl, pyrrolidonyl, imidazolyl, N-methylimidazolyl, benzimidazolyl, S,S-dioxoisothiazolidinyl, piperidyl, 4-acetylaminopiperidyl, 4-methylcarbamoylpiperidyl, 4-piperidinopiperidyl, 4-cyanopiperidyl, piperazinyl, N-methylpiperazinyl, N-(2-hydroxyethyl)piperazinyl, morpholinyl, 1-aza-2,2-dioxo-2-thiacyclohexyl, or sulfolanyl.

In unsubstituted or substituted heterocyclyloxy, heterocyclyl has the meaning as defined above, and is especially N-methyl-4-piperidyloxy. In unsubstituted or substituted heterocyclyl$C_1$-$C_8$alkoxy, heterocyclyl has the meaning as defined above, and is especially 2-pyrrolidinoethoxy, 2-morpholinoethoxy, 3-morpholinopropoxy, 1-methyl-piperidin-3-ylmethoxy, 3-(N-methylpiperazino)propoxy or 2-(1-imidazolyl)ethoxy.

In a 5 or 6 membered carbocyclic or heterocyclic ring comprising 0, 1, 2 or 3 heteroatoms selected from N, O and S, and formed by two adjacent substituents together with the benzene ring, the ring may be further substituted, e.g. by $C_1$-$C_8$alkyl, $C_1$-$C_8$alkoxy, halo$C_1$-$C_8$alkyl, hydroxy, amino, substituted amino, $C_1$-$C_8$alkoxy, halogen, carboxy, $C_1$-$C_8$alkoxycarbonyl, carbamoyl, cyano, or oxo. The two adjacent substituents forming such a ring are preferably propylene, butylene, 1-aza-2-propylidene, 3-aza-1-propylidene, 1,2-diaza-2-propylidene, 2,3-diaza-1-propylidene, 1-oxapropylene, 1-oxapropylidene, methylenedioxy, difluoromethylenedioxy, 2-aza-1-oxopropylene, 2-aza-2-methyl-1-oxopropylene, 1-aza-2-oxopropylene, 2-aza-1,1-dioxo-1-thiapropylene or the corresponding butylene derivatives forming a 6 membered ring.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I have valuable pharmacological properties, as described hereinbefore and hereinafter.

In formula I the following significances are preferred independently, collectively or in any combination or sub-combination.

$R_0$ is hydrogen $R_1$ is piperidinyl, piperazinyl or pyrazino-oxazinyl each of which is unsubstituted or substituted by pipereridinyl, hydroxy, $C_1$-$C_7$alkyl, piperazinyl, $C_1$-$C_7$alkyl-piperazinyl;

$R_2$ and $R_3$ together with the C and N to which they are indolyl or isoquinolinyl both of which are unsubstituted or substituted by $C_1$-$C_7$alkyl and/or oxo;

$R_4$ is hydrogen $R_5$ is halogen $R_6$ is hydrogen $R_7$ is hydrogen;

$R_8$ is hydrogen; halogen, $C_1$-$C_7$alkoxy; carbornyl unsubstituted or substituted by $C_1$-$C_7$alkyl; $C_1$-$C_7$alkoxy-$C_1$-$C_7$alkoxy; piperazinyl-$C_1$-$C_7$alkoxy; morpholino; piperindinyl; bipiperindinyl; pyrrolidinyl; piperazinyl-piperidinyl; wherein piperazinyl-$C_1$-$C_7$alkoxy, morpholino; piperindinyl, bipiperindinyl, pyrrolidinyl, piperazinyl-piperidinyl are unsubstituted or substituted by a substituent independently selected from hydroxy, $C_1$-$C_7$alkyl, mono or di-$C_1$-$C_7$alkylamino;

$R_9$ is hydrogen;
$R_{10}$ is hydrogen, halogen or $C_1$-$C_7$alkoxy
or a salt thereof.

More preferred are the following meanings, independently, collectively or in any combination or sub-combination:

A)
$R_0$ is hydrogen
$R_1$ is hydroxy-piperidinyl, piperidinyl-piperidinyl, piperazinyl, $C_1$-$C_7$alkyl-piperazinyl, piperazinyl-piperidinyl, $C_1$-$C_7$alkyl-piperazinyl-piperidinyl or pyrazino-oxazinyl;
$R_2$ and $R_3$ together with the C and N to which they are indolyl or isoquinolinyl both of which are substituted by $C_1$-$C_7$alkyl and oxo;
$R_4$ is hydrogen
$R_5$ is halogen
$R_6$ is hydrogen
$R_7$ is hydrogen;
$R_8$ is hydrogen; halogen, C1-C7alkoxy; $C_1$-$C_7$alkyl-carbornyl unsubstituted; C1-C7alkoxy-C1-C7alkoxy; $C_1$-$C_7$alkyl-piperazinyl-C1-C7alkoxy; morpholino; hydroxy-piperindinyl; $C_1$-$C_7$alkyl-piperazinyl-piperindinyl; bipiperindinyl; di-$C_1$-$C_7$alkylamino-pyrrolidinyl;
$R_9$ is hydrogen;
$R_{10}$ is hydrogen, halogen or $C_1$-$C_7$alkoxy;
or a salt thereof.

B)
$R_0$ is hydrogen
$R_1$ is hydroxy-piperidinyl, piperidinyl-piperidinyl, piperazinyl, methyl-piperazinyl, isopropyl-piperazinyl, piperazinyl-piperidinyl, methyl-piperazinyl-piperidinyl or pyrazino-oxazinyl;
$R_2$ and $R_3$ together with the C and N to which they are methyl-isoindolone or methyl-isoquinolinone;
$R_4$ is hydrogen
$R_5$ is chloro
$R_6$ is hydrogen
$R_7$ is hydrogen;
$R_8$ is hydrogen; Fluoro, methoxy; methyl-carbornyl unsubstituted; methoxy-ethoxy; methyl-piperazinyl-ethoxy; morpholino; hydroxy-piperindinyl; methyl-piperazinyl-piperindinyl; bipiperindinyl; dimethylamino-pyrrolidinyl;
$R_9$ is hydrogen;
$R_{10}$ is hydrogen, fluoro or methoxy;
or a salt thereof.

Most preferred as compounds of the formula I are those wherein the substituents have the meaning given in the Examples.

A compound of formula I selected from
4-[1,4']Bipiperidinyl-1'-yl-7-[5-chloro-2-(2-methoxy-4-morpholin-4-yl-phenylamino)-pyrimidin-4-ylamino]-2-methyl-2,3-dihydro-isoindol-1-one,
4-[1,4']Bipiperidinyl-1'-yl-7-{5-chloro-2-[2-methoxy-4-(2-methoxy-ethoxy)-phenylamino]-pyrimidin-4-ylamino}-2-methyl-2,3-dihydro-isoindol-1-one,
7-[5-Chloro-2-(2-methoxy-4-morpholin-4-yl-phenylamino)-pyrimidin-4-ylamino]-4-(4-hydroxy-piperidin-1-yl)-2-methyl-2,3-dihydro-isoindol-1-one,
7-[5-Chloro-2-(2,4-dimethoxy-phenylamino)-pyrimidin-4-ylamino]-4-(4-hydroxy-piperidin-1-yl)-2-methyl-2,3-dihydro-isoindol-1-one,
4-[1,4']Bipiperidinyl-1'-yl-7-[5-chloro-2-(2,4-dimethoxy-phenylamino)-pyrimidin-4-ylamino]-2-methyl-2,3-dihydro-isoindol-1-one,
4-[1,4']Bipiperidinyl-1'-yl-7-[5-chloro-2-(2-methoxy-phenylamino)-pyrimidin-4-ylamino]-2-methyl-2,3-dihydro-isoindol-1-one,
7-[5-Chloro-2-(2,4-dimethoxy-phenylamino)-pyrimidin-4-ylamino]-4-(R)-hexahydro-pyrazino[2,1-c][1,4]oxazin-8-yl-2-methyl-2,3-dihydro-isoindol,
7-{5-Chloro-2-[4-(4-hydroxy-piperidin-1-yl)-2-methoxy-phenylamino]-pyrimidin-4-ylamino}-4-(R)-hexahydro-pyrazino[2,1-c][1,4]oxazin-8-yl-2-methyl-2,3-dihydro-isoindol-1-one,
7-[5-Chloro-2-(2,4-dimethoxy-phenylamino)-pyrimidin-4-ylamino]-2-methyl-4-piperazin-1-yl-2,3-dihydro-isoindol-1-one,
7-[5-Chloro-2-(2,4-dimethoxy-phenylamino)-pyrimidin-4-ylamino]-2-methyl-4-(4-methyl-piperazin-1-yl)-2,3-dihydro-isoindol-1-one,
7-[5-Chloro-2-(2-methoxy-phenylamino)-pyrimidin-4-ylamino]-2-methyl-4-piperazin-1-yl-2,3-dihydro-isoindol-1-one,
7-[5-Chloro-2-(2-methoxy-phenylamino)-pyrimidin-4-ylamino]-2-methyl-4-(4-methyl-piperazin-1-yl)-2,3-dihydro-isoindol-1-one,
7-[5-Chloro-2-(2,4-dimethoxy-phenylamino)-pyrimidin-4-ylamino]-4-(4-isopropyl-piperazin-1-yl)-2-methyl-2,3-dihydro-isoindol-1-one,
7-[5-Chloro-2-(2-methoxy-phenylamino)-pyrimidin-4-ylamino]-4-(4-isopropyl-piperazin-1-yl)-2-methyl-2,3-dihydro-isoindol-1-one,
4-{5-Chloro-4-[7-(4-isopropyl-piperazin-1-yl)-2-methyl-3-oxo-2,3-dihydro-1H-isoindol-4-ylamino]-pyrimidin-2-ylamino}-3-methoxy-N-methyl-benzamide,
7-[5-Chloro-2-(2-methoxy-4-morpholin-4-yl-phenylamino)-pyrimidin-4-ylamino]-4-(4-isopropyl-piperazin-1-yl)-2-methyl-2,3-dihydro-isoindol-1-one,
7-{5-Chloro-2-[4-((S)-3-dimethylamino-pyrrolidin-1-yl)-2-methoxy-phenylamino]-pyrimidin-4-ylamino}-4-(4-isopropyl-piperazin-1-yl)-2-methyl-2,3-dihydro-isoindol-1-one,
7-(5-Chloro-2-{2-methoxy-4-[2-(4-methyl-piperazin-1-yl)-ethoxy]-phenylamino}-pyrimidin-4-ylamino)-4-(4-isopropyl-piperazin-1-yl)-2-methyl-2,3-dihydro-isoindol-1-one,
7-{5-Chloro-2-[4-(4-hydroxy-piperidin-1-yl)-2-methoxy-phenylamino]-pyrimidin-4-ylamino}-4-(4-isopropyl-piperazin-1-yl)-2-methyl-2,3-dihydro-isoindol-1-one,
7-{5-Chloro-2-[4-((R)-3-dimethylamino-pyrrolidin-1-yl)-2-methoxy-phenylamino]-pyrimidin-4-ylamino}-4-(4-isopropyl-piperazin-1-yl)-2-methyl-2,3-dihydro-isoindol-1-one,
7-[2-(4-[1,4']Bipiperidinyl-1'-yl-2-methoxy-phenylamino)-5-chloro-pyrimidin-4-ylamino]-4-(4-isopropyl-piperazin-1-yl)-2-methyl-2,3-dihydro-isoindol-1-one,
7-(5-Chloro-2-{2-methoxy-4-[4-(4-methyl-piperazin-1-yl)-piperidin-1-yl]-phenylamino}-pyrimidin-4-ylamino)-4-(4-isopropyl-piperazin-1-yl)-2-methyl-2,3-dihydro-isoindol-1-one,
7-[5-Chloro-2-(4-morpholin-4-yl-phenylamino)-pyrimidin-4-ylamino]-4-(4-isopropyl-piperazin-1-yl)-2-methyl-2,3-dihydro-isoindol-1-one, 7-{5-Chloro-2-[2-methoxy-4-(2-methoxy-ethoxy)-phenylamino]-pyrimidin-4-ylamino}-4-(4-isopropyl-piperazin-1-yl)-2-methyl-2,3-dihydro-isoindol-1-one,
7-[5-Chloro-2-(2-methoxy-phenylamino)-pyrimidin-4-ylamino]-2-methyl-4-(4-piperazin-1-yl-piperidin-1-yl)-2,3-dihydro-isoindol-1-one,
7-[5-Chloro-2-(2-methoxy-phenylamino)-pyrimidin-4-ylamino]-2-methyl-4-[4-(4-methyl-piperazin-1-yl)-piperidin-1-yl]-2,3-dihydro-isoindol-1-one,
7-[5-Chloro-2-(2,4-dimethoxy-phenylamino)-pyrimidin-4-ylamino]-2-methyl-4-(4-piperazin-1-yl-piperidin-1-yl)-2,3-dihydro-isoindol-1-one,
7-[5-Chloro-2-(2,4-dimethoxy-phenylamino)-pyrimidin-4-ylamino]-2-methyl-4-[4-(4-methyl-piperazin-1-yl)-piperidin-1-yl]-2,3-dihydro-isoindol-1-one,
8-[5-Chloro-2-(2-methoxy-phenylamino)-pyrimidin-4-ylamino]-5-(4-isopropyl-piperazin-1-yl)-2-methyl-3,4-dihydro-2H-isoquinolin-1-one,
8-[5-Chloro-2-(2,4-dimethoxy-phenylamino)-pyrimidin-4-ylamino]-5-(4-isopropyl-piperazin-1-yl)-2-methyl-3,4-dihydro-2H-isoquinolin-1-one,
8-[5-Chloro-2-(2-fluoro-phenylamino)-pyrimidin-4-ylamino]-5-(4-isopropyl-piperazin-1-yl)-2-methyl-3,4-dihydro-2H-isoquinolin-1-one,
8-{5-Chloro-2-[2-methoxy-4-(2-methoxy-ethoxy)-phenylamino]-pyrimidin-4-ylamino}-5-(4-isopropyl-piperazin-1-yl)-2-methyl-3,4-dihydro-2H-isoquinolin-1-one,
8-[5-Chloro-2-(2-methoxy-4-morpholin-4-yl-phenylamino)-pyrimidin-4-ylamino]-5-(4-isopropyl-piperazin-1-yl)-2-methyl-3,4-dihydro-2H-isoquinolin-1-one,
or a salt thereof are most preferred.

The present invention also provides a process for the production of a compound of formula I, comprising reacting a compound of formula I,

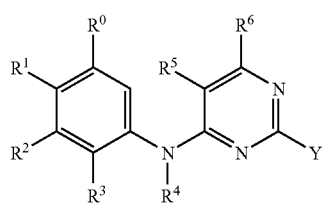

(II)

wherein $R^0$, $R^1$, $R^2$, $R^3$, $R^4$, $R^5$, and $R^6$ are as defined above, and Y is a leaving group, preferably halogen such as bromide, iodine, or in particular chloride;
with a compound of formula III

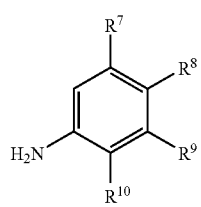

(III)

wherein $R^7$, $R^8$, $R^9$ and $R^{10}$ are as defined above;
and, if desired, converting a compound of formula I, wherein the substituents have the meaning as defined above, into another compound of formula I as defined;
and recovering the resulting compound of formula I in free from or as a salt, and, when required, converting the compound of formula I obtained in free form into the desired salt, or an obtained salt into the free form.

The reaction can be carried out in a manner known per se, the reaction conditions being dependent especially on the reactivity of the leaving group Y and the reactivity of the amino group in the aniline of formula III, usually in the presence of a suitable solvent or diluent or of a mixture thereof and, if necessary, in the presence of an acid or a base, with cooling or, preferably, with heating, for example in a temperature range from approximately −30° C. to approximately +150° C., especially approximately from 0° C. to +100° C., preferably from room temperature (approx. +20° C.) to +80° C., in an open or closed reaction vessel and/or in the atmosphere of an inert gas, for example nitrogen.

If one or more other functional groups, for example carboxy, hydroxy or amino, are or need to be protected in a compound of formula II or III, because they should not take part in the reaction, these are such groups as are usually used in the synthesis of peptide compounds, cephalosporins and penicillins, as well as nucleic acid derivatives and sugars.

The protecting groups may already be present in precursors and should protect the functional groups concerned against unwanted secondary reactions, such as substitution reaction or solvolysis. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove.

Salts of a compound of formula I with a salt-forming group may be prepared in a manner known per se. Acid addition salts of compounds of formula I may thus be obtained by treatment with an acid or with a suitable anion exchange reagent.

Salts can usually be converted to compounds in free form, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates.

The compounds of formula I, including their salts, are also obtainable in the form of hydrates, or their crystals can include for example the solvent used for crystallization (present as solvates).

The compound of formula II used as starting materials may be obtained by reacting a compound of formula IV

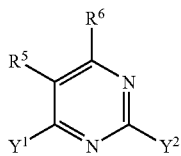

(IV)

with a compound of formula V

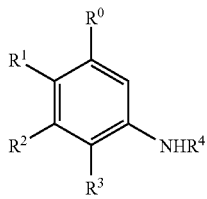

(V)

wherein $R^1$, $R^2$, $R^3$, $R^4$, $R^5$ and $R^6$ are as defined above, and $Y^1$ and $Y^2$ are identical or different leaving groups as defined above for Y. The reaction conditions are those mentioned above for the reaction of a compound of formula II with a compound of formula III.

The compounds of formula IV and V are known or may be produced in accordance with known procedures.

The compounds of formula I and their pharmaceutically acceptable salts exhibit valuable pharmacological properties when tested in vitro in cell-free kinase assays and in cellular assays, and are therefore useful as pharmaceuticals. In particular, the compounds of the invention are inhibitors of Focal Adhesion Kinase, and are useful as pharmaceuticals to treat conditions caused by a malfunction of signal cascades connected with Focal Adhesion Kinase, in particular tumors as described hereinbelow.

Focal Adhesion Kinase (FAK) is a key enzyme in the integrin-mediated outside-in signal cascade (D. Schlaepfer et al., Prog Biophys Mol Biol 1999, 71, 435-478). Interaction between cells and extracellular matrix (ECM) proteins is transduced as intracellular signals important for growth, survival and migration through cell surface receptors, integrins. FAK plays an essential role in these integrin-mediated outside-in signal cascades. The trigger in the signal transduction cascade is the autophosphorylation of Y397. Phosphorylated Y397 is a SH2 docking site for Src family tyrosine kinases. The bound c-Src kinase phosphorylates other tyrosine residues in FAK. Among them, phosphorylated Y925 becomes a binding site for the SH2 site of Grb2 small adaptor protein. This direct binding of Grb2 to FAK is one of the key steps for the activation of down stream targets such as the Ras-ERK2/MAP kinase cascade.

The inhibition of endogenous FAK signalling results in reduced motility and in some cases induces cell death. On the other hand, enhancing FAK signalling by exogenous expression increases cell motility and transmitting a cell survival signal from ECM. In addition FAK is overexpressed in invasive and metastatic epithelial, mesenchymal, thyroid and prostate cancers. Consequently, an inhibitor of FAK is likely to be a drug for anti-tumor growth and metastasis. The compounds of the invention are thus indicated, for example, to prevent and/or treat a vertebrate and more particularly a mammal, affected by a neoplastic disease, in particular breast tumor, cancer of the bowel (colon and rectum), stomach cancer and cancer of the ovary and prostate, non-small cell lung cancer, small cell lung cancer, cancer of liver, melanoma, bladder tumor and cancer of head and neck.

The relation between FAK inhibition and immuno-system is described e.g. in G. A. van Seventer et al., Eur. J. Immunol. 2001, 31, 1417-1427. Therefore, the compounds of the invention are, for example, useful to prevent and/or treat a vertebrate and more particularly a mammal, affected by immune system disorders, diseases or disorders mediated by T lymphocytes, B lymphocytes, mast cells and/or eosinophils e.g. acute or chronic rejection of organ or tissue allo- or xenografts, atherosclerosis, vascular occlusion due to vascular injury such as angioplasty, restenosis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hemorrhage shock, or traumatic shock. The agent of the invention are also useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated with therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

Compounds of the invention are active in a FAK assay system as described in the Examples, and show an inhibition $IC_{50}$ in the range of 1 nM to 100 nM.

The compounds of the present invention also exhibit powerful inhibition of the tyrosine kinase activity of anaplastic lymphoma kinase (ALK) and the fusion protein of NPM-ALK. This protein tyrosine kinase results from a gene fusion of nucleophosmin (NPM) and the anaplastic lymphoma kinase (ALK), rendering the protein tyrosine kinase activity of ALK ligand-independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+ NHL or Alkomas, in inflammatory myofibroblastic tumors (IMT) and neuroblastomas. (Duyster J et al. 2001 Oncogene 20, 5623-5637). In addition to NPM-ALK, other gene fusions have been identified in human hematological and neoplastic diseases; mainly TPM3-ALK (a fusion of nonmuscle tropomyosin with ALK).

The inhibition of ALK tyrosine kinase activity can be demonstrated using known methods, for example using the recombinant kinase domain of the ALK in analogy to the VEGF-R kinase assay described in J. Wood et al. Cancer Res. 60, 2178-2189 (2000). In vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [γ-$^{33}$P]-ATP, 2 µM ATP, 3 µg/ml poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition. Compared with the control without inhibitor, the compounds of formula I inhibit the enzyme activity by 50% ($IC_{50}$), for example in a concentration of from 0.001 to 0.5 µM, especially from 0.01 to 0.1 µM.

The compounds of formula I potently inhibit the growth of human NPM-ALK overexpressing murine BaF3 cells (DSMZ Deutsche Sammlung von Mikroorganismen und Zellkulturen GmbH, Braunschweig, Germany). The expression of NPM-ALK is achieved by transfecting the BaF3 cell line with an expression vector pCIneo™ (Promega Corp., Madison Wis., USA) coding for NPM-ALK and subsequent selection of G418 resistant cells. Non-transfected BaF3 cells depend on IL-3 for cell survival. In contrast NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and result in antiproliferative activity. The antiproliferative activity of putative inhibitors of the NPM-ALK kinase can however be overcome by addition of IL-3 which provides growth signals through an NPM-ALK independent mechanism. [For an analogous cell system using FLT3 kinase see E Weisberg et al. Cancer Cell; 1, 433-443 (2002)]. The inhibitory activity of the compounds of formula I is determined, briefly, as follows: BaF3-NPM-ALK cells (15,000/ microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of Yopro™ staining [T Idziorek et al. J. Immunol. Methods; 185: 249-258 (1995)]: 25 µl of lysis buffer consisting of 20 mM sodium citrate, pH 4.0, 26.8 mM sodium chloride, 0.4% NP40, 20 mM EDTA and 20 mM is added to each well. Cell lysis is completed within 60 min at room temperature and total amount of Yopro bound to DNA is determined by measurement using the Cytofluor II 96-well reader (PerSeptive Biosystems) with the following settings: Excitation (nm) 485/20 and Emission (nm) 530/25. $IC_{50}$ values are determined by a computer-aided system using the formula:

$$IC_{50}=[(ABS_{test}-ABS_{start})/(ABS_{control}-ABS_{start})] \times 100 \cdot (ABS=absorption)$$

The $IC_{50}$ value in those experiments is given as that concentration of the test compound in question that results in a cell count that is 50% lower than that obtained using the control without inhibitor. The compounds of formula I exhibit inhibitory activity with an $IC_{50}$ in the range from approximately 0.01 to 1 µM.

The antiproliferative action of the compounds of formula I can also be determined in the human KARPAS-299 lymphoma cell line (DSMZ Deutsche Sammlung von Mikroorganismen und Zellkulturen GmbH, Braunschweig, Germany) [described in W G Dirks et al. Int. J. Cancer 100, 49-56 (2002)] using the same methodology described above for the BaF3-NPM-ALK cell line. The compounds of formula I exhibit inhibitory activity with an $IC_{50}$ in the range from approximately 0.01 to 1 µM.

The action of the compounds of formula I on autophosphorylation of the ALK can be determined in the human KARPAS-299 lymphoma cell line by means of an immunoblot as described in W G Dirks et al. Int. J. Cancer 100, 49-56 (2002). In that test the compounds of formula I exhibit an $IC_{50}$ of approximately from 0.001 to 1 µM.

For the above uses in the treatment of neoplastic diseases and immune system disorders the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of the invention may be administered by any conventional route, in particular parenterally, for example in the form of injectable solutions or suspensions, enterally, preferably orally, for example in the form of tablets or capsules, topically, e.g. in the form of lotions, gels, ointments or creams, or in a nasal or a suppository form. Pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance. Topical administration is e.g. to the skin. A further form of topical administration is to the eye.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol), "Labrafil M 1944 CS" (unsaturated polyglycolized glycerides prepared by alcoholysis of apricot kernel oil and consisting of glycerides and polyethylene glycol ester), "Labrasol" (saturated polyglycolized glycerides prepared by alcoholysis of TCM and consisting of glycerides and polyethylene glycol ester; all available from Gattefosse, France), and/or "Miglyol 812" (triglyceride of saturated fatty acids of chain length $C_8$ to $C_{12}$ from Huls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The compounds of the invention may be administered as the sole active ingredient or together with other drugs useful against neoplastic diseases or useful in immunomodulating regimens. For example, the agents of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, CD40, CD45, CD58, CD80, CD86, CD152, CD137, CD154, ICOS, LFA-1, VLA-4 or their ligands, or other immunomodulatory compounds, e.g. CTLA4Ig.

In accordance with the foregoing, the present invention also provides:

(1) A compound of the invention for use as a pharmaceutical;
(2) a compound of the invention for use as a FAK inhibitor, an ALK inhibitor and/or ZAP-70 inhibitor, for example for use in any of the particular indications hereinbefore set forth;
(3) a pharmaceutical composition, e.g. for use in any of the indications herein before set forth, comprising a compound of the invention as active ingredient together with one or more pharmaceutically acceptable diluents or carriers;
(4) a method for the treatment of any particular indication set forth hereinbefore in a subject in need thereof which comprises administering an effective amount of a compound of the invention or a pharmaceutical composition comprising same;
(5) the use of a compound of the invention for the manufacture of a medicament for the treatment or prevention of a disease or condition in which FAK, ALK and/or ZAP-70 activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;
(7) a combination comprising a therapeutically effective amount of a compound of the invention and one or more further drug substances, said further drug substance being useful in any of the particular indications set forth hereinbefore;
(8) use of a compound of the invention for the manufacture of a medicament for the treatment or prevention of a disease which responds to inhibition of the anaplastic lymphoma kinase;
(9) the use according to (8), wherein the disease to be treated is selected from anaplastic large-cell lymphoma, non-Hodgkin's lymphomas, inflammatory myofibroblastic tumors and neuroblastomas;
(10) the use according to (8) or (9), wherein the compound is or a pharmaceutically acceptable salt of any one of the examples;
(11) a method for the treatment of a disease which responds to inhibition of the anaplastic lymphoma kinase, especially a disease selected from anaplastic large-cell lymphoma, non-Hodgkin's lymphomas, inflammatory myofibroblastic tumors and neuroblastomas, comprising administering an effective amount of a compound of the invention or a pharmaceutically acceptable salt thereof.

Additionally preferred a compound according to the present invention that is useful as herein before described is a compound specifically mentioned in the examples.

Additional specifically preferred compounds according to the present invention that are useful either as FAK inhibitor, as ALK inhibitor or for inhibition of both and which may be prepared essentially according to the methods described hereinbefore are the following:

EXAMPLES

Abbreviations

AcOH=acetic acid, ALK=anaplastic lymphoma kinase, ATP=adenosine 5'-triphosphate, brine=saturated sodium chloride solution, Boc=tert-botoxycarbonyl, BSA=bovine serum albumin, DIAD=diisopropyl azodicarboxylate, DIPCDI=N,N'-diisopropylcarbodiimid, DMAP=4-dimethylaminopyridine, DMF=N,N-dimethylformamide, DTT=1,4-dithio-D,L-threitol, EDTA=ethylene diamine tetraacetic acid, Et=ethyl, EtOAc=ethyl acetate, EtOH=ethanol, Eu—PT66=LANCE europium-W1024-labelled anti-phosphotyrosine antibody (Perkin Elmer), FAK=Focal Adhesion Kinase, FRET=fluorescence resonance energy transfer, HEPES=N-2-hydroxyethyl-piperazine-N'-2-ethanesulfonic acid, HOAt=1-hydroxy-7-azabenzotriazole, Me=methyl, RT-PCR=reverse transcription polymerase chain reaction, SA-(SL)APC=Streptavidin conjugated to SuperLight allophycocyanin (Perkin Elmer), subst.=substituted, TBTU=O-(benzotriazol-1-yl)-N,N,N',N'-tetramethylammonium tetrafluoroborate, THF=tetrahydrofuran.

HPLC Conditions

Column: YMC CombiScreen ODS-A (5 um, 12 nm), 50×4.6 mm I.D.

Flow rate: 2.0 ml/min

Eluent: A) TFA/water (0.1/100), B) TFA/acetonitrile (0.1/100)

Gradient: 5-100% B (0-5 min)

Detection: UV at 215 nm

Example 1

Preparation of 7-[5-chloro-2-(2-methoxy-phenylamino)-pyrimidin-4-ylamino]-2-methyl-4-piperazin-1-yl-2,3-dihydro-isoindol-1-one

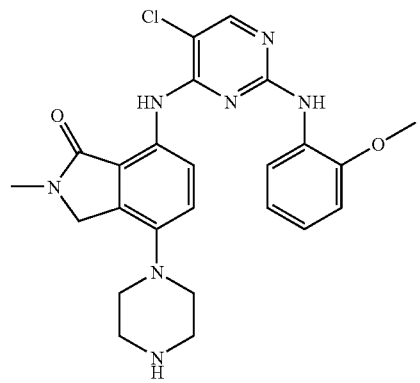

To a solution of 4-(2-methyl-7-nitro-1-oxo-2,3-dihydro-1H-isoindol-4-yl)-piperazine-1-carboxylic acid tert-butyl ester (2.79 g, 5.65 mmol) in 2-methoxyethanol (30 mL), o-anisidine (700 μL) and 4N hydrogen chloride in ethyl acetate (1.4 mL) are added and the mixture is stirred at 120° C. for 5 hours. The mixture is cooled to room temperature and then poured into saturated sodium hydrogen carbonate aq. The resulting pale yellow solids are collected by filtration. The solids are washed with methanol and ethyl acetate, and dried in vacuo to afford 7-[5-chloro-2-(2-methoxy-phenylamino)-pyrimidin-4-ylamino]-2-methyl-4-piperazin-1-yl-2,3-dihydro-isoindol-1-one as pale yellow solids (2.719) in quantitative yield. $R_f$=0.08 (MeOH/AcOEt=½). $^1$H-NMR (400 MHz, CDCl$_3$, δ, ppm): 3.05-3.01 (m, 8H), 3.21 (s, 3H), 3.92 (s, 3H), 4.38 (s, 2H), 6.92 (dd, 1H), 7.02-6.98 (m, 2H), 7.12 (d, 1H), 7.46 (s, 1H), 8.11 (s, 1H), 8.34 (dd, 1H), 8.67 (d, 1H), 10.5 (s, 1H).

The following 7-[5-chloro-2-(substituted phenylamino)-pyrimidin-4-ylamino]-2-methyl-4-piperazin-1-yl-2,3-dihydro-isoindol-1-one is prepared from 4-(2-methyl-7-nitro-1-oxo-2,3-dihydro-1H-isoindol-4-yl)-piperazine-1-carboxylic acid tert-butyl ester and the corresponding aniline following the procedure of Example 1.

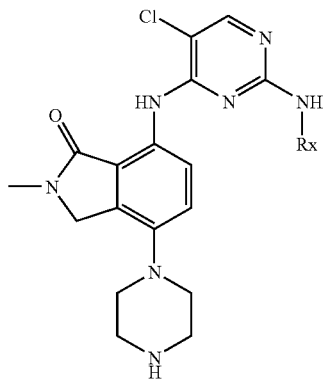

| Expl No. | Rx | MS | NMR (400 MHz), δ (ppm) |
|---|---|---|---|
| 2 | | 510, 512 | DMSO: 2.94-2.78 (m, 8 H), 3.07 (s, 3 H), 3.75 (s, 3 H), 3.82 (s, 3 H), 4.47 (s, 2 H), 6.57 (dd, 1 H), 6.68 (d, 1 H), 6.84 (d, 1 H), 7.42 (d, 1 H), 8.08 (s, 1 H), 8.30 (s, 2 H), 10.5 (s, 1 H). |

The following 7-[5-Chloro-2-(substituted phenylamino)-pyrimidin-4-ylamino]-4-(4-isopropyl-piperazin-1-yl)-2-methyl-2,3-dihydro-isoindol-1-ones are prepared from 7-(2,5-Dichloro-pyrimidin-4-ylamino)-4-(4-isopropyl-piperazin-1-yl)-2-methyl-2,3-dihydro-isoindol-1-one and the corresponding aniline following the procedure of Example 1.

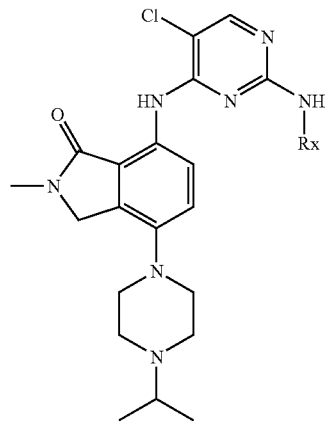

| Expl No. | Rx | MS | NMR (400 MHz), δ (ppm) |
|---|---|---|---|
| 3 | | 552 | DMSO: 1.01 (s, 3 H), 1.03 (s, 3 H), 2.60 (t, 4 H), 2.76-2.67 (m, 1 H), 2.99 (t, 4 H), 3.07 (s, 3 H), 3.75 (s, 3 H), 3.81 (s, 3 H), 4.48 (s, 2 H), 6.57 (dd, 1 H), 6.68 (d, 1 H), 6.86 (d, 1 H), 7.43 (d, 1 H), 8.09 (s, 1 H), 8.30 (s, 1 H), 8.40-8.30 (m, 1 H), 10.5 (s, 1 H). |

-continued
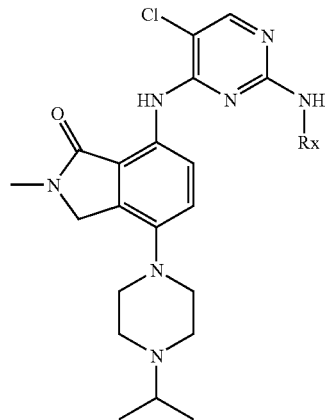
| Expl No. | Rx | MS | NMR (400 MHz), δ (ppm) |
|---|---|---|---|
| 4 | 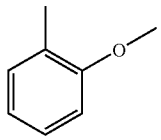 | 522, 524 | DMSO: 1.01 (s, 3 H), 1.03 (s, 3 H), 2.59 (t, 4 H), 2.77-2.68 (m, 1 H), 3.00 (t, 4 H), 3.08 (s, 3 H), 3.75 (s, 3 H), 3.81 (s, 3 H), 4.50 (s, 2 H), 7.00-6.95 (m, 1 H), 7.15-7.08 (m, 1 H), 7.80 (d, 1 H), 8.17 (s, 1 H), 8.31 (s, 1 H), 8.48-8.45 (m, 1 H), 10.6 (s, 1 H). |
| 5 | 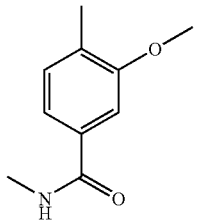 | 579, 581 | CDCl3: 1.11 (s, 3 H), 1.13 (s, 3 H), 2.72-2.70 (m, 4 H), 2.79-2.70 (m, 1 H), 3.05 (d, 3 H), 3.11-3.09 (m, 4 H), 3.22 (t, 4 H), 4.00 (s, 3 H), 4.39 (s, 2 H), 6.18-6.09 (m, 1 H), 7.17 (d, 1 H), 7.29-7.22 (m, 1 H), 7.49 (d, 1 H), 7.67 (s, 1 H), 8.14 (s, 1 H), 8.48 (d, 1 H), 8.64 (d, 1 H), 10.6 (s, 1 H). |
| 6 | 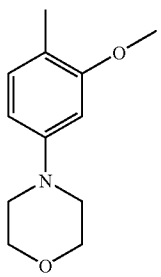 | 607 | CDCl3: 1.10 (s, 3 H), 1.12 (s, 3 H), 2.71-2.69 (m, 4 H), 2.77-2.69 (m, 1 H), 3.08-3.06 (m, 4 H), 3.16-3.14 (m, 4 H), 3.20 (s, 3 H), 3.89 (s, 3 H), 3.91-3.89 (m, 4 H), 4.37 (s, 2 H), 6.55-6.53 (m, 1 H), 6.55 (s, 1 H), 7.09 (d, 1 H), 7.16 (s, 1 H), 8.07 (s, 1 H), 8.10 (d, 1 H), 8.64 (d, 1 H), 10.5 (s, 1 H). |

-continued
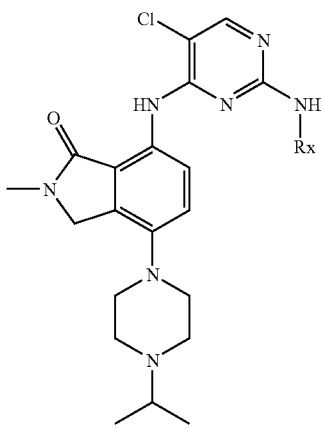
| Expl No. | Rx | MS | NMR (400 MHz), δ (ppm) |
|---|---|---|---|
| 7 | (3-methoxy-4-methylphenyl)-(3R)-N,N-dimethylpyrrolidin-3-amine | 634 | CDCl3: 1.11 (s, 3 H), 1.13 (s, 3 H), 2.04-1.92 (m, 1 H), 3.28-2.21 (m, 1 H), 2.34 (s, 6 H), 2.81-2.68 (m, 5 H), 2.97-2.86 (m, 1 H), 3.12-3.03 (m, 4 H), 3.20 (s, 3 H), 3.22-3.18 (m, 1 H), 3.40-3.34 (m, 1 H), 3.54-3.45 (m, 2 H), 3.87 (s, 3 H), 4.36 (s, 2 H), 6.16 (d, 1 H), 6.19 (dd, 1 H), 6.93 (s, 1 H), 7.05 (d, 1 H), 7.86 (d, 1 H), 8.04 (s, 1 H), 8.64 (d, 1 H), 10.5 (s, 1 H). |
| 8 | 4-[2-(4-methylpiperazin-1-yl)ethoxy]-2-methoxy-1-methylbenzene | 664 | CDCl3: 1.11 (s, 3 H), 1.13 (s, 3 H), 2.31 (s, 3 H), 2.57-2.45 (m, 4 H), 2.81-2.57 (m, 9 H), 2.86-2.83 (m, 2 H), 3.12-3.06 (m, 4 H), 3.21 (s, 3 H), 3.87 (s, 3 H), 4.14-4.11 (m, 2 H), 4.37 (s, 2 H), 6.50 (d, 1 H), 6.54 (dd, 1 H), 7.10 (d, 1 H), 7.13 (s, 1 H), 8.07 (s, 1 H), 8.08 (d, 1 H), 8.63 (d, 1 H), 10.5 (s, 1 H). |
| 9 | 1-(3-methoxy-4-methylphenyl)piperidin-4-ol | 621 | CDCl3: 1.11 (s, 3 H), 1.12 (s, 3 H), 1.83-1.72 (m, 2 H), 2.12-2.03 (m, 2 H), 2.73-2.69 (m, 4 H), 2.79-2.74 (m, 1 H), 2.96-2.90 (m, 2 H), 3.08-3.06 (m, 4 H), 3.20 (s, 3 H), 3.57-3.49 (m, 2 H), 3.87 (s, 3 H), 3.93-3.84 (m, 1 H), 4.36 (s, 2 H), 6.58-6.56 (m, 1 H), 6.58 (s, 1 H), 7.09 (d, 1 H), 7.12 (s, 1 H), 8.03 (d, 1 H), 8.06 (d, 1 H), 8.63 (d, 1 H), 10.5 (s, 1 H). |

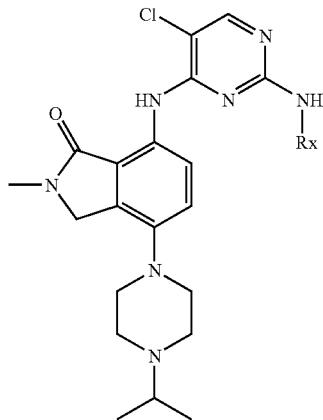
| Expl No. | Rx | MS | NMR (400 MHz), δ (ppm) |
|---|---|---|---|
| 10 | (3-methoxy-4-methylphenyl)-[(3S)-3-(dimethylamino)pyrrolidin-1-yl] | 634 | CDCl3: 1.11 (s, 3 H), 1.13 (s, 3 H), 2.04-1.92 (m, 1 H), 3.28-2.21 (m, 1 H), 2.34 (s, 6 H), 2.81-2.68 (m, 5 H), 2.97-2.86 (m, 1 H), 3.12-3.03 (m, 4 H), 3.20 (s, 3 H), 3.22-3.18 (m, 1 H), 3.40-3.34 (m, 1 H), 3.54-3.45 (m, 2 H), 3.87 (s, 3 H), 4.36 (s, 2 H), 6.16 (d, 1 H), 6.19 (dd, 1 H), 6.93 (s, 1 H), 7.05 (d, 1 H), 7.86 (d, 1 H), 8.04 (s, 1 H), 8.64 (d, 1 H), 10.5 (s, 1 H). |
| 11 | (3-methoxy-4-methylphenyl)-(4-piperidin-1-yl-piperidin-1-yl) | 688 | CDCl3: 1.11 (s, 3 H), 1.13 (s, 3 H), 1.53-1.42 (m, 2 H), 1.67-1.54 (m, 4 H), 1.84-1.71 (m, 2 H), 2.00-1.92 (m, 2 H), 2.48-2.37 (m, 1 H), 2.63-2.53 (m, 4 H), 2.80-2.72 (m, 1 H), 3.12-3.03 (m, 4 H), 3.20 (s, 3 H), 3.08-3.06 (m, 4 H), 3.20 (s, 3 H), 3.73-3.65 (m, 2 H), 3.89 (s, 3 H), 4.36 (s, 2 H), 6.58-6.55 (m, 1 H), 6.58 (s, 1 H), 7.08 (d, 1 H), 7.12 (s, 1 H), 8.02 (d, 1 H), 8.06 (s, 1 H), 8.63 (d, 1 H), 10.5 (s, 1 H). |

-continued
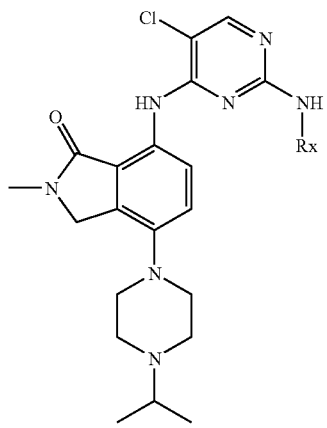
| Expl No. | Rx | MS | NMR (400 MHz), δ (ppm) |
|---|---|---|---|
| 12 | 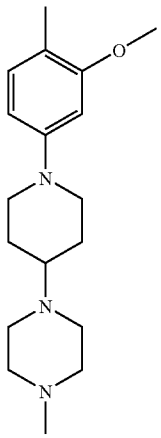 | 703 | CDCl3: 1.11 (s, 3 H), 1.13 (s, 3 H), 1.84-1.68 (m, 2 H), 2.03-1.94 (m, 2 H), 2.30 (s, 3 H), 2.45-2.33 (m, 2 H), 2.57-2.46 (m, 2 H), 2.81-2.62 (m, 12 H), 3.08-3.06 (m, 4 H), 3.20 (s, 3 H), 3.08-3.06 (m, 4 H), 3.20 (s, 3 H), 3.73-3.65 (m, 2 H), 3.88 (s, 3 H), 4.36 (s, 2 H), 6.55 (d, 1 H), 6.57 (s, 1 H), 7.09 (d, 1 H), 7.13 (s, 1 H), 8.04 (d, 1 H), 8.06 (s, 1 H), 8.64 (d, 1 H), 10.5 (s, 1 H). |
| 13 | 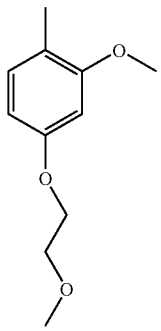 | 596 | DMSO: 1.01 (s, 3 H), 1.03 (s, 3 H), 2.65-2.58 (m, 4 H), 2.76-2.68 (m, 1 H), 3.04-2.98 (m, 4 H), 3.07 (s, 3 H), 3.34 (s, 3 H), 3.71-3.69 (m, 2 H), 3.74 (s, 3 H), 4.16-4.14 (m, 2 H), 4.47 (s, 2 H), 6.58 (dd, 1 H), 6.70 (d, 1 H), 7.40 (d, 1 H), 8.09 (s, 1 H), 8.31 (s, 1 H), 8.35-8.23 (m, 1 H), 10.5 (s, 1 H). |
| 14 | 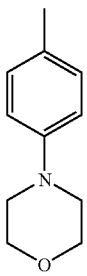 | 577 | CDCl3: 1.10 (s, 3 H), 1.12 (s, 3 H), 2.72-2.68 (m, 4 H), 2.81-2.73 (m, 1 H), 3.07-3.05 (m, 4 H), 3.17-3.14 (m, 4 H), 3.20 (s, 3 H), 3.91-3.89 (m, 4 H), 4.36 (s, 2 H), 6.77 (s, 1 H), 6.93 (dd, 1 H), 7.03 (d, 1 H), 7.44 (dd, 2 H), 8.05 (s, 1 H), 8.57 (d, 1 H), 10.6 (s, 1 H). |

The following 4-[1,4']Bipiperidinyl-1'-yl-7-[5-chloro-2-(substituted phenylamino)-pyrimidin-4-ylamino]-2-methyl-2,3-dihydro-isoindol-1-one are prepared from 4-[1,4']Bipiperidinyl-1'-yl-7-(2,5-dichloro-pyrimidin-4-ylamino)-2-methyl-2,3-dihydro-isoindol-1-one and the corresponding aniline following the procedure of Example 1.

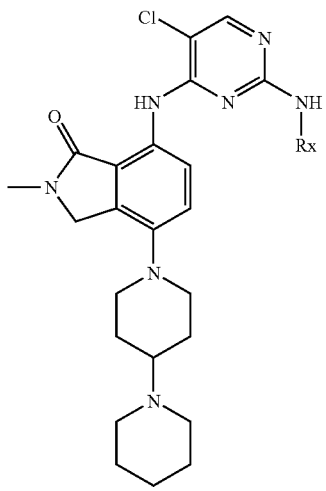

| Expl No. | Rx | MS | NMR (400 MHz), δ (ppm) |
|---|---|---|---|
| 15 | ![3-methoxy-4-methylphenyl-morpholine] | 647, 649 | CDCl3: 1.42-1.53 (m, 2 H), 1.54-1.69 (m, 4 H), 1.69-1.80 (m, 2 H), 1.92-2.01 (m, 2 H), 2.35-2.48 (m, 1 H), 2.53-2.66 (m, 4 H), 2.70-2.79 (m, 2 H), 3.11-3.18 (m, 4 H), 3.20 (s, 3 H), 3.29-3.37 (m, 2 H), 3.86-3.92 (m, 7 H), 4.35 (s, 2 H), 6.53-6.58 (m, 2 H), 7.05 (d, 1 H), 7.14 (s, 1 H), 8.06-8.11 (m, 2 H), 8.61 (d, 1 H), 10.51 (s, 1 H). |
| 16 | ![3-methoxy-4-methyl-phenyl-O-CH2CH2-O-CH3] | 636, 638 | CDCl3: 1.40-1.82 (m, 8 H), 1.92-2.05 (m, 2 H), 2.34-2.50 (m, 2 H), 2.50-2.66 (m, 3 H), 2.71-2.80 (m, 2 H), 3.20 (s, 3 H), 3.29-3.36 (m, 2 H), 3.48 (s, 3 H), 3.76-3.79 (m, 2 H), 3.86 (s, 3 H), 4.12-4.17 (m, 2 H), 4.35 (s, 2 H), 6.54 (dd, 1 H), 6.60 (d, 1 H), 7.05 (d, 1 H), 7.12 (s, 1 H), 8.07 (s, 1 H), 8.08 (d, 1 H), 8.59 (d, 1 H), 10.52 (s, 1 H). |
| 17 | ![2,4-dimethoxy-methylphenyl] | 592, 594 | CDCl3: 1.44-1.82 (m, 8 H), 1.96-2.04 (m, 2 H), 2.38-2.69 (m, 5 H), 2.71-2.79 (m, 2 H), 3.20 (s, 3 H), 3.30-3.38 (m, 2 H), 3.84 (s, 3 H), 3.88 (s, 3 H), 4.35 (s, 2 H), 6.51-6.55 (m, 2 H), 7.05 (d, 1 H), 7.10 (s, 1 H), 8.04-8.09 (m, 2 H), 8.59 (d, 1 H), 10.51 (s, 1 H). |
| 18 | ![2-methoxy-methylphenyl] | 562, 564 | CDCl3: 1.42-1.53 (m, 2 H), 1.58-1.81 (m, 6 H), 1.90-2.03 (m, 2 H), 1.90-2.03 (m, 2 H), 2.35-2.47 (m, 1 H), 2.49-2.65 (m, 4 H), 2.72-2.81 (m, 2 H), 3.21 (s, 3 H), 3.30-3.37 (m, 2 H), 3.92 (s, 3 H), 4.36 (s, 2 H), 6.90-6.94 (m, 1 H), 6.98-7.02 (m, 2 H), 7.09 (d, 1 H), 7.45 (s, 1 H), 8.11 (s, 1 H), 8.32-8.36 (m, 1 H), 8.64 (d, 1 H), 10.53 (s, 1 H). |

The following 7-[5-chloro-2-(substituted phenylamino)-pyrimidin-4-ylamino]-4-(4-hydroxy-piperidin-1-yl)-2-methyl-2,3-dihydro-isoindol-1-one are prepared from 7-(2,5-dichloro-pyrimidin-4-ylamino)-4-(4-hydroxy-piperidin-1-yl)-2-methyl-2,3-dihydro-isoindol-1-one and the corresponding aniline following the procedure of Example 1.

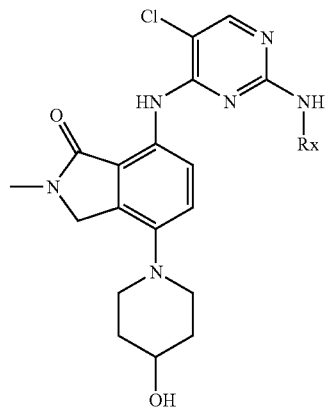

| Expl No. | Rx | MS | NMR (400 MHz), δ (ppm) |
|---|---|---|---|
| 19 | (4-morpholino-2-methoxy-tolyl) | 580, 582 | DMSO-d6: 1.48-1.59 (m, 2 H), 1.81-1.89 (m, 2 H), 2.72-2.80 (m, 2 H), 3.07 (s, 3 H), 3.15-3.25 (m, 6 H), 3.58-3.67 (m, 1 H), 3.73 (s, 3 H), 3.75-3.80 (m, 4 H), 4.46 (s, 2 H), 4.72 (d, 1 H), 6.54 (dd, 1 H), 6.69 (d, 1 H), 6.79-6.86 (m, 1 H), 7.28-7.35 (m, 1 H), 8.07 (s, 1 H), 8.18-8.30 (m, 1 H), 8.29 (s, 1 H), 10.47 (s, 1 H). |
| 20 | (2,4-dimethoxy-tolyl) | 525, 527 | DMSO-d6: 1.46-1.58 (m, 2 H), 1.81-1.91 (m, 2 H), 2.72-2.81 (m, 2 H), 3.07 (s, 3 H), 3.16-3.24 (m, 2 H), 3.59-3.67 (m, 1 H), 3.75 (s, 3 H), 3.81 (s, 3 H), 4.46 (s, 2 H), 4.70 (d, 1 H), 6.56 (dd, 1 H), 6.68 (d, 1 H), 6.85 (d, 1 H), 7.43 (d, 1 H), 8.08 (s, 1 H), 8.29 (s, 1 H), 8.28-8.36 (m, 1 H), 10.51 (s, 1 H). |

The following 7-[5-chloro-2-(substituted phenylamino)-pyrimidin-4-ylamino]-4-(R)-hexahydro-pyrazino[2,1-c][1,4]oxazin-8-yl-2-methyl-2,3-dihydro-isoindol-1-ones are prepared from 7-(2,5-dichloro-pyrimidin-4-ylamino)-4-(R)-hexahydro-pyrazino[2,1-c][1,4]oxazin-8-yl-2-methyl-2,3-dihydro-isoindol-1-one and the corresponding aniline following the procedure of Example 1.

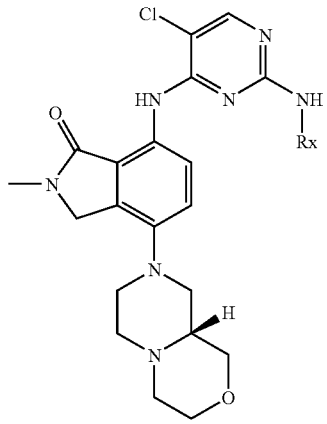

| Expl No. | Rx | MS | NMR (400 MHz), δ (ppm) |
|---|---|---|---|
| 21 | 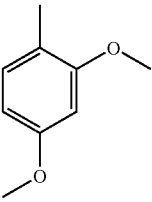 | 566, 568 | CDCl3: 2.42-2.64 (m, 4 H), 2.70-2.78 (m, 1 H), 2.85-2.92 (m, 1 H), 2.93-2.99 (m, 1 H), 3.01-3.12 (m, 1 H), 3.12-3.18 (m, 1 H), 3.21 (s, 3 H), 3.30-3.39 (m, 1 H), 3.69-3.80 (m, 2 H), 3.84 (s, 3 H), 3.87 (s, 3 H), 3.86-3.93 (m, 1 H), 4.36 (s, 2 H), 6.50-6.56 (m, 2 H), 7.05-7.12 (m, 2 H), 8.03-8.08 (m, 2 H), 8.62 (d, 1 H), 10.52 (s, 1 H). |
| 22 | 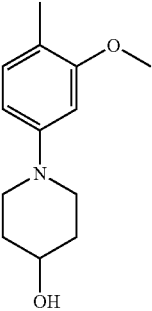 | 636, 638 | DMSO-d6: 1.48-1.60 (m, 2 H), 1.82-1.92 (m, 2 H), 2.21-2.44 (m, 4 H), 2.65-2.72 (m, 2 H), 2.77-2.92 (m, 4 H), 3.04-3.11 (m, 3 H), 3.13-3.27 (m, 2 H), 3.51-3.69 (m, 4 H), 3.69-3.83 (m, 5 H), 4.48 (s, 2 H), 4.72 (d, 1 H), 6.54 (dd, 1 H), 6.67 (d, 1 H), 6.74-6.84 (m, 1 H), 7.22-7.33 (m, 1 H), 8.08 (s, 1 H), 8.18-8.34 (m, 1 H), 8.28 (s, 1 H), 10.49 (s, 1 H). |

The following 7-[5-chloro-2-(substituted phenylamino)-pyrimidin-4-ylamino]-2-methyl-4-(4-piperazin-1-yl-piperidin-1-yl)-2,3-dihydro-isoindol-1-ones are prepared from 7-(2,5-dichloro-pyrimidin-4-ylamino)-2-methyl-4-(4-piperazin-1-yl-piperidin-1-yl)-2,3-dihydro-isoindol-1-one and the corresponding aniline following the procedure of Example 1.

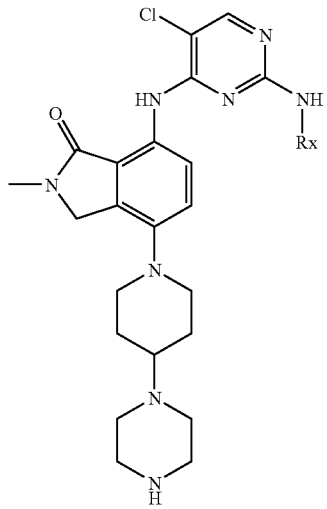

| Expl No. | Rx | MS | NMR (400 MHz), δ (ppm) |
|---|---|---|---|
| 23 | 2-methoxy-methylbenzene | 563, 565 | CDCl3: 1.64-1.76 (m, 2 H), 1.94-2.02 (m, 2 H), 2.34-2.43 (m, 1 H), 2.57-2.64 (m, 4 H), 2.73-2.82 (m, 2 H), 2.93-2.97 (m, 4 H), 3.21 (s, 3 H), 3.30-3.38 (m, 2 H), 3.92 (s, 3 H), 4.36 (m, 2 H), 6.90-6.92 (m, 1 H), 6.97-7.03 (m, 2 H), 7.09 (d, 1 H), 7.45 (s, 1 H), 8.11 (s, 1 H), 8.32-8.35 (m, 1 H), 8.65 (d, 1 H), 10.53 (s, 1 H). |
| 24 | 2,4-dimethoxy-methylbenzene | 593, 595 | CDCl3: 1.65-1.75 (m, 2 H), 1.94-2.02 (m, 2 H), 2.34-2.42 (m, 1 H), 2.57-2.64 (m, 4 H), 2.71-2.80 (m, 2 H), 2.93-2.97 (m, 4 H), 3.20 (s, 3 H), 3.30-3.35 (m, 2 H), 3.84 (s, 3 H), 3.88 (s, 3 H), 4.35 (m, 2 H), 6.51-6.57 (m, 2 H), 7.06 (d, 1 H), 7.10 (s, 1 H), 8.05-8.08 (m, 2 H), 8.60 (d, 1 H), 10.51 (s, 1 H). |
| 25 | 3-methoxy-4-methyl-(2-methoxyethoxy)benzene | 637 | DMSO-d6: 1.45-1.61 (m, 2 H), 1.82 (d, 2 H), 2.22-2.32 (m, 1 H), 2.35-2.47 (m, 4 H), 2.60-2.72 (m, 6 H), 3.07 (s, 3 H), 3.67-3.74 (m, 2 H), 3.74 (s, 3 H), 4.12-4.16 (m, 2 H), 4.46 (s, 2 H), 6.57 (dd, 1 H), 6.69 (d, 1 H), 6.83 (d, 1 H), 7.40 (d, 1 H), 8.08 (s, 1 H), 8.21-8.35 (m, 2 H), 10.50 (s, 1 H). |
| 26 | 3-methoxy-4-methyl-morpholinobenzene | 649 | CDCl3: 1.63-1.77 (m, 2 H), 1.93-2.01 (m, 2 H), 2.33-2.45 (m, 1 H), 2.57-2.68 (m, 4 H), 2.70-2.79 (m, 2 H), 2.94-2.99 (m, 4 H), 3.12-3.18 (m, 4 H), 3.21 (s, 3 H), 3.30-3.37 (m, 2 H), 3.87-3.92 (m, 4 H), 3.89 (s, 3 H), 4.35 (s, 2 H), 6.53-6.58 (m, 2 H), 7.06 (d, 1 H), 7.14 (s, 1 H), 8.06-8.11 (m, 2 H), 8.62 (d, 1 H), 10.51 (s, 1 H). |

The following 4-[4,4']Bipiperidinyl-1-yl-7-(5-chloro-2-substituted phenylamino-pyrimidin-4-ylamino)-2-methyl-2,3-dihydro-isoindol-1-ones are prepared from 1'-[7-(2,5-Dichloro-pyrimidin-4-ylamino)-2-methyl-1-oxo-2,3-dihydro-1#H!-isoindol-4-yl]-[4,4']bipiperidinyl-1-carboxylic acid tert-butyl ester and the corresponding aniline following the procedure of Example 1.

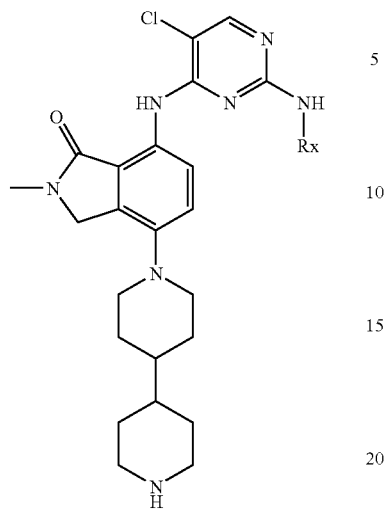
| Expl No. | Rx | MS | NMR (400 MHz), δ (ppm) |
|---|---|---|---|
| 27 | ![2-methoxytoluene] | 562 | CDCl3: 1.17-1.32 (m, 4 H), 1.35-1.48 (m, 2 H), 1.70-1.78 (m, 2 H), 1.80-1.89 (m, 2 H), 2.58-2.66 (m, 2 H), 2.66-2.75 (m, 2 H), 3.12-3.18 (m, 2 H), 3.21 (s, 3 H), 3.28-3.34 (m, 2 H), 3.92 (s, 3 H), 4.37 (s, 2 H), 6.89-6.94 (m, 1 H), 6.96-7.03 (m, 2 H), 7.09 (d, 1 H), 7.45 (s, 1 H), 8.11 (s, 1 H), 832-8.37 (m, 1 H), 8.64 (d, 1 H), 10.53 (s, 1 H). |
| 28 | ![2,4-dimethoxytoluene] | 592 | CDCl3: 1.18-1.31 (m, 4 H), 1.32-1.48 (m, 2 H), 1.68-1.78 (m, 2 H), 1.78-1.87 (m, 2 H), 2.56-2.64 (m, 2 H), 2.64-2.75 (m, 2 H), 3.11-3.18 (m, 2 H), 3.20 (s, 3 H), 3.26-3.33 (m, 2 H), 3.84 (s, 3 H), 3.88 (s, 3 H), 4.36 (s, 2 H), 6.51-6.56 (m, 2 H), 7.05 (d, 1 H), 7.10 (s, 1 H), 8.05-8.11 (m, 2 H), 8.60 (d, 1 H), 10.51 (s, 1 H). |
| 29 | ![substituted aryl ether] | 636 | CDCl3: 1.16-1.33 (m, 4 H), 1.35-1.48 (m, 2 H), 1.70-1.79 (m, 2 H), 1.79-1.88 (m, 2 H), 2.55-2.66 (m, 2 H), 2.66-2.75 (m, 2 H), 3.10-3.17 (m, 2 H), 3.20 (s, 3 H), 3.26-3.33 (m, 2 H), 3.48 (s, 3 H), 3.76-3.80 (m, 2 H), 3.86 (s, 3 H), 4.12-4.18 (m, 2 H), 4.36 (s, 2 H), 6.54 (dd, 1 H), 6.60 (d, 1 H), 7.05 (d, 1 H), 7.13 (s, 1 H), 8.05-8.11 (m, 2 H), 8.59 (d, 1 H), 10.52 (s, 1 H). |
| 30 | ![morpholinyl aryl] | 647 | CDCl3: 1.13-1.50 (m, 4 H), 1.41-1.91 (m, 6 H), 2.67-2.73 (m, 4 H), 3.15 (t, 4 H), 3.21 (s, 3 H), 3.26-3.32 (m, 4 H), 3.89 (s, 3 H), 3.89-3.91 (m, 4 H), 4.35 (s, 2 H), 6.55 (s, 1 H), 6.55-6.57 (m, 1 H), 7.05 (d, 1 H), 7.14 (s, 1 H), 8.07 (s, 1 H), 8.09 (dd, 1 H), 8.62 (d, 1 H), 10.5 (s, 1 H) |

The following 8-(5-chloro-2-substituted phenylamino-pyrimidin-4-ylamino)-2-methyl-5-piperazin-1-yl-3,4-dihydro-2H-isoquinolin-1-ones are prepared from 4-[8-(2,5-dichloro-pyrimidin-4-ylamino)-2-methyl-1-oxo-1,2,3,4-tetrahydro-isoquinolin-5-yl]-piperazine-1-carboxylic acid tert-butyl ester and the corresponding aniline following the procedure of Example 1.

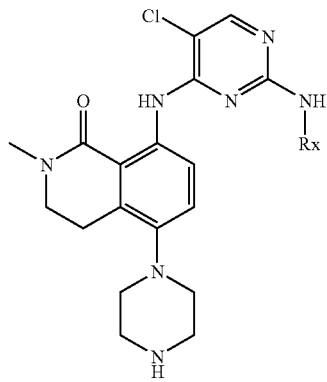

| Expl No. | Rx | MS | NMR (400 MHz), δ (ppm) |
|---|---|---|---|
| 31 | 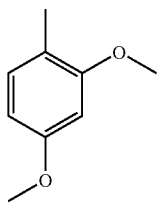 | 524 | CDCl3: 2.84-2.90 (m, 4 H), 3.01-3.09 (m, 6 H), 3.19 (s, 3 H), 3.47-3.54 (m, 2 H), 3.82 (s, 3 H), 3.86 (s, 3 H), 6.44-6.49 (m, 1 H), 6.51 (d, 1 H), 7.15 (s, 1 H), 7.20 (d, 1 H), 8.06 8s, 1 H), 8.13 (d, 1 H), 8.63 (d, 1 H), 12.12 (s, 1 H). |
| 32 | 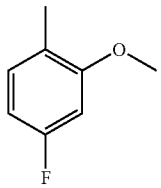 | 512 | CDCl3: 2.83-2.89 (m, 4 H), 3.01-309 (m, 6 H), 3.19 (s, 3 H), 3.49-3.54 (dd, 2 H), 3.88 (s, 3 H), 6.57-6.67 (m, 2 H), 7.21 (d, 1 H), 8.07 (s, 1 H), 8.26 (dd, 1 H), 8.56 (d, 1 H), 12.13 (s, 1 H). |
| 33 | 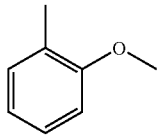 | 494 | DMSO-d6: 2.70-2.77 (m, 4 H), 2.81-2.88 (m, 4 H), 2.97 (dd, 2 H), 3.07 (s, 3 H), 3.50 (dd, 2 H), 3.82 (s, 3 H), 6.94 (ddd, 1 H), 7.03-7.09 (m, 2 H), 7.12 (d, 1 H), 7.90 (d, 1 H), 8.09 (s, 1 H), 8.15 (s, 1 H), 8.54 (d, 1 H), 12.30 (s, 1 H). |

-continued
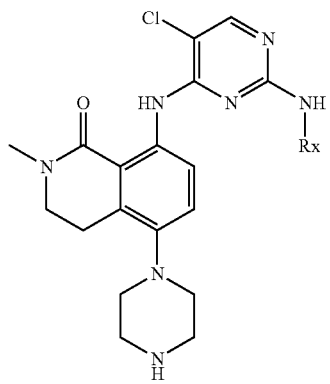
| Expl No. | Rx | MS | NMR (400 MHz), δ (ppm) |
|---|---|---|---|
| 34 | 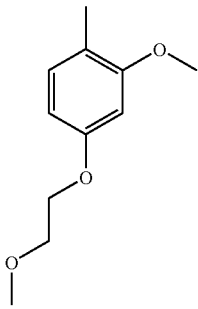 | 568 | DMSO-d6: 2.66-2.75 (m, 4 H), 2.79-2.87 (m, 4 H), 2.94 (dd, 2 H), 3.06 (s, 3 H), 3.33 (s, 3 H), 3.48 (dd, 2 H), 3.65-3.72 (m, 2 H), 3.76 (s, 3 H), 4.09-4.15 (m, 2 H), 6.53 (dd, 1 H), 6.68 (d, 1 H), 6.99 (d, 1 H), 7.45 (d, 1 H), 8.06 (s, 1 H), 8.13 (s, 1 H), 8.38-8.51 (m, 1 H), 12.23 (s, 1 H). |
| 35 | 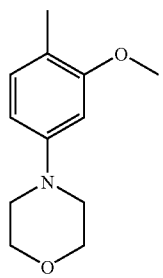 | 579 | CDCl3: 2.85-2.92 (m, 4 H), 3.01-3.09 (m, 6 H), 3.10-3.15 (m, 4 H), 3.19 (s, 3 H), 3.51 (dd, 2 H), 3.85-3.91 (m, 7 H), 6.49 (dd, 1 H), 6.53 (d, 1 H), 7.17-7.25 (m, 2 H), 8.06 (s, 1 H), 8.14 (d, 1 H), 8.64 (d, 1 H), 12.12 (s, 1 H). |
| 36 | 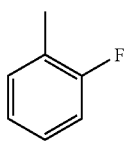 | 648 | CDCl3: 1.64-1.76 (m, 2 H), 1.93-2.00 (m, 2 H), 2.35-2.44 (m, 1 H), 2.57-2.68 (m, 4 H), 2.71-2.79 (m, 2 H), 2.94-2.99 (m, 4 H), 3.12-3.17 (m, 4 H), 3.21 (s, 3 H), 3.30-3.38 (m, 2 H), 3.86-3.92 (m, 7 H), 4.35 (s, 2 H), 6.53-6.58 (m, 2 H), 7.06 (d, 1 H), 7.14 (s, 1 H), 8.06-8.13 (m, 2 H), 8.62 (d, 1 H), 10.51 (s, 1 H). |

The following 8-[5-chloro-2-(substituted phenylamino)-pyrimidin-4-ylamino]-5-(4-isopropyl-piperazin-1-yl)-2-methyl-3,4-dihydro-2H-isoquinolin-1-ones are prepared from 8-(2,5-dichloro-pyrimidin-4-ylamino)-5-(4-isopropyl-piperazin-1-yl)-2-methyl-3,4-dihydro-2H-isoquinolin-1-one and the corresponding aniline following the procedure of Example 1

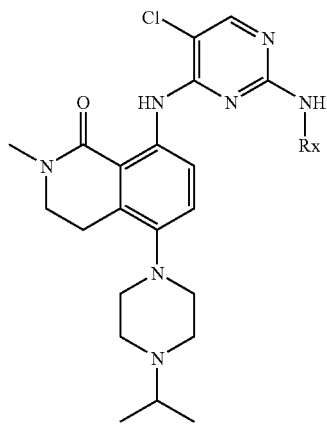

| Expl No. | Rx | Mass m/z | NMR (400 MHz) δ (ppm) |
|---|---|---|---|
| 37 | 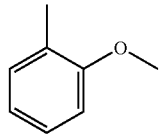 | 536, 538 | CDCl₃: 1.05-1.20 (m, 6 H), 2.62-2.85 (m, 5 H), 2.86-3.00 (m, 4 H), 3.05 (dd, 2 H), 3.19 (s, 3 H), 3.51 (dd, 2 H), 3.90 (s, 3 H), 6.87-7.00 (m, 3 H), 7.24-7.28 (m, 1 H), 7.49 (s, 1 H), 8.09 (s, 1 H), 8.34-8.39 (m, 1 H), 8.62 (d, 1 H), 12.11 (s, 1 H). |
| 38 | 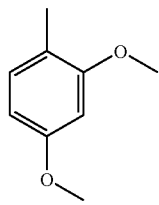 | 566, 568 | DMSO-d6: 1.01 (d, 6 H), 2.50-2.63 (m, 4 H), 2.70 (dq, 1 H), 2.76-2.83 (m, 4 H), 2.94 (dd, 2 H), 3.06 (s, 3 H), 3.48 (dd, 2 H), 3.76 (s, 3 H), 3.79 (s, 3 H), 6.53 (dd, 1 H), 6.66 (d, 1 H), 7.03 (d, 1 H), 7.48 (d, 1 H), 8.06 (s, 1 H), 8.12 (s, 1 H), 8.45-8.51 (m, 1 H), 12.25 (s, 1 H). |
| 39 | 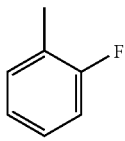 | 524, 526 | CDCl₃: 1.12 (d, 6 H), 2.63-2.80 (m, 5 H), 2.90-2.95 (m, 4 H), 3.05 (dd, 2 H), 3.19 (s, 3 H), 3.51 (dd, 2 H), 6.93-6.99 (m, 1 H), 7.04-7.12 (m, 3 H), 7.23 (d, 1 H), 8.10 (s, 1 H), 8.32-8.38 (m, 1 H), 8.56 (d, 1 H), 12.20 (s, 1 H). |

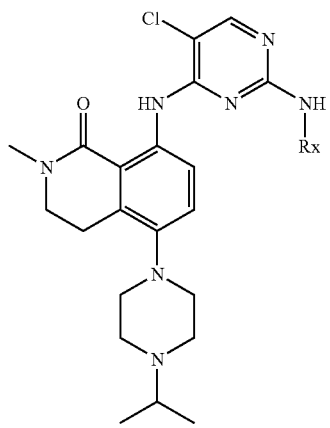

| Expl No. | Rx | Mass m/z | NMR (400 MHz) δ (ppm) |
|---|---|---|---|
| 40 | (4-methyl-3-methoxy-phenyl with O-CH2-CH2-O-CH3 at 4-position) | 610, 612 | CDCl₃: 1.13 (d, 6 H), 2.60-2.99 (m, 9 H), 3.04 (dd, 2 H), 3.19 (s, 3 H), 3.47 (s, 3 H), 3.50 (dd, 2 H), 3.75-3.78 (m, 2 H), 3.85 (s, 3 H), 4.11-4.14 (m, 2 H), 6.47 (dd, 1 H), 6.58 (d, 1 H), 7.18 (s, 1 H), 7.23 (d, 1 H), 8.05 (s, 1 H), 8.14 (d, 1 H), 8.63 (d, 1 H), 12.13 (s, 1 H). |
| 41 | (4-methyl-3-methoxy-phenyl with morpholinyl) | 621, 623 | DMSO-d6: 1.02 (d, 6 H), 2.53-2.64 (m, 4 H), 2.71 (dq, 1 H), 2.75-2.83 (m, 4 H), 2.93 (dd, 2 H), 3.06 (s, 3 H), 3.11-3.18 (m, 4 H), 3.47 (dd, 2 H), 3.72-3.80 (m, 7 H), 6.51 (dd, 1 H), 6.67 (d, 1 H), 7.01 (d, 1 H), 7.36 (d, 1 H), 8.05 (s, 1 H), 8.13 (s, 1 H), 8.40-8.48 (m, 1 H), 12.21 (s, 1 H). |
| 42 | (2-fluoro-6-methyl-phenyl) | 524 | CDCl3: 1.12 (d, 6 H), 2.63-2.80 (m, 5 H), 2.90-2.95 (m, 4 H), 3.05 (dd, 2 H), 3.19 (s, 3 H), 3.51 (dd, 2 H), 6.93-6.99 (m, 1 H), 7.04-7.12 (m, 3 H), 7.23 (d, 1 H), 8.10 (s, 1 H), 8.32-8.38 (m, 1 H), 8.56 (d, 1 H), 12.20 (s, 1 H). |

The following 8-(5-chloro-2-substituted phenylamino-pyrimidin-4-ylamino)-2-methyl-5-(4-piperazin-1-yl-piperidin-1-yl)-3,4-dihydro-2H-isoquinolin-1-ones are prepared from 4-{1-[8-(2,5-Dichloro-pyrimidin-4-ylamino)-2-methyl-1-oxo-1,2,3,4-tetrahydro-isoquinolin-5-yl]-piperidin-4-yl}-piperazine-1-carboxylic acid tert-butyl ester and the corresponding aniline following the procedure of Example 1.

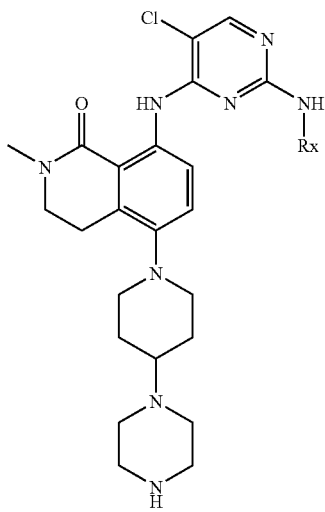
| Expl No. | Rx | MS | NMR (400 MHz), δ (ppm) |
|---|---|---|---|
| 43 | 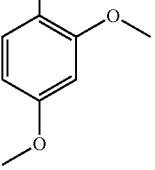 | 607 | CDCl3: 1.64-1.77 (m, 2 H), 1.88-2.03 (m, 2 H), 2.31-2.40 (m, 1 H), 2.56-2.74 (m, 6 H), 2.93-3.00 (m, 4 H), 302 (dd, 2 H), 3.09 (br. d., 2 H), 3.19 (s, 3 H), 3.50 (dd, 2 H), 3.81 (s, 3 H), 3.86 (s, 3 H), 6.46 (dd, 1 H), 6.51 (d, 1 H), 7.15 (d, 1 H), 7.19 (s, 1 H), 8.05 (s, 1 H), 8.13 (d, 1 H), 8.58 (d, 1 H), 12.08 (s, 1 H). |
| 44 | 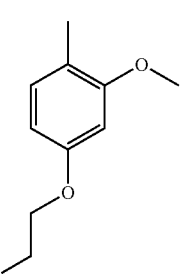 | 651 | CDCl3: 1.65-1.76 (m, 2 H), 1.91-2.00 (m, 2 H), 2.30-2.41 (m, 1 H), 2.52-2.65 (m, 4 H), 2.65-2.75 (m, 2 H), 2.88-2.98 (m, 4 H), 3.02 (dd, 2 H), 3.03-3.13 (m, 2 H), 3.19 (s, 3 H), 3.47 (s, 3 H), 3.50 (dd, 2 H), 3.73-3.79 (m, 2 H), 3.85 (s, 3 H), 4.07-4.16 (m, 2 H), 6.47 (dd, 1 H), 6.57 (d, 1 H), 7.14-7.21 (m, 2 H), 8.05 (s, 1 H), 8.13 (d, 1 H), 8.58 (d, 1 H), 12.09 (s, 1 H). |
| 45 | 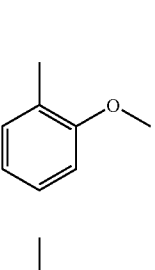 | 577 | CDCl3: 1.62-1.78 (m, 2 H), 1.92-2.01 (m, 2 H), 2.31-2.42 (m, 1 H), 2.57-2.66 (m, 4 H), 2.66-2.76 (m, 2 H), 2.93-3.00 (m, 4 H), 3.01 (dd, 2 H), 3.05-3.12 (m, 2 H), 3.19 (s, 3 H), 3.51 (dd, 2 H), 3.90 (s, 3 H), 6.86-7.00 (m, 3 H), 7.21 (d, 1 H), 7.50 (s, 1 H), 8.09 (s, 1 H), 8.38 (dd, 1 H), 8.59 (d, 1 H), 12.09 (s, 1 H). |
| 46 | 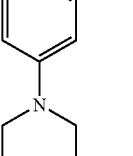 | 682 | CDCl3: 1.64-1.78 (m, 2 H), 1.90-2.10 (m, 2 H), 2.29-2.40 (m, 1 H), 2.52-2.64 (m, 4 H), 2.64-2.74 (m, 2 H), 2.90-2.97 (m, 4 H), 2.97-3.04 (m, 2 H), 3.04-3.15 (m, 6 H), 3.19 (s, 3 H), 3.46-3.53 (m, 2 H), 3.84-3.93 (m, 7 H), 6.48 (dd, 1 H), 6.53 (d, 1 H), 7.14-7.22 (m, 2 H), 8.05 (s, 1 H), 8.13 (d, 1 H), 8.58 (d, 1 H), 12.06 (s, 1 H). |

Example 47

Preparation of 7-[5-chloro-2-(2-methoxy-phenylamino)-pyridin-4-ylamino]-2-methyl-4-(4-methyl-piperazin-1-yl)-2,3-dihydro-isoindol-1-one

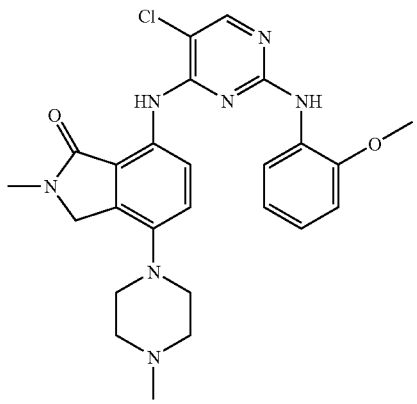

To a solution of 7-[5-chloro-2-(2-methoxy-phenylamino)-pyrimidin-4-ylamino]-2-methyl-4-piperazin-1-yl-2,3-dihydro-isoindol-1-one (2.0 g, 4.17 mmol) in dichloroethane (50 mL), formaldehyde (380 µL, 5.0 mmol) is added and the mixture is stirred at room temperature for 1.5 hours. After addition of triacetoxy sodium borohydride (1.06 g, 5.0 mmol), the mixture is stirred at room temperature for 1.5 hours. The mixture is poured into 1N sodium hydroxide and stirred at room temperature for 10 min, then extracted twice with dichloromethane. The organic layer is successively washed with water and brine, dried over magnesium sulfate, and evaporated in vacuo. The resulting solids are washed with methanol and ethyl acetate to give 7-[5-Chloro-2-(2-methoxy-phenylamino)-pyrimidin-4-ylamino]-2-methyl-4-(4-methyl-piperazin-1-yl)-2,3-dihydro-isoindol-1-one (1.2 g) as pale yellow solids in 58% yield. Rf=0.30 (MeOH/AcOEt=½). ESI-MS m/z: 494 [MH]$^+$. $^1$H-NMR (400 MHz, CDCl$_3$, δ, ppm): 2.38 (s, 3H), 2.66-2.57 (m, 4H), 3.09-3.07 (m, 4H), 3.21 (s, 3H), 3.92 (s, 3H), 4.37 (s, 2H), 6.92 (dd, 1H), 7.03-6.96 (m, 2H), 7.13 (d, 1H), 7.45 (s, 1H), 8.11 (s, 1H), 8.33 (dd, 1H), 8.67 (d, 1H), 10.5 (s, 1H).

The following 7-[5-chloro-2-(substituted phenylamino)-pyrimidin-4-ylamino]-2-methyl-4-(4-methyl-piperazin-1-yl)-2,3-dihydro-isoindol-1-ones are prepared from 7-[5-Chloro-2-(substituted phenylamino)-pyrimidin-4-ylamino]-2-methyl-4-piperazin-1-yl-2,3-dihydro-isoindol-1-ones following the procedure of Example 8.

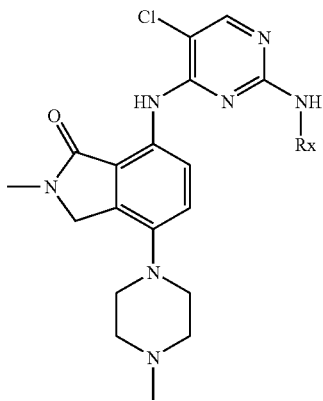

| Expl No. | Rx | MS | NMR (400 MHz), δ (ppm) |
|---|---|---|---|
| 48 | ![2-methyl-4,6-dimethoxyphenyl] | 524, 526 | DMSO: 2.24 (s, 3 H), 2.51-2.47 (m, 4 H), 2.99 (t, 4 H), 3.07 (s, 3 H), 3.75 (s, 3 H), 3.81 (s, 3 H), 4.47 (s, 2 H), 6.57 (dd, 1 H), 6.68 (d, 1 H), 6.85 (d, 1 H), 7.43 (d, 1 H), 8.09 (s, 1 H), 8.30 (s, 2 H), 10.5 (s, 1 H). |

The following 7-[5-chloro-2-(substituted phenylamino)-pyrimidin-4-ylamino]-2-methyl-4-[4-(4-methyl-piperazin-1-yl)-piperidin-1-yl]-2,3-dihydro-isoindol-1-ones are prepared from 7-[5-chloro-2-(2-substituted-phenylamino)-pyrimidin-4-ylamino]-2-methyl-4-(4-piperazin-1-yl-piperidin-1-yl)-2,3-dihydro-isoindol-1-ones following the procedure of Example 8.

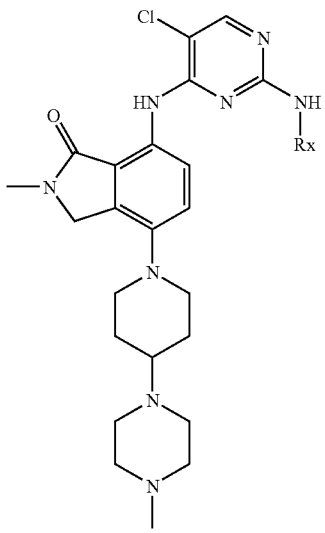

| Expl No. | Rx | MS | NMR (400 MHz), δ (ppm) |
|---|---|---|---|
| 49 | 2-methoxy-methylphenyl | 577, 579 | CDCl3: 1.64-1.74 (m, 2 H), 1.95-2.04 (m, 2 H), 2.34 (s, 3 H), 2.35-2.82 (m, 11 H), 3.21 (s, 3 H), 3.30-3.38 (m, 2 H), 3.91 (s, 3 H), 4.35 (s, 2 H), 6.90-6.93 (m, 1 H), 6.97-7.02 (m, 2 H), 7.09 (d, 1 H), 7.45 (s, 1 H), 8.11 (s, 1 H), 8.33-8.35 (m, 1 H), 8.65 (d, 1 H), 10.53 (s, 1 H). |
| 50 | 2,4-dimethoxy-methylphenyl | 607, 609 | CDCl3: 1.65-1.76 (m, 2 H), 1.94-2.04 (m, 2 H), 2.32 (s, 3 H), 2.35-2.82 (m, 11 H), 3.20 (s, 3 H), 3.30-3.34 (m, 2 H), 3.84 (s, 3 H), 3.87 (s, 3 H), 4.34 (m, 2 H), 6.51-6.56 (m, 2 H), 7.06 (d, 1 H), 7.10 (s, 1 H), 8.05-8.08 (m, 2 H), 8.60 (d, 1 H), 10.51 (s, 1 H). |
| 51 | 4-(2-methoxyethoxy)-2-methoxy-methylphenyl | 651 | DMSO-d6: 1.47-1.59 (m, 2 H), 1.80-1.87 (m, 2 H), 2.15 (s, 3 H), 2.21-2.38 (m, 5 H)m 2.62-2.71 (m, 2 H), 3.07 (s, 3 H), 3.34 (s, 3 H), 3.67-3.73 (m, 2 H), 3.74 (s, 3 H), 4.12-4.16 (m, 2 H), 4.46 (s, 2 H), 6.56 (dd, 1 H), 6.69 (d, 1 H), 6.83 (d, 1 H), 7.40 (d, 1 H), 8.08 (s, 1 H), 8.22-8.34 (m, 2 H), 10.50 (s, 1 H). |
| 52 | 4-morpholino-2-methoxy-methylphenyl | 662 | CDCl3: 1.63-1.77 (m, 2 H), 1.95-2.03 (m, 2 H), 2.33 (s, 3 H), 2.36-2.82 (m, 11 H), 3.12-3.18 (m, 4 H), 3.21 (s, 3 H), 3.29-3.36 (m, 2 H), 3.85-3.95 (m, 7 H), 4.35 (s, 2 H), 6.53-6.58 (m, 2 H), 7.06 (d, 1 H), 8.06-8.12 (m, 2 H), 8.61 (d, 1 H), 10.51 (s, 1 H). |

The following 7-(5-chloro-2-substituted phenylamino-pyrimidin-4-ylamino)-2-methyl-4-(1'-methyl-[4,4']bipiperidinyl-1-yl)-2,3-dihydro-isoindol-1-ones are prepared from 4-[4,4']bipiperidinyl-1-yl-7-(5-chloro-2-substituted phenylamino-pyrimidin-4-ylamino)-2-methyl-2,3-dihydro-isoindol-1-ones following the procedure of Example 8.

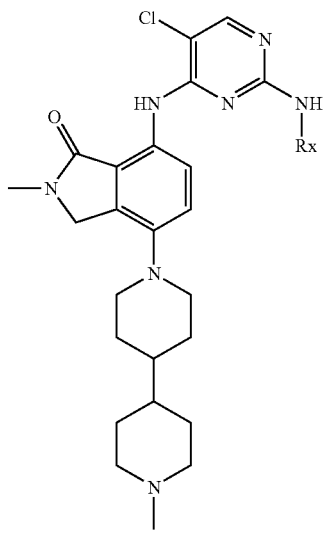

| Expl No. | Rx | MS | NMR (400 MHz), δ (ppm) |
|---|---|---|---|
| 53 | 2-methoxyphenyl (methyl) | 576 | CDCl3: 1.08-1.19 (m, 1 H), 1.19-1.31 (m, 1 H), 1.31-1.48 (m, 4 H), 1.70-1.78 (m, 2 H), 1.80-1.98 (m, 4 H), 2.29 (s, 3 H), 2.66-2.75 (m, 2 H), 2.87-2.98 (m, 2 H), 3.92 (s, 3 H), 4.36 (s, 2 H), 6.90-6.94 (m, 1 H), 6.97-7.04 (m, 2 H), 7.09 (d, 1 H), 7.45 (s, 1 H), 8.11 (s, 1 H), 8.32-8.36 (m, 1 H), 8.65 (d, 1 H), 10.53 (s, 1 H). |
| 54 | 2,4-dimethoxyphenyl (methyl) | 606 | CDCl3: 1.07-1.18 (m, 1 H), 1.18-1.29 (m, 1 H), 1.21-1.47 (m, 4 H), 1.70-1.77 (m, 2 H), 1.78-1.88 (m, 2 H), 1.88-1.96 (m, 2 H), 2.28 (s, 3 H), 2.65-2.74 (m, 2 H), 2.88-2.95 (m, 2 H), 3.20 (s, 3 H), 3.26-3.33 (m, 2 H), 3.84 (s, 3 H), 3.87 (s, 3 H), 4.35 (s, 2 H), 6.51-6.56 (m, 2 H), 7.05 (d, 1 H), 7.10 (s, 1 H), 8.04-8.10 (m, 2 H), 8.59 (d, 1 H), 10.51 (s, 1 H). |
| 55 | 2-methoxy-4-(2-methoxyethoxy)phenyl (methyl) | 650 | CDCl3: 1.07-1.18 (m, 1 H), 1.18-1.30 (m, 1 H), 1.31-1.48 (m, 4 H), 1.70-1.79 (m, 2 H), 1.79-1.87 (m, 2 H), 1.87-1.98 (m, 2 H), 2.29 (s, 3 H), 2.65-2.75 (m, 2 H), 2.87-2.97 (m, 2 H), 3.20 (s, 3 H), 3.25-3.33 (m, 2 H), 3.47 (s, 3 H), 3.75-3.79 (m, 2 H), 3.86 (s, 3 H), 4.12-4.17 (m, 2 H), 4.35 (s, 2 H), 6.54 (dd, 1 H), 6.60 (d, 1 H), 7.06 (d, 1 H), 7.12 (s, 1 H), 8.07 (s, 1 H), 8.09 (d, 1 H), 8.60 (d, 1 H), 10.52 (s, 1 H). |
| 56 | 2-methoxy-4-morpholinophenyl (methyl) | 661 | CDCl3: 1.13-1.50 (m, 4 H), 1.41-1.91 (m, 6 H), 2.04-2.20 (m, 2 H), 2.40 (s, 3 H), 2.70 (t, 2 H), 3.03-3.13 (m, 2 H), 3.15 (t, 4 H), 3.20 (s, 3 H), 3.30 (d, 2 H), 3.89 (s, 3 H), 3.89-3.91 (m, 4 H), 4.35 (s, 2 H), 6.55 (s, 1 H), 6.55-6.57 (m, 1 H), 7.05 (d, 1 H), 7.14 (s, 1 H), 8.07 (s, 1 H), 8.09 (d, 1 H), 8.62 (d, 1 H), 10.5 (s, 1 H) |

The following 8-(5-chloro-2-substituted phenylamino-pyrimidin-4-ylamino)-2-methyl-5-(4-methyl-piperazin-1-yl)-3,4-dihydro-2H-isoquinolin-1-ones are prepared from 8-(5-chloro-2-substituted phenylamino-pyrimidin-4-ylamino)-2-methyl-5-piperazin-1-yl-3,4-dihydro-2H-isoquinolin-1-ones following the procedure of Example 8.

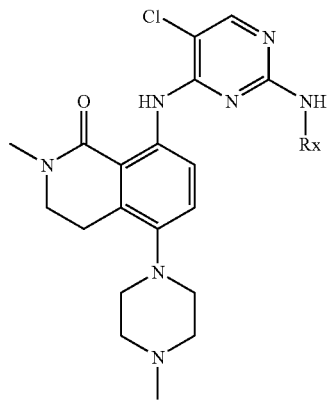

| Expl No. | Rx | MS | NMR (400 MHz), δ (ppm) |
|---|---|---|---|
| 57 | 4-morpholino-3-methoxy-phenyl (methyl at 1-position) | 593 | CDCl3: 2.39 (s, 3 H), 2.48-2.73 (m, 4 H), 2.87-2.97 (m, 4 H), 3.03 (dd, 2 H), 3.09-3.14 (m, 4 H), 3.19 (s, 3 H), 3.50 (dd, 2 H), 3.85-3.90 (m, 7 H), 6.49 (dd, 1 H), 6.53 (d, 1 H), 7.19 (s, 1 H), 7.22 (d, 1 H), 8.06 (s, 1 H), 8.14 (d, 1 H), 8.65 (d, 1 H), 12.12 (s, 1 H). |
| 58 | 2,4-dimethoxy-phenyl (methyl) | 538 | CDCl3: 2.40 (s, 3 H), 2.49-2.75 (m, 4 H), 2.85-2.98 (m, 4 H), 3.00-3.07 (m, 2 H), 3.19 (s, 3 H), 3.47-3.54 (m, 2 H), 3.81 (s, 3 H), 3.86 (s, 3 H), 6.46 (dd, 1 H), 6.51 (d, 1 H), 7.15 (s, 1 H), 7.22 (d, 1 H), 8.06 (s, 1 H), 8.12 (d, 1 H), 8.63 (d, 1 H), 12.12 (s, 1 H). |
| 59 | 4-fluoro-2-methoxy-phenyl (methyl) | 526 | CDCl3: 2.39 (s, 3 H), 2.48-2.69 (m, 4 H), 2.90-2.97 (m, 4 H), 3.04 (dd, 2 H), 3.19 (s, 3 H), 3.51 (dd, 2 H), 3.88 (s, 3 H), 6.57-6.67 (m, 2 H), 7.23 (d, 1 H), 8.07 (s, 1 H), 8.26 (dd, 1 H), 8.56 (d, 1 H), 12.12 (s, 1 H). |
| 60 | 2-methoxy-phenyl (methyl) | 508 | DMSO-d6: 2.24 (s, 3 H), 2.78-2.86 (m, 4 H), 2.96 (dd, 2 H), 3.07 (s, 3 H), 3.50 (dd, 2 H), 3.82 (s, 3 H), 6.94 (ddd, 1 H), 7.04-7.09 (m, 2 H), 7.14 (d, 1 H), 7.90 (d, 1 H), 8.09 (s, 1 H), 8.15 (s, 1 H), 8.54 (d, 1 H), 12.31 (s, 1 H). |
| 61 | 4-(2-methoxyethoxy)-2-methoxy-phenyl (methyl) | 582 | DMSO-d6: 2.24 (s, 3 H), 2.75-2.86 (m, 4 H), 2.94 (dd, 2 H), 3.06 (s, 3 H), 3.46 (s, 3 H), 3.48 (dd, 2 H), 3.66-3.71 (m, 2 H), 3.75 (s, 3 H), 4.09-4.15 (m, 2 H), 6.54 (dd, 1 H), 6.68 (d, 1 H), 7.02 (d, 1 H), 7.46 (d, 1 H), 8.06 (s, 1 H), 8.13 (s, 1 H), 8.38-8.49 (m, 1 H), 12.24 (s, 1 H). |

-continued

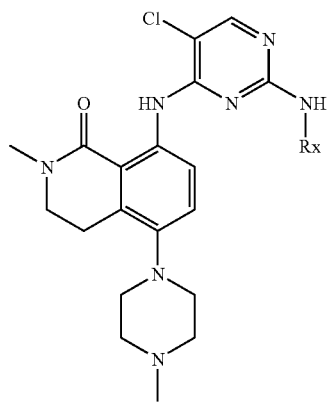

| Expl No. | Rx | MS | NMR (400 MHz), δ (ppm) |
|---|---|---|---|
| 62 | (2-fluoro-6-methylphenyl) | Rf: 0.62 (MeOH: CH2Cl2 = 1:9) | DMSO-d6: 2.24 (s, 3 H), 2.43-2.53 (m, 4 H), 2.77-2.83 (m, 4 H), 2.95 (t, 2 H), 3.07 (s, 3 H), 3.48 (t, 2 H), 7.04 (d, 1 H), 7.15-7.23 (m, 2 H), 7.24-7.33 (m, 1 H), 7.6-7.7 (m, 1 H), 1 H), 8.14 (s, 1 H), 8.53 (d, 1 H), 9.0 (s, 1 H), 12.4 (s, 1 H) |

The following 8-(5-chloro-2-substituted phenylamino-pyrimidin-4-ylamino)-2-methyl-5-[4-(4-methyl-piperazin-1-yl)-piperidin-1-yl]-3,4-dihydro-2H-isoquinolin-1-ones are prepared from 8-(5-chloro-2-substituted phenylamino-pyrimidin-4-ylamino)-2-methyl-5-(4-piperazin-1-yl-piperidin-1-yl)-3,4-dihydro-2H-isoquinolin-1-one following the procedure of Example 8.

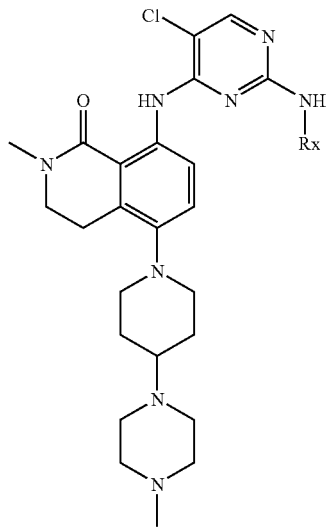

| Expl No. | Rx | MS | NMR (400 MHz), δ (ppm) |
|---|---|---|---|
| 63 | (2,4-dimethoxy-6-methylphenyl) | 621 | CDCl3: 1.64-1.769 (m, 2 H), 1.96 (br. d., 2 H), 2.31 (s, 3 H), 2.30-2.41 (m, 1 H), 2.40-2.57 (m, 4 H), 2.58-2.76 (m, 6 H), 3.01 (dd, 2 H), 3.18 (s, 3 H), 3.49 (dd, 2 H), 3.81 (s, 3 H), 3.86 (s, 3 H), 6.46 (dd, 1 H), 6.51 (d, 1 H), 7.16 (d, 1 H), 7.19 (s, 1 H), 8.05 (s, 1 H), 8.13 (d, 1 H), 8.58 (d, 1 H), 12.08 (s, 1 H). |

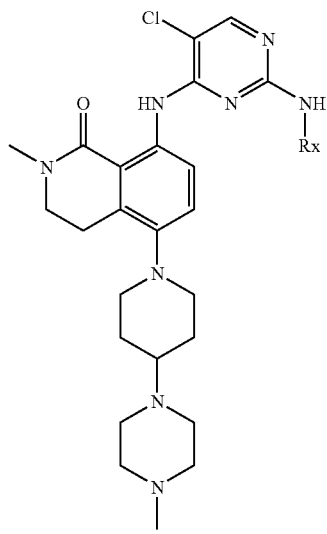
| Expl No. | Rx | MS | NMR (400 MHz), δ (ppm) |
|---|---|---|---|
| 64 | 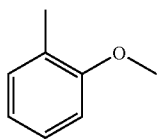 | 665 | CDCl3: 1.62-1.77 (m, 2 H), 1.92-2.01 (m, 2 H), 2.32 (s, 3 H), 2.31-2.43 (m, 1 H), 2.43-2.60 (m, 4 H), 2.60-2.78 (m, 6 H), 3.01 (dd, 2 H), 3.04-3.12 (m, 2 H), 3.18 (s, 3 H), 3.47 (s, 3 H), 3.50 (dd, 2 H), 3.73-3.79 (m, 2 H), 3.85 (s, 3 H), 4.09-4.14 (m, 2 H), 6.47 (dd, 1 H), 6.57 (d, 1 H), 7.17 (dd, 1 H), 8.05 8s, 1 H), 8.13 d, 1 H), 8.58 (d, 1 H), 12.09 (s, 1 H). |
| 65 | 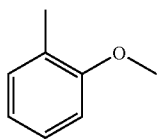 | 591 | CDCl3: 1.65-1.77 (m, 2 H), 1.93-2.02 (m, 2 H), 2.32 (s, 3 H), 2.32-2.43 (m, 1 H), 2.43-2.59 (m, 4 H), 2.60-2.79 (m, 6 H), 3.02 (dd, 2 H), 3.05-3.12 (m, 2 H), 3.51 (dd, 2 H), 3.90 (s, 3 H), 6.86-6.99 (m, 3 H), 7.20 (d, 1 H), 7.50 (s, 1 H), 8.08 (s, 1 H), 8.38 (dd, 1 H), 8.59 (d, 1 H), 12.09 (s, 1 H). |
| 66 | 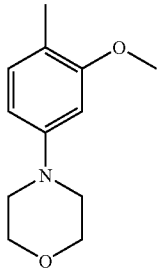 | 676 | CDCl3: 1.65-1.77 (m, 2 H), 1.92-2.01 (m, 2 H), 2.31 (s, 3 H), 2.31-2.42 (m, 1 H), 2.42-2.59 (m, 4 H), 2.59-2.78 (m, 6 H), 3.01 (t, 2 H), 3.04-3.14 (m, 6 H), 3.19 (s, 3 H), 3.50 (t, 2 H), 3.84-3.92 (m, 7 H), 6.48 (dd, 1 H), 6.53 (d, 1 H), 7.14-7.21 (m, 2 H), 8.05 (s, 1 H), 8.14 (d, 1 H), 8.58 (d, 1 H), 12.06 (s, 1 H). |

Example 11

Preparation of 4-fluoro-2-methyl-7-nitro-2,3-dihydro-isoindol-1-one

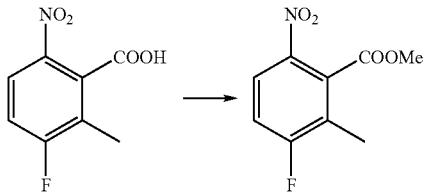

To a solution of 3-fluoro-2-methyl-6-nitro-benzoic acid in 200 mL of methanol, Cs$_2$CO$_3$ (4.34 g, 13.3 mmol) is added and stirred at the room temperature. The solution is concentrated under reduced pressure then the resulting yellow solids are suspended in 26 ml of DMF. Iodomethane (1.7 ml 26.6 mol) is added at 0° C. and stirred at the room temperature for 30 min. Water is added to the solution and extracted with ethyl acetate. The organic layer is washed with H$_2$O followed by brine, dried over Na$_2$SO$_4$, filtered and evaporated in vacuo to afford 3-fluoro-2-methyl-6-nitro-benzoic acid methyl ester (5.70 g) as yellow oil in quantitative yield. $^1$H-NMR (400 MHz, δ, ppm) CDCl3: 2.30 (d, 3H), 3.99 (s, 3H), 7.22 (dd, 1H), 8.07 (dd, 1H).

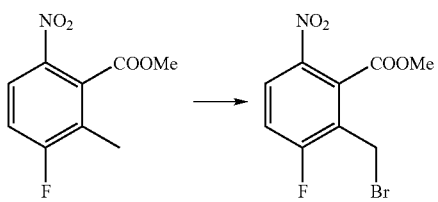

To a suspension of 3-fluoro-2-methyl-6-nitro-benzoic acid methyl ester (6.1 g, 28.6 mmol) and N-bromosuccinimide in 70 mL of CCl$_4$ is added 2,2'-azobisisobutyronitrile at room temperature under nitrogen atmosphere. The reaction mixture is stirred at 85° C. for 6 hours under N$_2$, then cooled to room temperature and filtrated. The filtrate is extracted with CH$_2$Cl$_2$ and washed with aqueous NaHCO$_3$ solution followed by brine, dried over Na$_2$SO$_4$, filtered and evaporated in vacuo. The residue is purified by silica gel column chromatography (n-hexane:ethyl acetate=4:1) to afford the 2-bromomethyl-3-fluoro-6-nitro-benzoic acid methyl ester (4.48 g, 15.3 mmol, 54%) as yellow oil. $^1$H-NMR (400 MHz, δ, ppm) CDCl3: 4.01 (s, 3H), 4.53 (d, 2H), 7.31 (dd, 1H), 8.17 (dd, 1H).

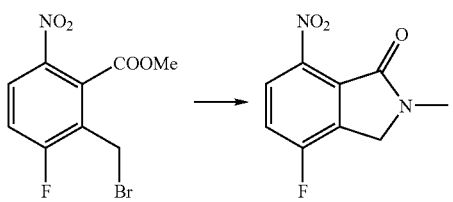

At room temperature, a solution of 2-bromomethyl-3-fluoro-6-nitro-benzoic acid methyl ester (4.48 g, 15.3 mmol) in THF (100 mL) is treated with 2M solution of methylamine in THF (23 mL, 46 mmol), and the mixture is stirred for 48 h at the room temperature. The reaction mixture is filtrated through a glass filter and the precipitates are collected and washed with ethyl acetate. The filtrate is washed with sat. aqueous solution of NaHCO$_3$ and brine, dried over Na$_2$SO$_4$, and concentrated under reduced pressure to give 4-fluoro-2-methyl-7-nitro-2,3-dihydro-isoindol-1-one (1.6 g, 7.61 mmol 50%) as yellow solids. $^1$H-NMR (400 MHz, δ, ppm) CDCl3: 3.22 (s, 3H), 4.47 (s, 2H), 7.32 (dd, 1H), 7.84 (dd, 1H).

Example 12

Preparation of 4-(2-methyl-7-nitro-1-oxo-2,3-dihydro-1H-isoindol-4-yl)-piperazine-1-carboxylic acid tert-butyl ester

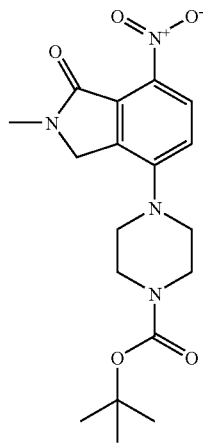

To a suspension of 4-fluoro-2-methyl-7-nitro-2,3-dihydro-isoindol-1-one (2.0 g, 8.52 mmol) and potassium carbonate (657.9 mg, 4.76 mmol), triethylamine (2.0 mL, 14.3 mmol) in dimethylsulfoxide (20 mL), piperazine-1-carboxylic acid tert-butyl ester (1.77 g, 9.52 mmol) is added and the mixture is stirred at 60° C. for 6 hours. The mixture is poured into iced water and the resulting brown solids are collected by filtration. The obtained solid is dried in vacuo at 50° C. to afford 4-(2-methyl-7-nitro-1-oxo-2,3-dihydro-1H-isoindol-4-yl)-piperazine-1-carboxylic acid tert-butyl ester as brown solid in 75% yield. Rf=0.25 (Hexane/AcOEt=1/1). $^1$H-NMR (400 MHz, CDCl$_3$, δ, ppm): 1.50 (s, 9H), 3.13 (t, 4H), 3.20 (s, 3H), 3.61 (t, 4H), 4.37 (s, 2H), 7.04 (d, 1H), 7.78 (d, 1H).

Example 13

Preparation of 4-(4-Isopropyl-piperazin-1-yl)-2-methyl-7-nitro-2,3-dihydro-isoindol-1-one

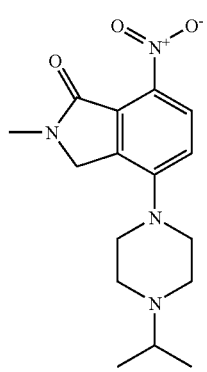

To a suspension of 4-fluoro-2-methyl-7-nitro-2,3-dihydro-isoindol-1-one (5.0 g, 24 mmol) and potassium carbonate (3.32 g, 24 mmol), triethylamine (6.7 mL, 28.8 mmol) in dimethylsulfoxide (50 mL), 1-isopropyl piperazine (4.1 mL, 28.8 mmol) is added and the mixture is stirred at 60° C. for 4 hours. The mixture is poured into iced water, and the resulting brown solids are collected by filtration and dried in vacuo at 50° C. to afford 4-(4-Isopropyl-piperazin-1-yl)-2-methyl-7-nitro-2,3-dihydro-isoindol-1-one as brown solids in 91% yield. Rf=0.14 (AcOEt). $^1$H-NMR (400 MHz, CDCl$_3$, δ, ppm): 1.09 (s, 3H), 1.11 (s, 3H), 2.70 (t, 4H), 2.80-2.74 (m, 1H), 3.19 (s, 3H), 3.21 (t, 4H), 4.37 (s, 2H), 7.01 (d, 1H), 7.78 (d, 1H).

Example 14

The following 2-methyl-7-nitro-4-substituted-2,3-dihydro-isoindol-1-ones are prepared from 4-fluoro-2-methyl-7-nitro-2,3-dihydro-isoindol-1-one and the corresponding amine following the procedure of Example 13.

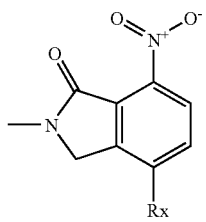

| Expl No. | Rx | NMR (400 MHz), δ (ppm) |
|---|---|---|
| I5 | (1-methyl-4-piperidinyl-piperidine) | DMSO-d6: 1.35-1.60 (m, 8 H), 1.78-1.84 (m, 2 H), 2.35-2.50 (m, 5 H), 2.83-2.92 (m, 2 H), 3.05 (s, 3 H), 3.58-3.65 (m, 2 H), 4.55 (s, 2 H), 7.11 (d, 1 H), 7.77 (d, 1 H). |
| I6 | (1-methyl-4-hydroxypiperidine) | DMSO-d6: 1.47-1.56 (m, 8 H), 1.80-1.90 (m, 2 H), 2.97-3.05 (m, 5 H), 3.43-3.51 (m, 2 H), 3.65-3.77 (m, 1 H), 4.55 (s, 2 H), 4.77 (d, 1 H), 7.11 (d, 1 H), 7.77 (d, 1 H). |
| I7 | (1-methylpiperidine-morpholine spiro) | CDCl3: 2.43-2.55 (m, 3 H), 2.65-2.76 (m, 2 H), 2.88-2.93 (m, 1 H), 3.10-3.17 (m, 2 H), 3.20 (s, 3 H), 3.30-3.39 (m, 2 H), 3.70-3.80 (m, 2 H), 3.88-3.93 (m, 1 H), 4.36 (s, 2 H), 7.02 (d, 1 H), 7.78 (d, 1 H). |
| I8 | 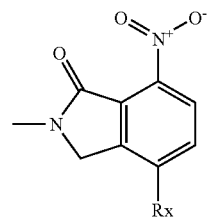 | CDCl3: 2.67 (t, 4 H), 3.20 (s, 3 H), 3.55 (t, 4 H), 4.45 (s, 2 H), 7.09 (d, 1 H), 7.78 (d, 1 H). Rf 0.11 (Hexane/AcOEt = 1/1) |

Example 19

Preparation of 4-[1-(2-methyl-7-nitro-1-oxo-2,3-dihydro-1H-isoindol-4-yl)-piperidin-4-yl]-piperazine-1-carboxylic acid tert-butyl ester

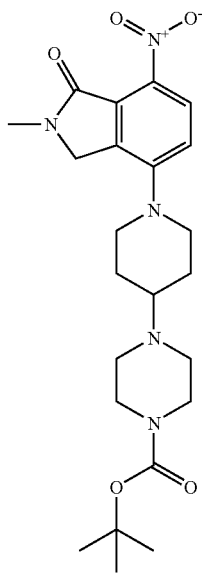

To a solution of 2-methyl-7-nitro-4-(4-oxo-piperidin-1-yl)-2,3-dihydro-isoindol-1-one (4.2 g, 14.5 mmol) and piperazine-1-carboxylic acid tert-butyl ester (3.24 g, 17.4 mmol) in 1,2-dichloroethane is added sodium triacetoxy borohydride (3.69 g, 17.4 mmol) at 0° C. under nitrogen atmosphere. After the mixture is stirred at room temperature for 5 hours, 1N sodium hydroxide aqueous solution is added at 0° C. The mixture is extracted with dichloromethane and the organic layer is washed with brine, dried over sodium sulfate and concentrated in vacuo. The residue is purified by silica gel column chromatography (AcOEt; AcOEt: MeOH=9: 1) to give 4-[1-(2-methyl-7-nitro-1-oxo-2,3-dihydro-1H-isoindol-4-yl)-piperidin-4-yl]-piperazine-1-carboxylic acid tert-butyl ester (4.16 g, 62%). ¹H-NMR (400 MHz, CDCl₃, δ, ppm): 1.47 (s, 9H), 1.66-1.76 (m, 2H), 1.94-2.02 (m, 2H), 2.42-2.59 (m, 5H), 2.84-2.93 (m, 2H), 3.05 (s, 3H), 3.40-3.49 (m, 4H), 3.49-3.57 (m, 2H), 4.35 (s, 2H), 7.00 (d, 1H), 7.76 (d, 1H).

Example I10

Preparation of 4-(7-amino-2-methyl-1-oxo-2,3-dihydro-1H-isoindol-4-yl)-piperazine-1-carboxylic acid tert-butyl ester

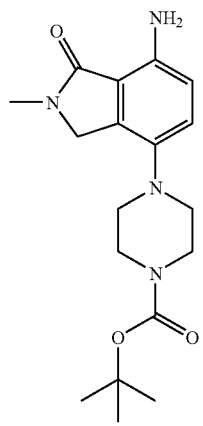

To a solution of 4-(2-methyl-7-nitro-1-oxo-2,3-dihydro-1H-isoindol-4-yl)-piperazine-1-carboxylic acid tert-butyl ester (5.37 g, 14 mmol) in ethanol (200 mL), iron powder (3.98 g, 70 mmol) and 1N hydrogen chloride (28 mL) are added and the mixture is stirred at 60° C. for 2 hours. The mixture is cooled to room temperature, and then 1N sodium hydroxide (28 mL) is added. After removing insoluble material by filtration, the mixture is concentrated. The residue is extracted twice with dichloromethane. The organic layer is successively washed with water and brine, dried over magnesium sulfate, and evaporated in vacuo to afford 4-(7-Amino-2-methyl-1-oxo-2,3-dihydro-1H-isoindol-4-yl)-piperazine-1-carboxylic acid tert-butyl ester (4.9 g) as pale green amorphous solids in 99% yield. Rf=0.18 (Hexane/AcOEt=111). ¹H-NMR (400 MHz, CDCl₃, δ, ppm): 1.49 (s, 9H), 2.85 (t, 4H), 3.13 (s, 3H), 3.54 (t, 4H), 4.28 (s, 2H), 5.03 (s, 2H), 6.56 (d, 1H), 6.96 (d, 1H).

Example I11

Preparation of 7-Amino-4-(4-isopropyl-piperazin-1-yl)-2-methyl-2,3-dihydro-isoindol-1-one

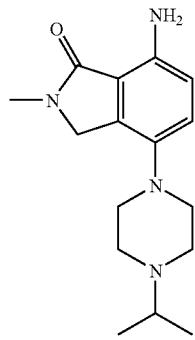

To a solution of 4-(4-Isopropyl-piperazin-1-yl)-2-methyl-7-nitro-2,3-dihydro-isoindol-1-one (4.56 g, 14 mmol) in ethanol (130 mL), iron powder (4.0 g, 70 mmol) and 1N hydrochloric acid (28 mL) are the mixture is added stirred at 60° C. for 3 hours. The mixture is cooled and then, 1N sodium hydroxide (28 mL) is added. After removing insoluble materials by filtration, the mixture is evaporated. The resulting pale yellow solids are collected by filtration and dried in vacuo at 50° C. to afford 7-Amino-4-(4-isopropyl-piperazin-1-yl)-2-methyl-2,3-dihydro-isoindol-1-one (3.43 g) as brown solids in 83% yield. Rf=0.18 (Hexane/AcOEt=111). ¹H-NMR (400 MHz, CDCl₃, δ, ppm): 1.09 (s, 3H), 1.10 (s, 3H), 2.65 (t, 4H), 2.75-2.69 (m, 1H), 2.96 (t, 4H), 3.13 (s, 3H), 4.28 (s, 2H), 4.99 (s, 2H), 6.56 (d, 1H), 6.99 (d, 1H).

The following 7-amino-2-methyl-4-substituted-2,3-dihydro-isoindol-1-ones are prepared from the corresponding 2-methyl-7-nitro-4-substituted-2,3-dihydro-isoindol-1-ones following the procedure of Example I11.

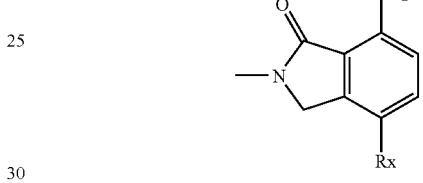

| Expl No. | Rx | NMR, δ (ppm) |
|---|---|---|
| I12 | ![structure] | CDCl3 (270 MHz): 1.30-2.10 (m, 10 H), 2.50-3.13 (m, 12 H), 4.26 (s, 2 H), 4.98 (bs, 2 H), 6.54 (d, 1 H), 6.95 (d, 1 H). |
| I13 | ![structure] | CDCl3 (400 MHz): 1.65-1.74 (m, 2 H), 1.85-2.05 (m, 2 H), 2.70-2.81 (m, 2 H), 3.07-3.14 (m, 5 H), 3.78-3.87 (m, 1 H), 4.27 (s, 2 H), 4.85-5.15 (m, 2 H), 6.55 (d, 1 H), 6.98 (d, 1 H). |
| I14 | ![structure] | CDCl3 (400 MHz): 2.40-2.55 (m, 4 H), 2.67-2.80 (m, 1 H), 2.80-2.85 (m, 2 H), 2.97-3.02 (m, 2 H), 3.10 (s, 3 H), 3.28-3.34 (m, 1 H), 3.68-3.76 (m, 2 H), 3.85-3.90 (m, 1 H), 4.27 (s, 2 H), 5.02 (bs, 2 H), 6.55 (d, 1 H), 6.98 (d, 1 H). |

| Expl No. | Rx | NMR, δ (ppm) |
|---|---|---|
| I15 | 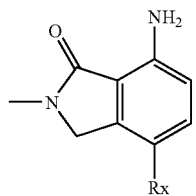 | CDCl3 (400 MHz): 1.47 (s, 9 H), 1.60-1.72 (m, 2 H), 1.84-1.93 (m, 2 H), 2.10-2.43 (m, 1 H), 2.49-2.58 (m, 4 H), 2.62-2.71 (m, 2 H), 3.13 (s, 3 H), 3.13-3.20 (m, 2 H), 3.41-3.49 (m, 4 H), 4.26 (s, 2 H), 4.99 (s, 2 H), 6.54 (d, 1 H), 6.95 (d, 1 H). |

Example I17:

Preparation of 4-[7-(2,5-dichloro-pyrimidin-4-ylamino)-2-methyl-1-oxo-2,3-dihydro-1H-isoindol-4-yl]-piperazine-1-carboxylic acid tert-butyl ester

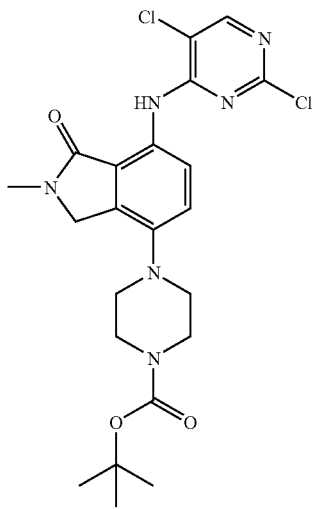

To a suspension of 4-(7-Amino-2-methyl-1-oxo-2,3-dihydro-1H-isoindol-4-yl)-piperazine-1-carboxylic acid tert-butyl ester (6.14 g, 18 mmol) and potassium carbonate (3.86 g, 4.76 mmol) in dimethylsulfoxide (60 mL), 2,4,5-trichloropyrimidine (3.1 mL, 27 mmol) is added and the mixture is stirred at 60° C. for 2 hours. To the mixture, 2,4,5-trichloro pyrimidine (1.0 mL, 9 mmol) is added. After stirring at 60° C. for 2 hours, 2,4,5-trichloropyrimidine (1.0 mL, 9 mmol) is added and the mixture is further allowed to stir at 60° C. for 10 hours. The mixture is cooled and then poured into iced water. The resulting brown solids are collected by filtration and washed with MeOH, and dried in vacuo at 50° C. to afford 4-[7-(2,5-Dichloro-pyrimidin-4-ylamino)-2-methyl-1-oxo-2,3-dihydro-1H-isoindol-4-yl]-piperazine-1-carboxylic acid tert-butyl ester as brown solids (5.29 g) in 60% yield. Rf=0.28 (Hexane/AcOEt=1/1). ¹H-NMR (400 MHz, CDCl₃, δ, ppm): 1.50 (s, 9H), 2.99 (t, 4H), 3.23 (s, 3H), 3.59 (t, 4H), 4.40 (s, 2H), 7.18 (d, 1H), 8.21 (s, 1H), 8.67 (d, 1H), 11.0 (s, 1H).

Example I18:

Preparation of 7-(2,5-dichloro-pyrimidin-4-ylamino)-4-(4-isopropyl-piperazin-1-yl)-2-methyl-2,3-dihydro-isoindol-1-one

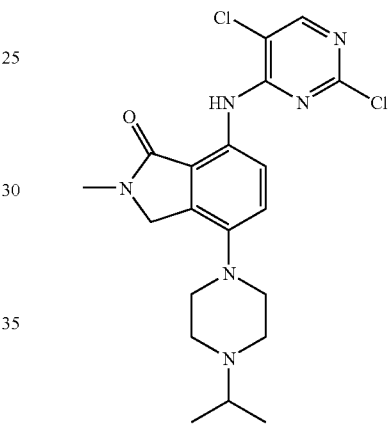

To a suspension of 7-amino-4-(4-isopropyl-piperazin-1-yl)-2-methyl-2,3-dihydro-isoindol-1-one (1.62 g, 5.6 mmol) and potassium carbonate (2.55 g, 8.7 mmol) in dimethylsulfoxide (30 mL), 2, 4, 5-trichloropyrimidine (970 µL, 8.4 mmol) is added and stirred at 70° C. for 4 hours. To the mixture is added 2,4,5-trichloropyrimidine (650 µL, 5.6 mmol) and the mixture is stirred at 70° C. for 6 hours. The mixture is cooled and then extracted twice with dichloromethane. The organic layer is successively washed with water and brine, dried over magnesium sulfate, and evaporated in vacuo. The residue is purified by silica gel column chromatography to afford 7-(2,5-dichloro-pyrimidin-4-ylamino)-4-(4-isopropyl-piperazin-1-yl)-2-methyl-2,3-dihydro-isoindol-1-one (1.95 g) as yellow solids in 80% yield. Rf=0.26 (MeOH/AcOEt=1/4). ¹H-NMR (400 MHz, CDCl₃, δ, ppm): 1.13 (s, 3H), 1.14 (s, 3H), 2.87-2.69 (m, 5H), 3.18-3.08 (m, 4H), 3.22 (s, 3H), 4.40 (s, 2H), 7.20 (d, 1H), 8.20 (s, 1H), 8.66 (d, 1H), 11.0 (s, 1H).

The following 7-(2,5-dichloro-pyrimidin-4-ylamino)-2-methyl-4-substituted-2,3-dihydro-isoindol-1-ones are prepared from the corresponding 7-amino-2-methyl-4-substituted-2,3-dihydro-isoindol-1-ones and 2,4,5-trichloropyrimidine following the procedure of Example D.

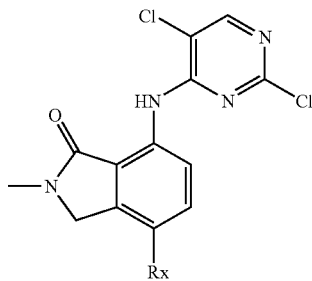

| Expl No. | Rx | NMR (400 MHz), δ (ppm) |
|---|---|---|
| I19 | (1-piperidinyl-piperidine, N-methyl) | CDCl₃: 1.45-1.79 (m, 8 H), 1.92-1.98 (m, 2 H), 2.30-2.45 (m, 1 H), 2.50-2.60 (m, 4 H), 2.72-2.77 (m, 2 H), 3.21 (s, 3 H), 3.32-3.39 (m, 2 H), 4.38 (s, 2 H), 7.17 (d, 1 H), 8.19 (s, 1 H), 8.63 (d, 1 H), 10.98 (s, 1 H). |
| I20 | 4-hydroxy-1-methylpiperidine | DMSO-d6: 1.45-1.59 (m, 2 H), 1.82-1.90 (m, 2 H), 2.78-2.85 (m, 2 H), 3.10 (s, 3 H), 3.23-3.32 (m, 2 H), 3.60-3.67 (m, 1 H), 4.53 (s, 2 H), 4.71 (d, 1 H), 7.22 (d, 1 H), 8.41 (d, 1 H), 8.47 (s, 1 H), 11.69 (s, 1 H). |
| I21 | octahydropyrazino-morpholine derivative | CDCl₃: 2.43-2.63 (m, 4 H), 2.70-2.75 (m, 1 H), 2.86-2.91 (m, 1 H), 2.96-3.11 (m, 2 H), 3.17-3.23 (m, 4 H), 3.31-3.37 (m, 1 H), 3.70-3.78 (m, 2 H), 3.88-3.93 (m, 1 H), 4.39 (s, 2 H), 7.19 (d, 1 H), 8.21 (s, 1 H), 8.67 (d, 1 H), 10.98 (s, 1 H). |
| I22 | 4-(4-Boc-piperazin-1-yl)-1-methylpiperidine | CDCl₃: 1.47 (s, 9 H), 1.63-1.74 (m, 2 H), 1.93-1.98 (m, 2 H), 2.37-2.48 (m, 1 H), 2.52-2.60 (m, 4 H), 2.74-2.81 (m, 2 H), 3.22 (s, 3 H), 3.32-3.38 (m, 2 H), 3.43-3.49 (m, 4 H), 4.38 (s, 2 H), 7.17 (d, 1 H), 8.20 (s, 1 H), 8.64 (d, 1 H), 10.98 (s, 1 H), ESI-MS m/z: 576, 578. |

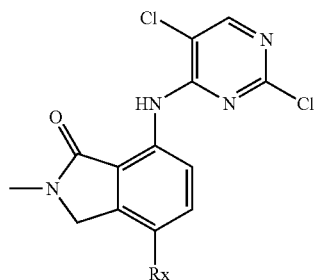

| Expl No. | Rx | NMR (400 MHz), δ (ppm) |
|---|---|---|
| I23 | 1'-Boc-1-methyl-4,4'-bipiperidine | CDCl₃: 1.13-1.34 (m, 5 H), 1.36-1.48 (m, 3 H), 1.47 (s, 9 H), 1.67-1.75 (m, 2 H), 1.77-1.87 (m, 2 H), 1.77-1.87 (m, 2 H), 1.77-1.87 (m, 2 H), 2.60-2.76 (m, 4 H), 3.22 (s, 3 H), 3.28-3.37 (m, 2 H), 7.16 (d, 1 H), 8.19 (s, 1 H), 8.64 (d, 1 H), 10.98 (s, 1 H). |

Example I27:

Preparation of 5-fluoro-2-methyl-8-nitro-3,4-dihydro-2H-isoquinolin-1-one

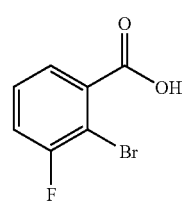

In a 1 L, three necked, round-bottomed flask fitted with a dropping funnel and a thermometer, were charged 20 g (0.13 mol) of 2-amino-3-fluoro-benzoic acid and 160 mL of acetonitrile. After cooling to 0° C., 160 mL of hydrobromic acid (47%) was added dropwise over 10 min. To the resulting solution, 10 g of NaNO₂ (0.145 mol) in water (20 mL) was added dropwise over 1 hour. After addition, the reaction mixture was stirred at 0° C. for 5 min, and 21.8 g of Cu(I) Br (0.15 mol) was added portionwise over 30 min. Stirring was continued at 70° C. in an oil bath for 1 hour. After cooling to 0° C., 700 mL of H₂O was added and the precipitate was filtered, washed with cold water and dried under vacuum to give an orange solid corresponding to 2-bromo-3-fluoro-benzoic acid (22 g, 78%).

¹H-NMR (400 MHz, CDCl₃, δ, ppm): 7.32 (ddd, 1H), 7.39 (ddd, 1H), 7.74-7.80 (m, 1H).

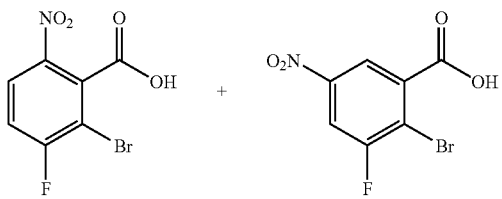 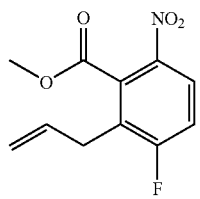

In a 1 L, three necked, round-bottomed flask fitted with a dropping funnel and a thermometer were charged 33 g (0.15 mol) of 2-bromo-3-fluoro-benzoic acid and 200 mL of concentrated sulfuric acid. After cooling to 0° C., 16 mL of HNO3 (70%) was added dropwise over 30 min keeping temperature at 10 or less degrees. After 1 h, the reaction mixture was poured into the crushed ice keeping temperature at 20 or less degrees. The mixture was extracted twice with ethyl acetate. The combined organic layers were washed with brine and dried over sodium sulfate. The solvent was removed under reduced pressure to give a mixture of 2-bromo-3-fluoro-6-nitro-benzoic acid and 2-bromo-3-fluoro-5-nitro benzoic acid (2:1) as brown solids in quantitative yield.

$^1$H-NMR (400 MHz, CDCl$_3$, δ, ppm)

2-bromo-3-fluoro-6-nitro-benzoic acid: 7.37 (dd, 1H), 8.27 (dd, 1H), 2-bromo-3-fluoro-5-nitro benzoic acid: 8.15 (dd, 1H), 8.62-8.65 (m, 1H).

In a 2 L, one necked, round-bottomed flask were charged 130 g (0.47 mol) of a mixture of 2-bromo-3-fluoro-6-nitrobenzoic acid methyl ester and 2-bromo-3-fluoro-5-nitrobenzoic acid methyl ester, 159 mL (0.52 mol) of allyltributyltin and 1.2 L of toluene. To the mixture, 27 g (2.3 mmol) of tetrakis(triphenylphosphine)palladium(0) was added and the mixture was stirred at 130° C. for 7 hours. After cooling to room temperature, 90 g (2.1 mol) of sodium fluoride in 800 mL of water was added into the reaction mixture.

The mixture was extracted twice with ethyl acetate. The combined organic layers were washed with water and brine, dried over sodium sulfate, and evaporated under reduced pressure to give 247 g of black oil. The crude products were cautiously purified by silica gel column chromatography (Hexane/AcOEt, 95/5) to give 2-allyl-3-fluoro-6-nitro-benzoic acid methyl ester (71 g, 63%) as a yellow oil.

$^1$H-NMR (400 MHz, CDCl$_3$, δ, ppm): 3.45 (dd, 2H), 3.95 (s, 3H), 5.01-5.13 (m, 2H), 5.79-5.92 (m, 1H), 7.21-7.28 (m, 1H), 8.10 (d, 1H).

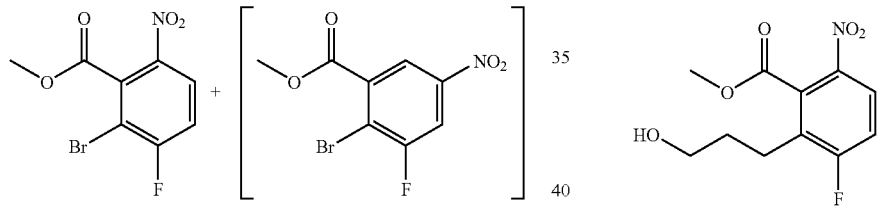

In a 2 L, one necked, round-bottomed flask were charged 130 g (0.49 mol) of a mixture of 2-bromo-3-fluoro-6-nitrobenzoic acid and 2-bromo-3-fluoro-5-nitro benzoic acid and 900 mL of methanol. To the mixture, 84 g (0.52 mol) of cesium carbonate was added and the resulting suspension was stirred for 30 minutes. The reaction mixture was concentrated under reduced pressure to remove the solvent. To the mixture 900 mL of DMF followed by iodomethane (33.7 mL, 0.54 mmol) was added and the mixture was stirred for 17 hours. The reaction mixture was poured into the crushed ice and extracted twice with ethyl acetate. The combined organic layers were washed with water, 1M HCl and brine, dried over sodium sulfate and evaporated under reduced pressure to give a mixture of 2-bromo-3-fluoro-6-nitrobenzoic acid methyl ester and 2-bromo-3-fluoro-5-nitrobenzoic acid methyl ester (2:1) a brown oil in quantitative yield.

$^1$H-NMR (400 MHz, CDCl$_3$, δ, ppm)

2-bromo-3-fluoro-6-nitrobenzoic acid methyl ester: 4.04 (s, 3H), 7.34 (dd, 1H), 8.24 (dd, 1H), 2-bromo-3-fluoro-5-nitrobenzoic acid methyl ester: 4.02 (s, 3H), 8.10 (dd, 1H), 8.47-8.50 (m, 1H).

In a 2 L, three necked, round-bottomed flask were charged 892 mL (0.45 mol) of 9-BBN (0.5M) and 100 mL of THF. After cooling to 0° C., 71 g (0.3 mol) of 2-allyl-3-fluoro-6-nitrobenzoic acid methyl ester in 150 mL of THF was added over 30 minutes and the mixture was stirred at room temperature for 5 hours. After cooling to 0° C., 700 mL of 1M NaOH aq was added into the reaction mixture, which was stirred for 30 minutes. To the mixture, 200 mL of hydrogen peroxide (35%) was added over 30 minutes then stirred at room temperature for 1 hours. The mixture was extracted twice with ethyl acetate. The combined organic layers were washed with water, a solution of sodium thiosulfate and brine, and was dried over sodium sulfate. The solvent was removed under reduced pressure to give 104 g of 3-fluoro-2-(3-hydroxypropyl)-6-nitro-benzoic acid methyl ester as orange oil. The crude product was used for the next reaction.

$^1$H-NMR (400 MHz, CDCl$_3$, δ, ppm): 1.83-1.92 (m, 2H), 2.74-2.79 (m, 2H), 3.66 (t, 2H), 3.98 (s, 3H), 7.21-7.27 (m, 1H), 8.10 (dd, 1H).

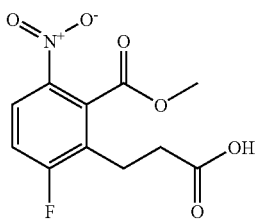

To a solution of 3-fluoro-2-(2-hydroxyethyl)-6-nitro-benzoic acid methyl ester (51.4 g, 0.2 mol) in acetone (1000 mL), 2,2,6,6-tetramethylpiperidine 1-oxyl, Free radical, (460.6 mg, 2.95 mmol), an aqueous 15% solution of sodium hydrocarboxide (400 mL) and sodium bromide (3.02 g, 29.3 mmol) was added. Trichloroisocyanuric acid (68.4 g, 0.29 mol) was then slowly added within 30 min at rt. After completion of the addition and being stirred at rt for 2.5 hrs, 15 mL of isopropanol was added at 0° C. carefully. The mixture was concentrated under reduced pressure. The mixture was extracted three times with ethyl acetate. The organic layer was extracted three times with 1N sodium hydroxide. The combined water layer was washed once with ethyl acetate, then acidified with 5N hydrogen chloride at 0° C. After extraction four times with ethyl acetate, the organic layer was washed with water and brine, dried over magnesium sulfate, and evaporated in vacuo. The title compound 2-(2-carboxy-ethyl)-3-fluoro-6-nitro-benzoic acid methyl ester (28.7 g) was obtained as yellow solid in 72% yield (2 steps).

$^1$H-NMR (400 MHz, CDCl$_3$, δ, ppm): 2.63-2.71 (m, 2H), 2.95-3.04 (m, 2H), 3.99 (s, 3H), 7.22-7.28 (m, 1H), 8.12 (dd, 1H).

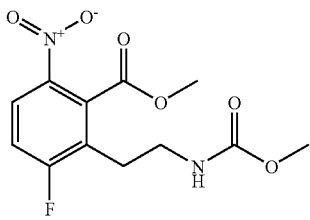

Included water in 2-(2-carboxy-ethyl)-3-fluoro-6-nitrobenzoic acid methyl ester (20.7 g, 76 mol) was removed twice by azeotropy with toluene, and the starting material was dissolved in dry toluene (380 mL). To this solution, diphenylphosphoryl azide (17.1 mL, 80 mmol) and triethylamine (11.6 mL, 83.6 mmol) were added at rt and the mixture was stirred at 80° C. for 2.0 hrs. Then, a solution of copper chloride (1.02 g, 7.6 mmol) in dry methanol (170 mL) was added and the resulting mixture was further stirred at 80° C. for 1.5 hrs. After cooling, saturated sodium hydrogen carbonate was added and the mixture was extracted three times with ethyl acetate. The organic layer was washed three times with water and brine, dried over magnesium sulfate, and evaporated in vacuo. The resulting solid was washed with methanol and then ether to give 3-fluoro-2-(2-methoxy-carbonylamino-ethyl)-6-nitro-benzoic acid methyl ester (16.6 g) as pale brown solid in 72% yield. The filtrate was purified by column chromatography (hexane/ethyl acetate=from 4/1 to 1/1) to give additional title compound (3.8 g) as pale brown. As a result, total 20.4 g of 3-fluoro-2-(2-methoxycarbonylamino-ethyl)-6-nitro-benzoic acid methyl ester was obtained in 89% yield.

$^1$H-NMR (400 MHz, CDCl$_3$, δ, ppm): 2.85-2.93 (m, 2H), 3.35-3.48 (m, 2H), 3.64 (s, 3H), 4.00 (s, 3H), 5.02 (br.s, 1H), 7.23-7.28 (m, 1H), 8.13 (d, 1H).

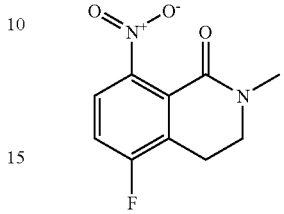

To a solution of 3-fluoro-2-(2-methoxycarbonylamino-ethyl)-6-nitro-benzoic acid methyl ester (20.4 g, 68 mmol) in THF (200 mL), sodium hydride (5.44 g, 136 mmol) was added at 0° C. and the mixture was stirred at rt for 2.0 hrs. To the reaction mixture was added methyl iodide (12.7 mL, 204 mmol) at 0° C. and the mixture was stirred at rt for 1.5 hours. To the mixture was added saturated ammonium chloride solution at 0° C., and the mixture was extracted three times with ethyl acetate. The organic layer was washed twice with water and brine, dried over magnesium sulfate, and evaporated in vacuo. The residue was purified by silica gel column chromatography (dichloromethane/ethyl acetate/hexane: from 99/1/50 to 99/2/50) to give 5-fluoro-2-methyl-8-nitro-3,4-dihydro-2H-isoquinolin-1-one (10.9 g) as yellow solid in 71% yield.

$^1$H-NMR (400 MHz, CDCl$_3$, δ, ppm): 3.04 (t, 2H), 3.16 (s, 3H), 3.64 (t, 2H), 7.19-7.27 (m, 1H), 7.42 (dd, 1H)

Example I28

Preparation of 4-[1-(2-methyl-8-nitro-1-oxo-1,2,3,4-tetrahydro-isoquinolin-5-yl)-piperidin-4-yl]-piperazine-1-carboxylic acid tert-butyl ester

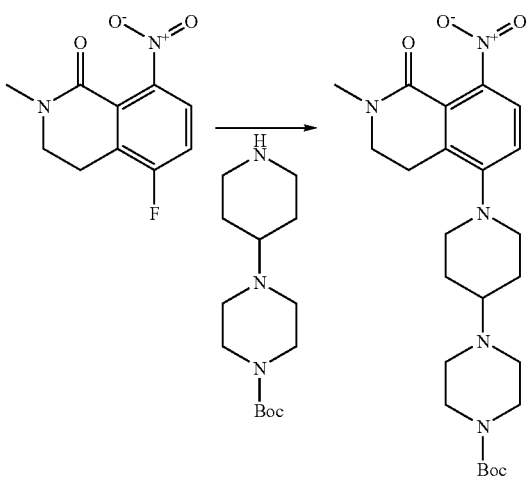

A mixture of 5-fluoro-2-methyl-8-nitro-3,4-dihydro-2H-isoquinolin-1-one (11.65 g, 0.052 mol), 4-piperidin-4-yl-piperazine-1-carboxylic acid tert-butyl ester (28.0 g, 0.1039 mol), K2CO3 (8.98 g, 0.065 mol) in DMSO (350 mL) was stirred at 85° C. for 12 hours. After cooling to room temperature, ice-water (500 mL) was added. The mixture was extracted with AcOEt. The organic layer was washed with water followed by brine, dried over Na2SO4 and evaporated. The residue was purified by silica gel column chromatography (AcOEt; then AcOEt/MeOH=6/1) to give 10.09 g of the desired product 4-[1-(2-methyl-8-nitro-1-oxo-1,2,3,4-tetrahydro-isoquinolin-5-yl)-piperidin-4-yl]-piperazine-1-carboxylic acid tert-butyl ester as pale yellow solid in 41% yield.

$^1$H-NMR (400 MHz, CDCl$_3$, δ, ppm): 1.47 (s, 9H), 1.62-1.80 (m, 2H), 1.91-1.99 (m, 2H), 2.00-2.08 (m, 1H), 2.34-2.45 (m, 1H), 2.48-2.62 (m, 4H), 2.66-2.74 (m, 1H), 2.94 (t, 2H), 3.16 (s, 3H), 3.08-3.21 (m, 2H), 3.38-3.51 (m, 4H), 3.55 (t, 2H), 7.09 (d, 1H), 7.38 (d, 1H).

The following 2-methyl-8-nitro-3,4-dihydro-5-substituted-2H-isoquinolin-1-ones are prepared from 5-fluoro-2-methyl-8-nitro-3,4-dihydro-2H-isoquinolin-1-one and the corresponding amine following the procedure of Example I28.

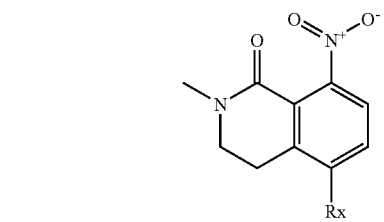

| Expl No. | Rx | NMR (400 MHz), δ (ppm) |
|---|---|---|
| I29 | 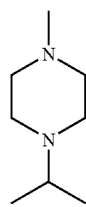 | CDCl3: 1.14 (d, 6 H), 2.68-2.79 (m, 4 H), 2.79-2.88 (m, 1 H), 2.98-3.50 (m, 4 H), 3.15 (s, 3 H), 3.55 (t, 2 H), 7.13 (d, 1 H), 7.39 (d, 1 H). |
| I30 | 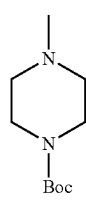 | CDCl3: 1.49 (s, 9 H), 2.84-2.91 (m, 4 H), 2.98 (t, 2 H), 3.16 (s, 3 H), 3.53-3.63 (m, 6 H), 7.10 (d, 1 H), 7.41 (d, 1 H). |

Example I31:

Preparation of 4-[1-(8-amino-2-methyl-1-oxo-1,2,3,4-tetrahydro-isoquinolin-5-yl)-piperidin-4-yl]-piperazine-1-carboxylic acid tert-butyl ester

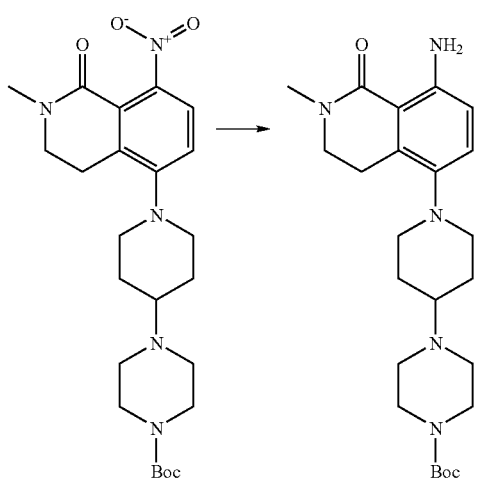

To a mixture of 20 g of nitro compound 4-[1-(2-methyl-8-nitro-1-oxo-1,2,3,4-tetrahydro-isoquinolin-5-yl)-piperidin-4-yl]-piperazine-1-carboxylic acid tert-butyl ester (0.0211 mol) in EtOH (200 mL), iron powder (5.9 g, 0.106 mol) and 2N HCl aq (21 mL, 0.042 mol) were added and the mixture was stirred at 80° C. for 3 hours. After cooling to room temperature, 2N NaOH aq (22 mL) was added. The resulting mixture was filtrated through Celite and evaporated in vacuo to afford 93.38 g of the desired aniline 4-[1-(8-amino-2-methyl-1-oxo-1,2,3,4-tetrahydro-isoquinolin-5-yl)-piperidin-4-yl]-piperazine-1-carboxylic acid tert-butyl ester (9.38 g, quantitative yield) as pale yellow amorphous powder.

$^1$H-NMR (400 MHz, CDCl$_3$, δ, ppm): 1.47 (s, 9H), 1.58-1.73 (m, 2H), 1.84-1.93 (m, 2H), 2.27-2.44 m, 1H), 2.46-2.66 (m, 6H), 2.88-2.99 (m, 4H), 3.11 (s, 3H), 3.40-3.53 (m, 6H), 5.20-6.35 (br.s., 2H), 6.50 (d, 1H), 7.00 (d, 1H).

The following 5-substituted-8-amino-2-methyl-3,4-dihydro-2H-isoquinolin-1-ones are prepared from 5-substituted-2-methyl-8-nitro-3,4-dihydro-2H-isoquinolin-1-ones following the procedure of Example I31.

| Expl No. | Rx | NMR (400 MHz), δ ppm |
|---|---|---|
| I32 | (1-isopropyl-piperazin-4-yl-methyl) | CDCl3: 1.09 (d, 6 H), 2.41-2.77 (m, 5 H), 2.77-2.84 (m, 4 H), 2.98 (t, 2 H), 3.11 (s, 3 H), 3.44 (t, 2 H), 5.85 (br. s., 2 H), 6.52 (d, 1 H), 7.05 (d, 1 H). |
| I33 | (1-Boc-piperazin-4-yl-methyl) | CDCl3: 1.48 (s, 9 H), 2.61-2.77 (m, 4 H), 2.99 (t, 2 H), 3.11 (s, 3 H), 3.15-4.45 (broadened, 4 H), 3.45 (t, 2 H), 5.65-6.10 (broadened, 2 H), 6.52 (d, 1 H), 6.99 (d, H). |

Example I34:

Preparation of 4-{1-[8-(2,5-dichloro-pyrimidin-4-ylamino)-2-methyl-1-oxo-1,2,3,4-tetrahydro-isoquinolin-5-yl]-piperidin-4-yl}-piperazine-1-carboxylic acid tert-butyl ester

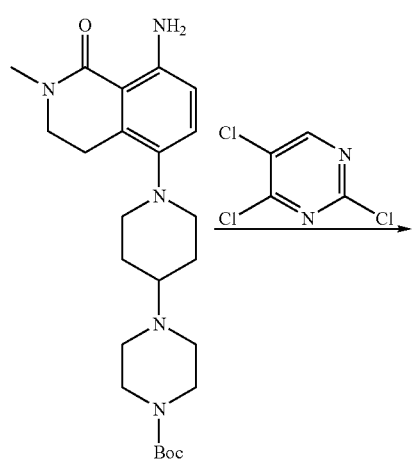

A mixture 4-[1-(8-amino-2-methyl-1-oxo-1,2,3,4-tetrahydro-isoquinolin-5-yl)-piperidin-4-yl]-piperazine-1-carboxylic acid #tert!-butyl ester (9.20 g, 20.7 mmol), 2,4,5-trichloropyrimidine (5.96 mL, 51.8 mmol), K2CO3 (7.17 g, 51.8 mmol) in DMSO (200 mL) was stirred at 60° C. for 12 hours. After cooling to room temperature, 700 mL of water was added with stirring. The mixture was filtrated. The resulting brown solids were suspended in CH3CN (ca. 200 mL), stirred for a while and filtrated. The residue was further washed with CH3CN and dried under reduced pressure to give 8.75 g of 4-{1-[8-(2,5-dichloro-pyrimidin-4-ylamino)-2-methyl-1-oxo-1,2,3,4-tetrahydro-isoquinolin-5-yl]-piperidin-4-yl}-piperazine-1-carboxylic acid tert-butyl ester as pale beige solids in 72% yield.

$^1$H-NMR (400 MHz, CDCl$_3$, δ, ppm): 1.47 (s, 9H), 1.61-1.74 (m, 2H), 1.88-1.97 (m, 2H), 2.33-2.42 (m, 1H), 2.51-2.59 (m, 4H), 2.65-2.73 (m, 2H), 2.98-3.11 (m, 4H), 3.19 (s, 3H), 3.41-3.54 (m, 6H), 7.24-7.27 (m, 1H), 8.17 (s, 1H), 8.63 (d, 1H), 12.77 (s, 1H).

The following 5-substituted-8-(2,5-dichloro-pyrimidin-4-ylamino)-2-methyl-3,4-dihydro-2H-isoquinolin-1-ones are prepared from 5-substituted-8-amino-2-methyl-3,4-dihydro-2H-isoquinolin-1-ones and 2,4,5-trichloropyrimidine following the procedure of Example I34.

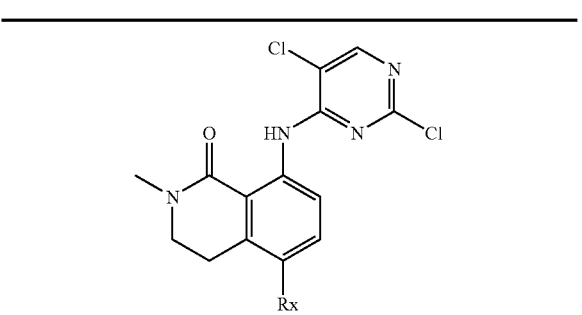

| Expl No. | Rx | NMR (400 MHz), δ (ppm) |
|---|---|---|
| I35 | [structure: piperazine with N-isopropyl] | CDCl3: 1.10 (d, 6 H), 2.61-2.79 (m, 5 H), 2.86-2.94 (m, 4 H), 3.04 (t, 2 H), 3.19 (s, 3 H), 3.51 (t, 2 H), 7.30 (d, 1 H), 8.17 (s, 1 H), 8.64 (d, 1 H), 12.77 (s, 1 H). |
| I36 | [structure: piperazine with N-Boc] | CDCl3: 1.50 (s, 9 H), 2.77-2.88 (m, 4 H), 3.08 (t, 2 H), 3.20 (s, 3 H), 3.35-3.80 (broadened, 4 H), 3.53 (t, 2 H), 7.25-7.30 (m, 1 H), 8.18 (s, 1 H), 8.68 (d, 1 H), 12.82 (s, 1 H). |

Example I37

Preparation of 4-hydroxy-2-methyl-7-nitro-2,3-dihydro-isoindol-1-one

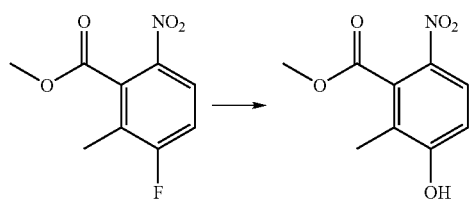

To a stirring solution of 3-Fluoro-2-methyl-6-nitro-benzoic acid methyl ester (6 g, 28.2 mmol) and 2-(methylsulfonyl)ethanol (5.2 g, 42.2 mmol) in 47 mL of DMF is added sodium hydride (3.38 g, 84.6 mmol) at 0° C. and the reaction mixture is allowed to warm to room temperature and then stirred for 1.5 hours. The mixture is quenched with 1N HCl solution and partitioned between ethyl acetate. The organic layer is washed with brine and concentrated to dryness and the crude organics purified by flash column chromatography to give 3-Hydroxy-2-methyl-6-nitro-benzoic acid methyl ester (5.3 g) in 89% yields. $^1$H-NMR (400 MHz, δ, ppm) CDCl3: 2.22 (s, 3H), 3.99 (s, 3H), 6.38 (s, 1H), 6.87 (d, 1H), 7.99 (d, 1H).

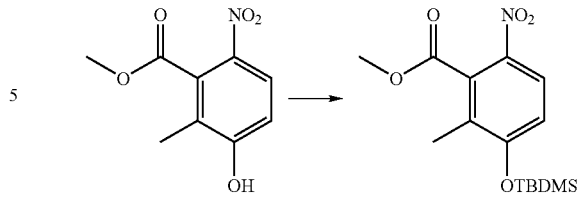

To a solution of 3-hydroxy-2-methyl-6-nitro-benzoic acid methyl ester (5.3 g, 25.1 mmol) in 70 mL of DMF, imidazole (2.56 g, 37.7 mmol) and t-butyl dimethyl silyl chloride (5.67 g, 37.7 mmol) are added at 0° C. and stirred at room temperature for 1 hour. Crushed ice is added to the solution and partitioned between ethyl acetate. The organic layer is washed with water and brine and concentrated to dryness to give 3-Hydroxy-2-methyl-6-nitro-benzoic acid methyl ester (8.9 g). $^1$H-NMR (400 MHz, δ, ppm) CDCl$_3$: 0.19 (s, 6H), 0.92 (s, 9H), 2.09 (s, 3H), 3.87 (s, 3H), 6.76 (d, 1H), 7.89 (d, 1H).

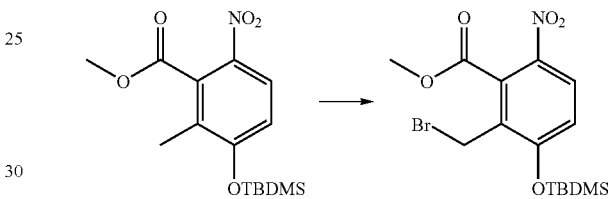

To a solution of 3-(tert-butyl-dimethyl-silanyloxy)-2-methyl-6-nitro-benzoic acid methyl ester (8.9 g, 25.1 mmol) and N-bromosuccinimide (5.36 g, 30.1 mmol) in 50 mL of CCl$_4$ is added 2,2'-azobisisobutyronitrile (412 mg, 2.5 mmol) at room temperature. The reaction mixture is stirred at 80° C. for 22 hours and then cooled to room temperature and then quenched by crushed ice. The mixture is extracted with dichloromethane and washed with aqueous NaHCO$_3$ solution followed by brine, dried over Na$_2$SO$_4$, filtered and evaporated in vacuo to afford the 2-bromomethyl-3-(tert-butyl-dimethyl-silanyloxy)-6-nitro-benzoic acid methyl ester (12.6 g) as brown oil. $^1$H-NMR (400 MHz, δ, ppm) CDCl$_3$: 0.37 (s, 6H), 1.07 (s, 9H), 4.0 (s, 3H), 4.49 (s, 2H), 6.94 (d, 1H), 8.09 (d, 1H).

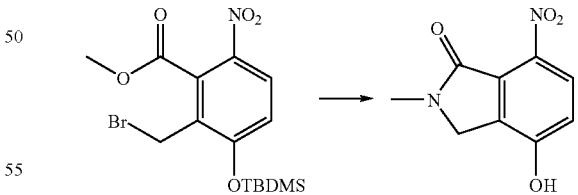

At room temperature, a solution of 2-bromomethyl-3-(tert-butyl-dimethyl-silanyloxy)-6-nitro-benzoic acid methyl ester (12.6 g, 25.1 mmol) in 60 mL of THF is added 2M solution of methylamine in THF (37.7 mL, 75.3 mmol) at 0° C. and then the reaction mixture is stirred for 6 hours at the room temperature. Methanol and 1M Hydrochloric acid solution are added to the reaction mixture. The mixture is evaporated in vacuo and the precipitate is collected to give 4-hydroxy-2-methyl-7-nitro-2,3-dihydro-isoindol-1-one (2.1 g) as yellow solid in 40% yields for 3 steps.

¹H-NMR (400 MHz, δ, ppm) DMSO: 3.05 (s, 3H), 4.37 (s, 2H), 7.02 (d, 1H), 7.8 (d, 1H).

Example I38

Preparation of 4-methoxy-2-methyl-7-nitro-2,3-dihydro-isoindol-1-one

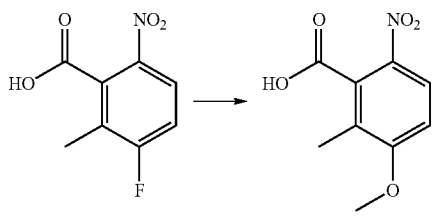

To a stirring solution of 3-Fluoro-2-methyl-6-nitro-benzoic acid (4.2 g, 21 mmol) in THF (40 mL) and methanol (40 mL) is added potassium methoxide in methanol (15 g, 63 mmol) and the solution is heated to 100° C. for 2 hours. The reaction mixture is cooled to room temperature and then the mixture is quenched with a 1N HCl solution and partitioned between ethyl acetate. The organic layer is washed with brine and then concentrated to give 3-Methoxy-2-methyl-6-nitro-benzoic acid (4.3 g) in quantitative yields. ¹H-NMR (400 MHz, δ, ppm) CDCl₃: 2.32 (s, 3H), 3.98 (s, 3H), 6.95 (d, 1H), 8.15 (d, 1H).

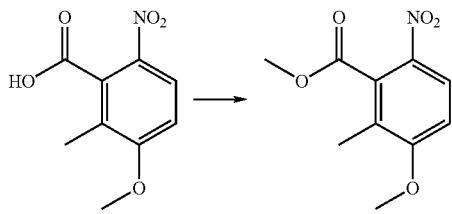

To a solution of 3-Methoxy-2-methyl-6-nitro-benzoic acid in 45 mL of methanol, Cs₂CO₃ (7.8 g, 24 mmol) is added and stirred at the room temperature for 1 hour. The solution is concentrated under reduced pressure then the resulting yellow solid is suspended in 45 ml of DMF. Iodomethane (1.5 ml 24 mol) is added at 0° C. and stirred at the room temperature for 21 hours. Water is added to the solution and the precipitates are collected and washed by water to give 3-Methoxy-2-methyl-6-nitro-benzoic acid methyl ester (4.0 g) as orange solid in 81% yields. ¹H-NMR (400 MHz, δ, ppm) CDCl₃: 2.2 (s, 3H), 3.93 (s, 3H), 3.98 (s, 3H), 6.91 (d, 1H), 8.11 (d, 1H).

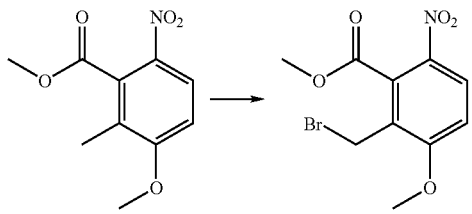

To a suspension of 3-Methoxy-2-methyl-6-nitro-benzoic acid methyl ester (4.1 g, 18.2 mmol) and N-bromosuccinimide (3.89 g, 21.8 mmol) in 50 mL of CCl₄ is added 2,2'-azobisisobutyronitrile (299 mg, 1.82 mmol) at room temperature. The reaction mixture is stirred at 85° C. for 21 hours and then cooled to room temperature. The reaction mixture is cooled to room temperature and then quenched by crushed ice. The mixture is extracted with ethyl acetate and washed with aqueous NaHCO₃ solution followed by brine, dried over Na₂SO₄, filtered and evaporated in vacuo to afford the 2-Bromomethyl-3-methoxy-6-nitro-benzoic acid methyl ester (7.1 g) as orange oil. ¹H-NMR (400 MHz, δ, ppm) CDCl₃: 4.0 (s, 3H), 4.05 (s, 3H), 4.52 (s, 2H), 7.02 (d, 1H), 8.2 (d, 1H).

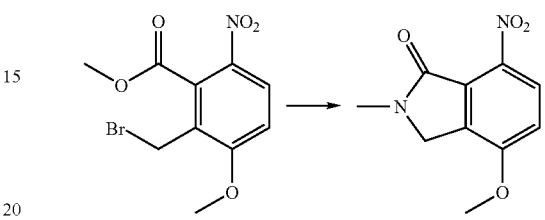

At room temperature, a solution of 2-Bromomethyl-3-methoxy-6-nitro-benzoic acid methyl ester (crude 7.0 g, 18.2 mmol) in 46 mL of THF is treated with 2M solution of methylamine in THF (27.3 mL, 54.6 mmol), and the mixture is stirred for 4 hours at the room temperature. The reaction mixture is quenched with a saturated ammonium chloride solution and partitioned between ethyl acetate. The organic layer is washed with brine and then dried over Na₂SO₄ following concentrated to give 4-Methoxy-2-methyl-7-nitro-2,3-dihydro-isoindol-1-one (3.1 g) as orange solid in 77% yields (2 steps). ¹H-NMR (400 MHz, δ, ppm) CDCl₃: 3.19 (s, 3H), 3.99 (s, 3H), 4.32 (s, 2H), 7.0 (d, 1H), 7.89 (d, 1H).

Example I39

Preparation of 4-(7-amino-2-methyl-1-oxo-2,3-dihydro-1H-isoindol-4-yloxy)-piperidine-1-carboxylic acid tert-butyl ester

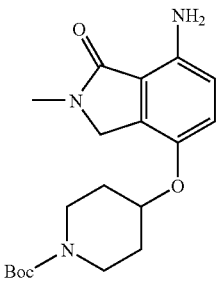

To a solution of 4-hydroxy-2-methyl-7-nitro-2,3-dihydro-isoindol-1-one (700 mg, 3.36 mmol), 4-hydroxy-piperidine-1-carboxylic acid tert-butyl ester (811 mg, 4.03 mmol) and triphenylphosphine (1.06 g, 4.03 mmol) in THF (10 mL), diethyl azadicarboxylate (0.63 mL, 4.03 mmol) is added dropwise at 0° C. After the mixture is stirred at room temperature for 12 h, the mixture is poured into ice water and extracted twice with dichloromethane. The combined organic layer is washed with 1N sodium hydroxide (twice), water, and then brine, and dried over sodium sulfate, filtered and evaporated. The residue is roughly purified by silica gel column chromatography to give 3.23 g of a mixture of 4-(2-methyl-7-nitro-1-oxo-2,3-dihydro-1H-isoindol-4-yloxy)-piperidine-1-carboxylic acid tert-butyl ester, which is used for the next reaction without further purification.

A mixture of 4-(2-methyl-7-nitro-1-oxo-2,3-dihydro-1H-isoindol-4-yloxy)-piperidine-1-carboxylic acid tert-butyl ester (654 mg, 1.0 mmol), iron powder (280 mg, 5.0 mmol), and 1N hydrogen chloride (2 mL, 2.0 mmol) in ethanol (5 mL) is stirred at 80° C. for 1 h under nitrogen atmosphere. After cooling to room temperature, ice and 1N sodium hydroxide are added, the mixture is filtered. The filtrate is extracted with dichloromethane (twice). The combined organic layer is washed with water and then brine, dried over sodium sulfate, filtered and concentrated in vacuo to give 597 mg of 4-(7-amino-2-methyl-1-oxo-2,3-dihydro-1H-isoindol-4-yloxy)-piperidine-1-carboxylic acid tert-butyl ester, which is used for the next reaction without purification.

Example I40:

Preparation of 7-amino-2-methyl-4-(2-morpholin-4-yl-ethoxy)-2,3-dihydro-isoindol-1-one

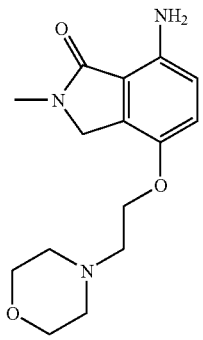

A mixture of 4-hydroxy-2-methyl-7-nitro-2,3-dihydro-isoindol-1-one (1.04 g, 5.0 mmol), 4-(2-chloro-ethyl)-morpholine hydrogen chloride (1.12 g, 6.0 mmol), potassium carbonate (830 mg, 6.0 mmol), potassium iodide (249 mg, 1.5 mmol) in DMF (15 mL) is stirred at 70° C. for 16 h. The mixture is poured into water and extracted with ethyl acetate (twice). The combined organic layer is washed with water and then brine, dried over sodium sulfate, filtered and concentrated in vacuo to give 450 mg of a crude material. The water layer is extracted with dichloromethane (three times). The combined organic layer is washed with brine, dried over sodium sulfate, filtered, and evaporated. The resulting residue is purified twice by silica gel column chromatography (CH2Cl2/Methanol) to give 700 mg of the product. Totally, 1.15 g of 2-methyl-4-(2-morpholin-4-yl-ethoxy)-7-nitro-2,3-dihydro-isoindol-1-one is obtained.

$^1$H-NMR (400 MHz, CDCl3) δ ppm: 2.55-2.61 (m, 4H), 2.86 (t, 2H), 3.20 (s, 3H), 3.69-3.79 (m, 4H), 4.28 (t, 2H), 4.32 (s, 2H), 7.00 (d, 1H), 7.99 (d, 1H).

7-Amino-2-methyl-4-(2-morpholin-4-yl-ethoxy)-2,3-dihydro-isoindol-1-one is prepared by following the reaction described above. 340 mg of 7-amino-2-methyl-4-(2-morpholin-4-yl-ethoxy)-2,3-dihydro-isoindol-1-one is obtained from 380 mg of 2-methyl-4-(2-morpholin-4-yl-ethoxy)-7-nitro-2,3-dihydro-isoindol-1-one.

$^1$H-NMR (400 MHz, CDCl3) δ ppm: 2.50-2.64 (m, 4H), 2.76 (t, 2H), 3.13 (s, 3H), 3.69-3.77 (m, 4H), 4.10 (t, 2H), 4.26 (s, 2H), 4.78-4.96 (br.s, 2H), 6.55 (d, 1H), 6.82 (d, 1H).

The following 4-substituted-7-(2,5-dichloro-pyrimidin-4-ylamino)-2-methyl-2,3-dihydro-isoindol-1-ones are prepared from 4-substituted-7-amino-2-methyl-2,3-dihydro-isoindol-1-ones and 2,4,5-trichloropyrimidine following the procedure of Example 132.

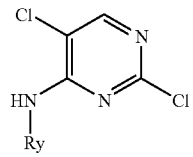

| Expl. No | Ry | Ms | NMR (400 MHz) |
|---|---|---|---|
| I41 | ![structure] | 508 | CDCl3: 1.48 (s, 9 H), 1.71-1.81 (m, 2 H), 1.91-2.02 (m, 2 H), 3.21 (s, 3 H), 3.31-3.4 (m, 2 H), 3.66-3.75 (m, 2 H), 4.37 (s, 2 H), 4.52-4.6 (m, 1 H), 7.09 (d, 1 H), 8.21 (s, 1 H), 8.66 (d, 1 H), 10.8 (s, 1 H) |

-continued

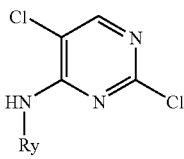

| Expl. No | Ry | Ms | NMR (400 MHz) |
|---|---|---|---|
| I42 | ![structure] | 438 | CDCl$_3$: 3.07 (m, 4 H), 3.2 (s, 3 H), 3.3 (t, 2 H), 3.9-4.0 (m, 4 H), 4.32 (s, 2 H), 4.4 (t, 2 H), 7.02 (d, 1 H), 8.21 (s, 1 H), 8.65 (d, 1 H), 10.8 (s, 1 H) |

Example I43:

Preparation of 5-methoxy-2-methyl-B-nitro-3,4-dihydro-2H-isoquinolin-1-one

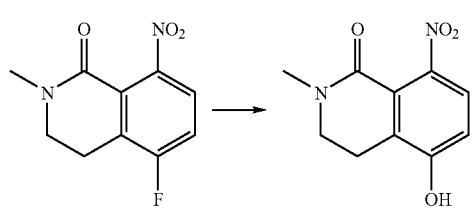

To a stirring solution of 5-fluoro-2-methyl-8-nitro-3,4-dihydro-2H-isoquinolin-1-one (2.24 g, 10 mmol) in DMF (15 mL) is added 2-(methylsulfonyl)ethanol (1.86 g, 15 mmol) and the solution cooled to 0° C. Sodium hydride (1.2 g, 30 mmol) is added and the reaction mixture allowed to warm to room temperature and then stirred for 1 hour. The mixture is quenched with a 1N HCl solution and partitioned between ethyl acetate and brine. The organic layer is concentrated to dryness and the crude organics purified by flash column chromatography to give 5-hydroxy-2-methyl-8-nitro-3,4-dihydro-2H-isoquinolin-1-one in 70% yields. $^1$H-NMR (400 MHz, δ, ppm) Acetone-d$_6$: 2.85-3.0 (m, 2H), 3.06 (s, 3H), 3.6-3.7 (m, 2H), 7.05-7.1 (m, 1H), 7.35-7.41 (m, 1H), 9.62 (brs, 1H).

Example I44:

Preparation of 5-methoxy-2-methyl-8-nitro-3,4-dihydro-2H-isoquinolin-1-one

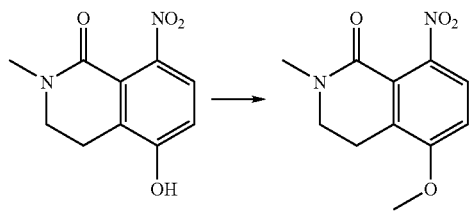

To a stirring solution of 5-Hydroxy-2-methyl-8-nitro-3,4-dihydro-2H-isoquinolin-1-one (444 mg, 2.0 mmol) and in DMF (5 mL) is added potassium carbonate (553 mg, 4.0 mmol.) and the solution cooled to 0° C. Iodomethane (0.25 mL, 4.0 mmol.) is added and the reaction mixture allow to warm to room temperature and then stirred for 1 hour. The mixture is quenched with a cold water and then the precipitate is filtered, washed with water and dried under vacuum to give a white solid corresponding to 5-methoxy-2-methyl-8-nitro-3,4-dihydro-2H-isoquinolin-1-one (336 mg, 71%).

$^1$H-NMR (400 MHz, δ, ppm) CDCl$_3$: 2.94 (t, 2H), 3.15 (s, 3H), 3.58 (t, 2H), 3.91 (s, 3H), 6.92 (d, 1H), 7.45 (d, 1H), 9.62 (brs, 1H).

The following 5-substituted-8-(2,5-dichloro-pyrimidin-4-ylamino)-2-methyl-3,4-dihydro-2H-isoquinolin-1-ones are prepared from 5-substituted-8-amino-2-methyl-3,4-dihydro-2H-isoquinolin-1-one and 2,4,5-trichloropyrimidine following the procedure of Example I32.

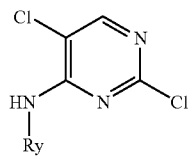

| No. | Ry | Ms | NMR (400 MHz) |
|---|---|---|---|
| I45 | ![structure] | 341 | CDCl₃: 3.04 (t, 2 H), 3.2 (s, 3 H), 3.6 (t, 2 H), 7.26 (dd, 1 H), 8.74 (dd, 1 H), 12.9 (s, 1 H) |
| I46 | ![structure] | 353 | DMSO: 2.92 (t, 2 H), 3.08 (s, 3 H) 3.56 (t, 2 H), 3.84 (s, 3 H), 7.32 (d, 1 H), 8.52 (d, 1 H), 12.9 (s, 1 H) |

Example I47:

Preparation of 1'-(4-amino-3-methoxy-phenyl)-[4,4'] bipiperidinyl-1-carboxylic acid tert-butyl ester

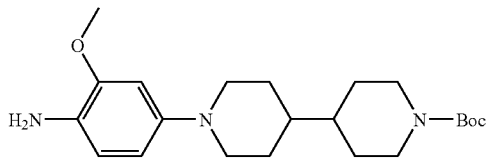

A mixture of 4-fluoro-2-methoxy-1-nitrobenzene (1.02 g, 5.97 mmol), [4,4']bipiperidinyl (3.6 g, 14.9 mmol), 2N sodium hydroxide (30 mL), toluene (15 mL) and n-butylammonium bromide (96 mg, 0.30 mmol) is vigorously stirred at 80° C. for 18 hours. After 10 mL of water is added, the mixture is filtrated. The residue is washed with water and then dried to give 1-(3-methoxy-4-nitro-phenyl)-[4,4']bipiperidine (1.79 g, 94% yield) as yellow solids.

$^1$H-NMR (400 MHz, δ, ppm) CDCl₃: 1.12-1.44 (m, 6H), 1.65-1.73 (m, 2H), 1.77-1.89 (m, 2H), 2.52-2.63 (m, 2H), 2.84-2.96 (m, 2H), 3.05-3.14 (m, 2H), 3.89-3.98 (m, 2H), 3.95 (s, 3H), 6.30 (d, 1H), 6.41 (dd, 1H), 8.00 (d, 1H).

To a suspension of 1-(3-methoxy-4-nitro-phenyl)-[4,4']bipiperidinyl (1.75 g, 5.48 mmol), di-tert-butyl-dicarboxylate (1.20 g, 5.48 mmol) in acetonitrile (55 mL), zirconium tetrachloride (128 mg, 0.55 mmol) is added and the mixture is stirred at ambient temperature for 30 min. After water and aqueous sodium hydrogen carbonate are added, the mixture is filtrated and dried to give 1'-(3-Methoxy-4-nitro-phenyl)-[4,4']bipiperidinyl-1-carboxylic acid tert-butyl ester (5.11 g, 92% yield) as yellow solids.

$^1$H-NMR (400 MHz, δ, ppm) CDCl₃: 1.10-1.43 (m, 6H), 1.46 (s, 9H), 1.64-1.72 (m, 2H), 1.76-1.89 (m, 2H), 2.58-2.71 (m, 2H), 2.84-2.95 (m, 2H), 3.90-3.99 (m, 2H), 3.95 (s, 3H), 4.06-4.22 (m, 2H), 6.30 (d, 1H), 6.41 (dd, 1H), 8.00 (d, 1H).

A mixture of 1'-(3-Methoxy-4-nitro-phenyl)-[4,4']bipiperidinyl-1-carboxylic acid tert-butyl ester (2.0 g, 4.77 mmol), iron powder (1.33 g, 23.85 mmol), 1N hydrogen chloride (9.54 mL, 9.54 mmol) in ethanol (50 mL) is stirred at 80° C. for 3 h. After cooling to room temperature, 2N hydrogen chloride (5 mL) and ethyl acetate are added and then the mixture is filtrated. After concentration in vacuo, the mixture is extracted with AcOEt, washed with brine, dried over sodium sulfate and evaporated to give 1'-(4-Amino-3-methoxy-phenyl)-[4,4']bipiperidinyl-1-carboxylic acid tert-butyl ester (1.77 g, 95% yield) as pale purple solids.

$^1$H-NMR (400 MHz, δ, ppm) CDCl₃: 1.09-1.33 (m, 4H), 1.37-1.50 (m, 2H), 1.46 (s, 9H), 1.66-1.74 (m, 2H), 1.75-1.83 (m, 2H), 2.50-2.59 (m, 2H), 2.59-2.73 (m, 2H), 3.42-3.59 (m, 4H), 3.83 (s, 3H), 4.03-4.23 (m, 2H), 6.42 (dd, 1H), 6.53 (d, 1H), 6.63 (d, 1H).

Example A:

FAK Assay

All steps are performed in a 96-well black microtiter plate. Purified recombinant hexahistidine-tagged human FAK kinase domain is diluted with dilution buffer (50 mM HEPES, pH 7.5, 0.01% BSA, 0.05% Tween-20 in water) to a concentration of 94 ng/mL (2.5 nM). The reaction mixture is prepared by mixing 10 μL 5× kinase buffer (250 mM HEPES, pH 7.5, 50 μM Na₃VO₄, 5 mM DTT, 10 mM MgCl₂, 50 mM MnCl₂, 0.05% BSA, 0.25% Tween-20 in water), 20 μL water, 5 μL of 4 μM biotinylated peptide substrate (Biot-Y397) in aqueous solution, 5 μL of test compound in DMSO, and 5 μL of recombinant enzyme solution and incubated for 30 min at room temperature. The enzyme reaction is started by addition of 5 μL of 5 μM ATP in water and the mixture is incubated for 3 hours at 37° C. The reaction is terminated by addition of 200 μL of detection mixture (1 nM Eu—PT66 (Perkin Elmer, No. AD0068), 2.5 μg/mL SA-(SL)APC (Perkin Elmer, No. CR130-100), 6.25 mM EDTA in dilution buffer), and the FRET signal from europium to allophycocyanin is measured by EnVision multilabel reader (Perkin Elmer) after 30 min of incubation at room temperature. The ratio of fluorescence intensity of 665 nm to 615 nm is used as a FRET signal for data analysis in order to cancel the colour quenching effect by a test compound. The results are shown as percent inhibition of enzyme activity. The level of the background signal is determined under the conditions without ATP, while DMSO is used as a control of 0% inhibition. $IC_{50}$ values are determined by non-linear curve fit analysis using the OriginPro 6.1 program (OriginLab).

The Biot-Y397 peptide (Biotin-SETDDYAEIID ammonium salt) is designed to have the same amino acid sequence as the region from S392 to D402 of human FAK (GenBank Accession Number L13616) and is prepared by standard methods.

Purified recombinant hexahistidine-tagged human FAK kinase domain is obtained in the following way: Full-length human FAK cDNA is isolated by PCR amplification from human placenta Marathon-Ready™ cDNA (Clontech, No 7411-1) with the 5' PCR primer (ATGGCAGCTGCTTAC-CTTGAC) and the 3' PCR primer (TCAGTGTG-GTCTCGTCTGCCC) and subcloned into a pGEM-T vector (Promega, No. A3600). After digestion with AccIII, the purified DNA fragment is treated with Klenow fragment. The cDNA fragment is digested with BamHI and cloned into pFastBacHTb plasmid (Invitrogen, 10584-027) previously cut with BamHI and Stu I. The resultant plasmid, hFAK KD (M384-G706)/pFastBacHTb, is sequenced to confirm its structure. The resulting DNA encodes a 364 amino acid protein containing a hexahistidine tag, a spacer region and a rTEV protease cleavage site at the N-terminal and the kinase domain of FAK (Met384-Gly706) from position 29 to 351.

Donor plasmid is transposed into the baculovirus genome, using MaxEfficacy DH10Bac *E. coli* cells (Invitrogen, No. 10361-012). Bacmid DNA is prepared by a simple alkaline lysis protocol described in the Bac-to-Bac® Baculovirus Expression system (Invitrogen, No. 10359-016). Sf9 insect cells are transfected based on the protocol provided by the vendor (CellFECTIN®, Invitrogen). The expression of FAK in each lysate is analysed by SDS-PAGE and Western blotting with anti-human FAK monoclonal antibody (Transduction Laboratories, No. F15020).

The virus clone that shows the highest expression is further amplified by infection to Sf9 cells. For large scale expression, amplified virus is infected to Expression in ExpresSF+® cells with 5 MOI for 72 hrs, these conditions give high level of protein with little degradation. Cell lysates are loaded onto a column of HiTrap™ Chelating Sepharose HP (Amersham Biosciences, No. 17-0409-01) charged with nickel sulfate and equilibrated with 50 mM HEPES pH 7.5, 0.5 M NaCl and 10 mM imidazole. Captured protein is eluted with increasing amounts of imidazole in HEPES buffer/NaCl, and the buffer is exchanged to 50 mM HEPES pH 7.5, 10% glycerol and 1 mM DTT by dialysis.

Example B

Phosphorylation Levels of FAK

Phosphorylation levels of FAK at Tyr397 is quantified by the sandwich ELISA. Mouse mammary carcinoma 4T1 cells ($1 \times 10^5$) are plated in wells of 96-well culture plates and incubated with or without various concentrations of inhibitors for 1 h in Dulbecco's modified eagle medium containing 0.5% BSA. The medium is removed and cells are lysed in 200 μL 50 mM Tris-HCl, pH 7.4, containing 1% NP-40, 0.25% sodium deoxycholate, 150 mM NaCl, 1 mM EDTA, 1 mM PMSF, 1 mM $Na_3VO_4$, 1 mM NaF, 1 μg/mL aprotinin, 1 μg/mL leupeptin and 1 μg/mL pepstatin. After centrifugation, the supernatants are subjected to a sandwich ELISA to quantify the phosphorylated FAK and total FAK. Cell lysates are applied to 96-well flat-bottom ELISA plates which have been pre-coated with 100 μL/well of 4 μg/mL mouse monoclonal anti-FAK antibody (clone 77, Becton Dickinson Transduction Laboratories) in 50 mM Tris-HCl, pH 9.5, containing 150 mM NaCl for 18 h at 4° C. and blocked with 300 μL of BlockAce (Dainippon Pharmaceuticals Co.) diluted at 1:4 with $H_2O$ at room temperature for 2 h. After washing with TBSN (20 mM Tris-HCl, pH 8.3, containing 300 mM NaCl, 0.1% SDS and 0.05% NP-40), total FAK is detected with 100 μL of 1 μg/ml anti-FAK polyclonal antibody (#65-6140, Upstate Biology Inc.), and phosphorylated FAK is detected with 100 μL of 0.25 μg/μL anti-phosphorylated FAK (Y397) antibody (Affinity BioReagents, #OPA1-03071) in BlockAce diluted at 1:10 with $H_2O$. After 1 h incubation at room temperature, plates are washed with TBSN and 100 μL of biotinylated anti-rabbit IgG (#65-6140, Zymed Laboratories Inc.) diluted at 1:2000 with BlockAce diluted at 1:10 with $H_2O$ is incubated at room temperature for 1 h. After washing with TBSN, ABTS solution substrate kit (#00-2011, Zymed Laboratories Inc.) is used for color development. Absorbance at 405 nm is measured after 20 min incubation at room temperature. The concentration of compound causing 50% reduction of phosphorylation level of FAK is determined.

Example C

Anchorage-Independent Tumor Cell Growth Assay

Mouse mammary carcinoma 4T1 cells ($5 \times 10^3$) are plated in 96-well Ultra low Attachment plates (#3474, Corning Inc.) in 100 μL of Dulbecco's modified eagle medium containing 10% FBS. Cells are cultured for 2 h and inhibitors are added at various concentrations in a final concentration of 0.1% DMSO. After 48 h, cell growth is assayed with the cell counting kit-8 (Wako Pure Chemical), which uses a water soluble tetrazolium salt WST8. Twenty μL of the reagent is added into each well and cells are further cultured for 2 h. The optical density is measured at 450 nm. The concentration of compound causing 50% inhibition of growth is determined.

Example D

In Vitro T Cell Migration Assay

Inhibitory activities of FAK inhibitors on the mobility of immune cells are secured by the following in vitro study. That is, Jurkat T human leukemic cell line are placed at $1 \times 10^5$ cells in the upper chamber of Fluoroblok with 8 μm pores (Beckton Dickinson, UK), and are allowed to migrate by four hours cultivation at 37° C., in 95% air-5% CO2 depending on a concentration gradient of fetal bovine serum (10% FBS). Cell mobility is appraised through the number of cells migrated into lower chamber by labeling with calcein-AM (Molecular Probes, Netherlands) at 8 μg/ml in HBSS for 1 h. For evaluation of FAK inhibitors, both the upper and lower chambers are added with various concentrations of FAK inhibitors (0.03-10 μM). IC50 values are calculated by the decrement of those fluorescent intensity compared to that in vehicle-treated group measured with Ascent (Ex: 485 nm, Em: 538 nm).

Example E

ALK Assay

The inhibition of ALK tyrosine kinase activity is measured using known methods, for example using the recombinant kinase domain of the ALK in analogy to the VEGF-R kinase assay described in J. Wood et al. Cancer Res. 60, 2178-2189 (2000).

The compounds of formula I potently inhibit the growth of human NPM-ALK overexpressing murine BaF3 cells. The expression of NPM-ALK is achieved by transfecting the BaF3 cell line with an expression vector pCIneo™ (Promega Corp., Madison Wis., USA) coding for NPM-ALK and subsequent selection of G418 resistant cells. Non-transfected BaF3 cells depend on IL-3 for cell survival. In contrast NPM-ALK expressing BaF3 cells (named BaF3-NPM-ALK) can proliferate in the absence of IL-3 because they obtain proliferative signal through NPM-ALK kinase. Putative inhibitors of the NPM-ALK kinase therefore abolish the growth signal and result in antiproliferative activity. The antiproliferative activity of putative inhibitors of the NPM-ALK kinase can however be overcome by addition of IL-3 which provides growth signals through an NPM-ALK independent mechanism. [for an analogous cell system using FLT3 kinase see E Weisberg et al. Cancer Cell; 1, 433-443 (2002). The inhibitory activity of the compounds of formula I is determined, briefly, as follows: BaF3-NPM-ALK cells (15 000/microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of Yopro™ staining (T Idziorek et al. J. Immunol. Methods; 185:249-58 [1995]): 25 μl of lysis buffer consisting of 20 mM sodium citrate, pH 4.0, 26.8 mM sodium chloride, 0.4% NP40, 20 mM EDTA and 20 mM was added to each well. Cell lysis was completed within 60 min at room temperature and total amount of Yopro bound to DNA was determined by measurement using the Cytofluor II 96-well reader (PerSeptive Biosystems) with the following settings: Excitation (nm) 485/20 and Emission (nm) 530/25. $IC_{50}$ values are determined by a computer-aided system using the formula:

$$IC_{50}=[(ABS_{test}-ABS_{start})/(ABS_{control}-ABS_{start})]\times 100.$$

The $IC_{50}$ value in those experiments is given as that concentration of the test compound in question that results in a cell count that is 50% lower than that obtained using the control without inhibitor. The compounds of formula I exhibit inhibitory activity with an $IC_{50}$ in the range from approximately 0.01 to 1 μM.

The antiproliferative action of the compounds of formula I can also be determined in the human KARPAS-299 lympoma cell line (described in W G Dirks et al. Int. J. Cancer 100, 49-56 (2002) using the same methodology described above for the BaF3-NPM-ALK cell line. The compounds of formula I exhibit inhibitory activity with an $IC_{50}$ in the range from approximately 0.01 to 1 μM.

Example F

In Vivo Activity in the Nude Mouse Xenograft Model female or male BALB/c nude mice (5-8 weeks old, Charles River Japan, Inc., Yokohama, Japan) are kept under sterile conditions with water and feed ad libitum. Tumours are induced by subcutaneous injection of tumour cells (human epithelial cell line MIA PaCa-2; European Collection of Cell Cultures (ECACC), Salisbury, Wiltshire, UK, Catalogue Number 85062806; cell line from a 65 year old Caucasian male; undifferentiated human pancreatic carcinoma cell line) into left or right flank of mice under Forene® anaesthesia (Abbott Japan Co., Ltd., Tokyo, Japan). Treatment with the test compound is started when the mean tumor volumes reached approximately 100 $mm^3$. Tumour growth is measured two times per week and 1 day after the last treatment by determining the length of two perpendicular axis. The tumour volumes are calculated in accordance with published methods (see Evans et al., Brit. J. Cancer 45, 466-8, 1982). The anti-tumour efficacy is determined as the mean increase in tumour volume of the treated animals divided by the mean increase in tumour volume of the untreated animals (controls) and, after multiplication by 100, is expressed as delta T/C [%]. Tumour regression is reported as the mean changes of tumor volume of the treated animals divided by the mean tumor volume at start of treatment and, after multiplication by 100, is expressed as regression [%]. The test compound is orally administered daily with or without drug holidays.

As an alternative to cell line MIA PaCa-2, another cell line may also be used in the same manner, for example:
the 4T1 breast carcinoma cell line (ATCC Number CRL-2539; see also Cancer. 88(12 Supple), 2979-2988, 2000) with female BALB/c mice (injection into mammary fat pad).

Example G

Tablets

Tablets comprising 50 mg of active ingredient, for example one of the compounds of formula I described in Examples 1 to 131, and having the following composition are prepared in customary manner:
Composition:

| | |
|---|---:|
| active ingredient | 50 mg |
| wheat starch | 150 mg |
| lactose | 125 mg |
| colloidal silicic acid | 12.5 mg |
| talc | 22.5 mg |
| magnesium stearate | 2.5 mg |
| Total: | 362.5 mg |

Preparation: The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plastic mass is obtained.

The plastic mass is pressed through a sieve of about 3 mm mesh size and dried, and the resulting dry granules are again forced through a sieve. Then the remainder of the wheat starch, the talc and the magnesium stearate are mixed in and the mixture is compressed to form tablets weighing 145 mg and having a breaking notch.

Example H

Soft Capsules 5000 soft gelatin capsules comprising each 50 mg of active ingredient, for example one of the compounds of formula I described in Examples 1 to 33, are prepared in customary manner:

Composition:

| active ingredient | 250 g |
| --- | --- |
| Lauroglykol | 2 litres |

Preparation: The pulverized active ingredient is suspended in Lauroglykol® (propylene glycol laurate, Gattefosse S.A., Saint Priest, France) and ground in a wet pulverizer to a particle size of approx. 1 to 3 μm. 0.419 g portions of the mixture are then dispensed into soft gelatin capsules using a capsule-filling machine.

The invention claimed is:

1. A compound of formula I

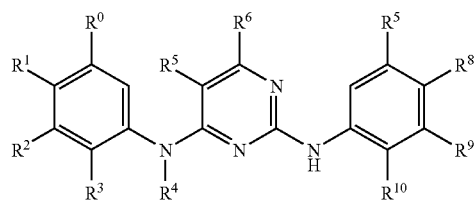

(I)

wherein
  $R_0$ is hydrogen
  $R_1$ is piperidinyl, piperazinyl or pyrazino-oxazinyl each of which is unsubstituted or substituted by pipereridinyl, hydroxy, $C_1$-$C_7$alkyl, piperazinyl, $C_1$-$C_7$alkyl-piperazinyl;
  $R_2$ and $R_3$ together with the C to which they are attached form a heterocycle comprising at least 1 heteroatoms selected from N which is unsubstituted or substituted once or more by a substituent independently selected from loweralkyl and oxo;
  $R_4$ is hydrogen
  $R_5$ is halogen
  $R_6$ is hydrogen
  $R_7$ is hydrogen;
  $R_8$ is hydrogen; $C_1$-$C_7$alkoxy; carbomyl unsubstituted or substituted by $C_1$-$C_7$alkyl; $C_1$-$C_7$alkoxy-$C_1$-$C_7$alkoxy:
a 5 or 6 membered heterocycle comprising 1, 2 hetero atoms independently selected from N or O and is unsubstituted or substituted by a substituent independently selected from hydroxy, $C_1$-$C_7$alkyl, mono or di-$C_1$-$C_7$atkylamino, a 6 membered heterocycle comprising 1 or 2 N ring atoms unsubstituted or substituted by $C_1$-$C_7$alkyl: 5 or 6 membered heterocycly- $C_1$-$C_7$alkoxy comprising 1 N ring atom unsubstituted or substituted by $C_1$-$C_7$alkyl;
  $R_9$ is hydrogen;
  $R_{10}$ is hydrogen, halogen or $C_1$-$C_7$alkoxy;
or a salt thereof.

2. A compound of formula I according to claim 1 wherein
  $R_0$ is hydrogen
  $R_1$ is piperidinyl, piperazinyl or pyrazino-oxazinyl each of which is unsubstituted or substituted by pipereridinyl, hydroxy, $C_1$-$C_7$alkyl, piperazinyl, $C_1$-$C_7$alkyl-piperazinyl;
  $R_2$ and $R_3$ together with the C to which they are attached form a heterocycle selected from the group consisting of indolyl or isoquinolinyl both of which are unsubstituted or substituted by $C_1$-$C_7$alkyl and / or oxo:
  $R_4$ is hydrogen
  $R_5$ is halogen
  $R_6$ is hydrogen
  $R_7$ is hydrogen;
  $R_8$ is hydrogen; $C_1$-$C_7$alkoxy; carbomyl unsubstituted or substituted by $C_1$-$C_7$alkyl; $C_1$-$C_7$alkoxy-$C_1$-$C_7$alkoxy; piperazinyl-$C_1$-$C_7$alkoxy; morpholino; piperindinyl; bipiperindinyl; pyrrolidinyl; piperazinyl- piperidinyl: wherein piperazinyl-$C_1$-$C_7$alkoxy, morpholino; piperindinyl, bipiperindinyl, pyrrolidinyl, piperazinyl-piperidinyl are unsubstituted or substituted by a substituent independently selected from hydroxy, $C_1$-$C_7$alkyl, mono or di-$C_1$-$C_7$alkylamino:
  $R_9$ is hydrogen;
  $R_{10}$ is hydrogen, halogen or $C_1$-$C_7$alkoxy;
or a salt thereof.

3. A compound of formula I according to claim 1 wherein $R_0$ is hydrogen $R_1$ is hydroxy-piperidinyl, piperidinyl-piperidinyl, piperazinyl, $C_1$-$C_7$alkyl-piperazinyl, piperazinyl- piperidinyl, $C_1$-$C_7$alkyl-piperazinyl-piperidinyl or pyrazino-oxazinyl;

$R_2$ and $R_3$ together with the C to which they are attached form a heterocycle selected from the group consisting of indolyl or isoquinolinyl both of which are substituted by $C_1$-$C_7$alkyl and oxo:

$R_4$ is hydrogen $R_5$ is halogen $R_6$ is hydrogen $R_7$ is hydrogen;

$R_8$ is hydrogen; $C_1$-$C_7$alkoxy; $C_1$-$C_7$alkyl-carbomyl unsubstituted; $C_1$-$C_7$alkoxy-$C_1$-$C_7$alkoxy; $C_1$-$C_7$alkyl-piperazinyl-$C_1$-$C_7$alkoxy; morpholino: hydroxy-piperindinyl; $C_1$-$C_7$alkyl-piperazinyl- piperindinyl; bipiperindinyl; di-$C_1$-$C_7$alkylamino pyrrolidinyl;

$R_9$ is hydrogen;

$R_{10}$ is hydrogen, halogen or $C_1$-$C_7$alkoxy;

or a salt thereof.

4. A compound of formula I according to claim 1 wherein $R_0$ is hydrogen $R_1$ is hydroxy-piperidinyl, piperidinyl-piperidinyl, piperazinyl, methyl-piperazinyl, isopropyl- piperazinyl, piperazinyl-piperidinyl, methyl-piperazinyl-piperidinyl or pyrazino-oxazinyl;

$R_2$ and $R_3$ together with the C to which they are attached form a heterocycle selected from the group consisting of methyl-isoindolone or methyl-isoquinolinone;

$R_4$ is hydrogen $R_5$ is chloro $R_6$ is hydrogen $R_7$ is hydrogen:

$R_8$ is hydrogen; methoxy; methyl-carbomyl unsubstituted; methoxy-ethoxy; methyl-piperazinyl- ethoxy: morpholino; hydroxy-piperindinyl; methyl-piperazinyl-piperindinyl: bipiperindinyl; dimethylamino-pyrrolidinyl;

$R_9$ is hydrogen;

$R_{10}$ is hydrogen, fluro or methoxy;

or a salt thereof.

5. A process for the production of a compound of formula I according to any one of claims 1 to 4, comprising reacting a compound of formula II

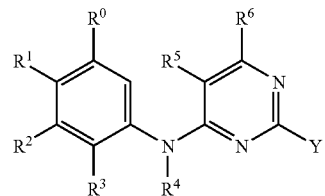

wherein $R^0$, $R^1$, $R^2$, $R^3$, $R^4$, $R^5$, and $R^6$ are as defined in claim 1, and Y is a leaving group, with a compound of formula III

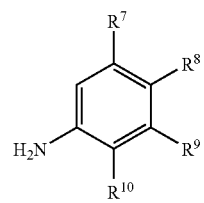

wherein $R^7$, $R^8$, $R^9$ and $R^{10}$ are as defined in claim 1;

and, if desired, converting a compound of formula I, wherein the substituents have the meaning as defined in claim 1, into another compound of formula I as defined in claim 1;

and recovering the resulting compound of formula I in free from or as a salt, and, when required, converting the compound of formula I obtained in free form into the desired salt, or an obtained salt into the free form.

6. A pharmaceutical composition comprising a compound of formula I according to any one of claims 1 to 4, as active ingredient together with one or more pharmaceutically acceptable diluents or carriers.

7. A method for the treatment of breast tumors in a subject in need thereof which comprises administering an effective amount of a compound of formula I, according to any one of claims 1 to 4, or a pharmaceutical composition comprising same.

8. A compound 7-[5-chloro-2-(2,4-dimethoxy-phenylamino)-pyrimidin-4-ylamino]-2-methyl-4-[4-(4-methyl-piperazin-1-yl)piperidin-1-yl]-2,3-dihydro-isoindol-1-one or a pharmaceutically acceptable salt thereof.

9. A pharmaceutical composition comprising the compound according to claim 8, or a pharmaceutically acceptable salt thereof, and one or more pharmaceutically acceptable diluents or carriers.

10. A method for the treatment of breast tumors in a subject in need thereof which comprises administering an effective amount of a compound according to claim 8, or a pharmaceutically acceptable salt thereof.

* * * * *

UNITED STATES PATENT AND TRADEMARK OFFICE
CERTIFICATE OF CORRECTION

PATENT NO. : 7,910,585 B2  
APPLICATION NO. : 11/660714  
DATED : March 22, 2011  
INVENTOR(S) : Kawahara et al.

Page 1 of 1

It is certified that error appears in the above-identified patent and that said Letters Patent is hereby corrected as shown below:

In claim 1, please replace the compound structure of formula I with the following compound structure:

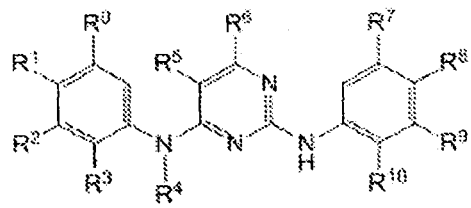

Signed and Sealed this  
Second Day of October, 2012

David J. Kappos  
*Director of the United States Patent and Trademark Office*